United States Patent
Bezwada

(10) Patent No.: US 8,802,892 B2
(45) Date of Patent: *Aug. 12, 2014

(54) FUNCTIONALIZED PHENOLIC COMPOUNDS AND POLYMERS THEREFROM

(71) Applicant: Bezwada Biomedical, LLC, Hillsborough, NJ (US)

(72) Inventor: Rao S Bezwada, Hillsborough, NJ (US)

(73) Assignee: Bezwada Biomedical, LLC, Hillsborough, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/654,068

(22) Filed: Oct. 17, 2012

(65) Prior Publication Data

US 2013/0281652 A1    Oct. 24, 2013

Related U.S. Application Data

(63) Continuation of application No. 12/089,101, filed as application No. PCT/US2006/060002 on Oct. 16, 2006, now Pat. No. 8,318,973.

(60) Provisional application No. 60/728,823, filed on Oct. 21, 2005.

(51) Int. Cl.
| | | |
|---|---|---|
| C07C 63/04 | (2006.01) |
| C07C 63/06 | (2006.01) |
| C07C 43/02 | (2006.01) |
| A61L 27/18 | (2006.01) |
| C07D 311/36 | (2006.01) |
| C07C 69/734 | (2006.01) |
| C07C 65/24 | (2006.01) |
| C08G 69/40 | (2006.01) |
| A61L 31/04 | (2006.01) |
| C07C 65/21 | (2006.01) |
| C07D 493/04 | (2006.01) |
| A61L 31/10 | (2006.01) |
| A23L 1/30 | (2006.01) |
| C07D 311/16 | (2006.01) |
| C08G 69/44 | (2006.01) |
| C07C 69/732 | (2006.01) |
| A61K 8/37 | (2006.01) |
| C08G 63/66 | (2006.01) |
| C07C 217/84 | (2006.01) |
| C07C 233/25 | (2006.01) |
| C07C 69/712 | (2006.01) |
| A23L 1/058 | (2006.01) |
| C07C 233/18 | (2006.01) |
| C07C 69/92 | (2006.01) |
| C07D 311/12 | (2006.01) |
| A61Q 19/08 | (2006.01) |
| C07C 205/37 | (2006.01) |
| A61Q 19/00 | (2006.01) |

(52) U.S. Cl.
CPC .............. *C08G 69/44* (2013.01); *A61L 27/18* (2013.01); *C07D 311/36* (2013.01); *C07C 69/734* (2013.01); *C07C 65/24* (2013.01); *C08G 69/40* (2013.01); *A61L 31/04* (2013.01); *C07C 65/21* (2013.01); *C07D 493/04* (2013.01); *A61L 31/10* (2013.01); *A23L 1/3002* (2013.01); *A23L 1/30* (2013.01); *C07D 311/16* (2013.01); *A61K 2800/522* (2013.01); *C07C 69/732* (2013.01); *A61K 8/37* (2013.01); *C08G 63/66* (2013.01); *C07C 217/84* (2013.01); *C07C 233/25* (2013.01); *C07C 69/712* (2013.01); *A23L 1/058* (2013.01); *C07C 233/18* (2013.01); *C07C 69/92* (2013.01); *C07D 311/12* (2013.01); *A61Q 19/08* (2013.01); *C07C 205/37* (2013.01); *A61Q 19/00* (2013.01)
USPC ............... 562/405; 562/490; 562/493; 560/8; 560/67; 560/70; 560/75; 560/85

(58) Field of Classification Search
CPC ........ C07C 15/04; C07C 15/24; C07C 15/18; C07C 15/58; C07C 43/257; C07C 43/263; C07C 43/267; C07C 43/275
USPC .............. 560/8, 67, 70, 75, 85; 562/405, 490, 562/493
See application file for complete search history.

(56) References Cited

U.S. PATENT DOCUMENTS

| 3,044,942 A | 7/1962 | Baptist |
| 3,297,033 A | 1/1967 | Schmitt |

(Continued)

FOREIGN PATENT DOCUMENTS

| WO | 97/39738 | 10/1997 |
| WO | 98/36013 | 8/1998 |

(Continued)

OTHER PUBLICATIONS

Gao et al. (J. Med. Chem. Published 2001, 3320-3328).*

(Continued)

*Primary Examiner* — Richard Schnizer
*Assistant Examiner* — Alma Pipic
(74) *Attorney, Agent, or Firm* — Vance Intellectual Property, PC

(57) ABSTRACT

The present invention relates to compounds of formula I, which are functionalized phenolic compounds, and polymers formed from the same.

$$Ar-[O-(X)_p-R']_q \quad \text{I}$$

Polymers formed from the functionalized phenolics are expected to have controllable degradation profiles, enabling them to release an active component over a desired time range. The polymers are also expected to be useful in a variety of medical applications.

13 Claims, No Drawings

(56) References Cited

U.S. PATENT DOCUMENTS

| | | |
|---|---|---|
| 3,371,069 A | 2/1968 | Miyamae |
| 3,531,561 A | 9/1970 | Trehu |
| 3,636,956 A | 1/1972 | Schneider |
| 3,773,737 A | 11/1973 | Goodman |
| 4,052,988 A | 10/1977 | Doddi |
| 4,130,639 A | 12/1978 | Shalaby |
| 4,532,928 A | 8/1985 | Bezwada |
| 4,605,730 A | 8/1986 | Shalaby |
| 4,653,497 A | 3/1987 | Bezwada |
| 4,689,424 A | 8/1987 | Shalaby |
| 4,829,099 A | 5/1989 | Fuller |
| 4,886,870 A | 12/1989 | D'Amore |
| 4,938,949 A | 7/1990 | Borch |
| 5,082,925 A | 1/1992 | Shalaby |
| 5,099,060 A | 3/1992 | Kohn |
| 5,264,540 A | 11/1993 | Cooper |
| 5,521,431 A | 5/1996 | Tahara |
| 5,637,755 A | 6/1997 | Nagumo |
| 5,759,830 A | 6/1998 | Vacanti |
| 5,801,033 A | 9/1998 | Hubbell |
| 5,834,274 A | 11/1998 | Hubbell |
| 5,834,513 A | 11/1998 | Ptchelintsev |
| 5,843,743 A | 12/1998 | Hubbell |
| 5,895,150 A | 4/1999 | Watabe |
| 5,902,599 A | 5/1999 | Anseth |
| 5,932,229 A | 8/1999 | Ptchelintset |
| 5,942,252 A | 8/1999 | Tice |
| 5,951,997 A | 9/1999 | Bezwada |
| 6,468,519 B1 | 10/2002 | Uhrich |
| 6,689,350 B2 | 2/2004 | Uhrich |
| 6,773,721 B1 | 8/2004 | Wong |
| 6,861,068 B2 | 3/2005 | Ng |
| 6,869,615 B2 | 3/2005 | Chen |
| 6,887,974 B2 | 5/2005 | Pathak |
| 6,890,561 B1 | 5/2005 | Blatt |
| 7,671,168 B2 * | 3/2010 | Bezwada ............ 528/272 |
| 7,902,319 B2 * | 3/2011 | Bezwada ............ 528/272 |
| 7,935,843 B2 * | 5/2011 | Bezwada ............ 560/40 |
| 8,309,754 B2 * | 11/2012 | Bezwada ............ 560/37 |
| 8,318,973 B2 * | 11/2012 | Bezwada ............ 562/405 |
| 8,436,201 B2 * | 5/2013 | Bezwada ............ 560/180 |
| 2002/0169275 A1 | 11/2002 | Matsuda |
| 2003/0158598 A1 | 8/2003 | Ashton |
| 2003/0216307 A1 | 11/2003 | Kohn |
| 2003/0232091 A1 | 12/2003 | Shefer |
| 2004/0096476 A1 | 5/2004 | Uhrich |
| 2004/0117007 A1 | 6/2004 | Whitbourne |
| 2005/0048121 A1 | 3/2005 | East |
| 2005/0074493 A1 | 4/2005 | Mehta |
| 2005/0095300 A1 | 5/2005 | Wynn |
| 2005/0112171 A1 | 5/2005 | Tang |
| 2005/0152958 A1 | 7/2005 | Cordes |
| 2005/0238689 A1 | 10/2005 | Carpenter |
| 2005/0245736 A1 | 11/2005 | Oreste |
| 2006/0013851 A1 | 1/2006 | Giroux |
| 2010/0113592 A1 | 5/2010 | Bezwada |

FOREIGN PATENT DOCUMENTS

| | | |
|---|---|---|
| WO | 99/12990 | 3/1999 |
| WO | 99/29885 | 6/1999 |
| WO | 01/41753 | 6/2001 |
| WO | 02/09767 | 2/2002 |
| WO | 02/09768 | 2/2002 |
| WO | WO 03/048226 A3 * | 6/2003 |
| WO | 2004/008101 | 1/2004 |
| WO | 2006/052790 | 5/2006 |
| WO | 2007/030464 | 3/2007 |
| WO | 2007/030538 | 3/2007 |

OTHER PUBLICATIONS

Kaufmann et al. (Nature, vol. 203, p. 520, Published Aug. 1964).*
SciFinder Scholar Report on Kaufmann reference (2 pages, accessed on Oct. 13, 2013).*
J. Org. Chem, 1959, 24, 523-526.
Gutowska et al, J. Biomater Res., 29, 811-21 (1995).
Hoffman, J. Controlled Release, 6, 297-305 (1987).
Mikos et al, Biomaterials, 14, 323-329 (1993).
Helder et al., J. Biomed. Mater. Res., (24), 1005-1020 (1990).
Barrera et al., Macromolecules, (28), 425-432 (1995).
Langer, R., Science 249: 1527-33 (1990).
Van Dijk-Wolthuis, W.N.W. et al., "Degradation and Release Behavior of Dextran-Based Hydrogels," Macromolecules, 30: 4639-45 (1997).
Van Dijk-Wolthuis, W.N.W. et al., "A new class of polymerizable dextrans with hydrolysable groups: hydroxyethyl methacrylated dextran with and without oligolactate spacer," Polymer 39(25); 6235-42 (1997).
Kurisawa, et al., Macromol. Chem. Phys. 199, 705-9 (1998).
Heller, J. et al., "Controlled release of water-soluble macromolecules from bioerodible hydrogels," Biomaterials 4; 262-6 (1983).
Brondsted, H. et al., "Hydrogels for site-specific oral drug delivery: synthesis and characterization," Biomaterials 12; 584-92 (1991).
Ulbrich, K. et al., "Novel biodegradable hydrogels prepared using the divinylic crosslinking agent N,O-dimethacryloylhydroxylamine 1. Synthesis and characterization of rates of gel degradation and rate of release of model drugs, in vitro and in vivo," J. Control. Release 24: 181-90 (1993).
Trenor, "Synthesis and characterization of tailored photoactive macromolecules," Apr. 16, 2004, Abstract p. 1, 5-7.
Vlasenko et al., Pharmaceutical Chemistry Journal 1993, 27(9), 648-51.
Canceill et al., Helvetica Chimica Acta 1982, 65 (Fasc. 6, Nr. 185), 1894-97.
Vermerris et al., Phenolic Compound Biochemistry, 2008, p. 1.

* cited by examiner

FUNCTIONALIZED PHENOLIC COMPOUNDS AND POLYMERS THEREFROM

FIELD OF THE INVENTION

The present invention relates to the discovery of functionalized phenolic compounds and polymers derived therefrom, which can have controllable degradation profiles.

BACKGROUND OF THE INVENTION

There are a vast number of known phenolic compounds or phenolics (e.g., flavonoids) with a variety of known beneficial uses. Phenolic and polyphenolic compounds are found widely in nature: in cereals, legumes, nuts, oilseeds, plant oils, fruits, vegetables, tea, coffee, cocoa, beer, wine, herbal products, such as Echinacea, ginseng, gingko biloba, St. John's wort, valerian, hawthorne, ginger, licorice, milk thistle, goldenseal, devil's claw, black cohosh, saw palmetto, and kava kava, for example. These substances are essential for growth and reproduction of plants and serve as antifeedants and antipathogens, among other purposes. Phenolic compounds can also aid in the maintenance of food, fresh flavor, taste, color, and prevention of oxidation deterioration. Many phenolic compounds are attracting the attention of food and medical scientists because of their antioxidative, anti-inflammatory, antimutagenic, and anticarcinogenic properties, and their capacity to modulate key cellular enzyme function. Phenolics pigment plant products and function as antibiotics, natural pesticides, signal substances for the establishment of symbiosis with rhizobia, attractants for pollinators, protective agents against ultraviolet light, insulating materials to make cell walls impermeable to gas and water, and as structural materials to give plants stability. The members of this class have many valuable uses in the fields of nutrition, nutriceuticals, pharmaceuticals, medicine, agriculture, chemistry, and in other fields of technology.

Unfortunately, phenolic compounds generally can be difficult to dissolve in water or the human body and can also be very difficult to polymerize in the phenolic state. Due to the availability and numerous uses of phenolics, it is desirable to enhance their native value by, for example, providing compounds or combinations of compounds with a specific controlled degradation profile or range enabling controlled release of the phenolic over an extended, controllable time range.

SUMMARY OF INVENTION

The present invention provides novel functionalized phenolic compounds, which are hydrolysable and can be useful for medical applications (e.g., drug delivery and solvent for dissolving drugs).

The present invention also provides novel, absorbable polymers and co-polymers (e.g., polyesters, polyamides, polyester amides, polyurethanes, and polyanhydrides) derived from functionalized phenolic compounds. These polymers are expected to have controllable degradation profiles.

The present invention also provides novel medical devices comprising functionalized phenolic compounds or polymers derived from functionalized phenolic compounds.

Other features of the present invention will be pointed out in the following description and claims.

DETAILED DESCRIPTION OF THE PRESENT INVENTION

The present invention provides novel functionalized phenolic compounds and absorbable polymers derived from them. The present invention is designed to extend the usefulness of phenolic compounds while retaining their inherent biological properties. The phenolic compounds are functionalized with safe and biocompatible molecules (e.g., glycolic acid, lactic acid, caprolactone, and dioxanone). The novel functionalized phenolic compounds of the present invention are expected to have controllable hydrolysis profiles, improved bioavailability, improved efficacy, and enhanced functionality.

Some of the functionalized phenolic compounds of the present invention can be monomers from which polymers can be made that are useful for medical applications. For example, a phenolic compound can be functionalized to form functionalized monomers that can then be polymerized to form absorbable polymers (e.g., polyesters, polyamides, polyester amides, polyurethanes, and polyanhydrides). It can be advantageous for the monomers that are to be polymerized to have at least two active sites (e.g., 2 or 3) for polymerization. These active sites include hydroxyl, amino, and carboxylic acid groups (e.g., two hydroxyl groups, a hydroxyl group and a carboxylic acid, a hydroxyl group and an amine group, a carboxylic acid group and an amino group, and two carboxylic acid groups). The functionalized phenolic compounds with at least two active sites can also be copolymerized with selected difunctional molecules (e.g., dicarboxylic acids, dialcohols, diisocyanates, amino-alcohols, hydroxycarboxylic acids, and diamines) based on the starting functionalized phenolic to form absorbable polymers. The polymers (and copolymers) of the present invention can also be further reacted/polymerized to form additional useful polymers of the present invention.

The definitions and examples provided in this application are not intended to be limiting, unless specifically stated.

Phenolic compound (also called phenolics) as used herein are defined substances that have at least one phenyl ring that is substituted with at least on hydroxyl group (e.g., hydroxyphenyl).

Phenolic residue means the portion of the phenolic compound remaining after removing a H from at least one hydroxyl group.

Ar, as used herein, is an aromatic moiety that typically has 1, 2, 3, 4, 5, or 6 aromatic rings (e.g., phenyl) and bear one or more hydroxyl substituents (e.g., 1, 2, 3, 4, 5, 6, 7, 8, 9, 10, 11, 12, 13, 4, 15, 16, 17, 18, 19, 20, 21, 22, 23, 24, and 25) on at least one of the aromatic rings. Additional examples of the number of aromatic groups present in the phenolic include (a) 1, 2, and 3 and (b) 1 and 2. Additional examples of the number of hydroxyl groups present on the phenolic include (a) 1, 2, 3, 4, and 5 and (b) 1 and 2. From one to all of the hydroxyl groups present on the phenolic compound may be functionalized. Phenolics are typically bioactive substances occurring widely in food plants that are eaten regularly by substantial numbers of animals and people and have been found to be safe compounds.

The aromatic rings of the Ar group can be fused together (e.g., naphthyl), bonded together (e.g., bi-phenyl), or linked together via a linking group. Typical linking groups include, O, $S(O)_{0-2}$, NH (or a substituted amine, e.g., $C_{1-6}$ alkyl, phenyl, or benzyl), $C_{1-6}$ alkylene, or a $C_{1-6}$ alkylene wherein one or two of the alkylene carbon atoms is replaced by one or two of the previously noted heteroatoms. The aromatic rings of the Ar group can also be fused to heteroaryl rings and/or non-aromatic rings. Examples of heteroaryl rings include 5-6 membered rings consisting of carbon atoms and 0-4 heteroatoms selected from O, N, and $S(O)_{0-2}$. Examples of non-aromatic rings include 5-6 membered carbocyclic or heterocyclic rings consisting of carbon atoms and 0-3 heteroatoms selected from O, N, and $S(O)_{0-2}$. The non-aromatic rings can consist of 0-2 ring double bonds as well as 0-2 carbonyl groups attached to the ring. Examples of non-aromatic rings include pyran and pyran-one. The non-aromatic rings can also be substituted by 1-2 carbonyl groups, in addition to other substituents defined elsewhere. When more than one aromatic ring is present (e.g., two phenyl rings), then they can be separated by a heteroaryl or non-aromatic ring as described above. For example, a phenyl ring can be bound to a chromene-2-one.

Examples of Ar include the following:

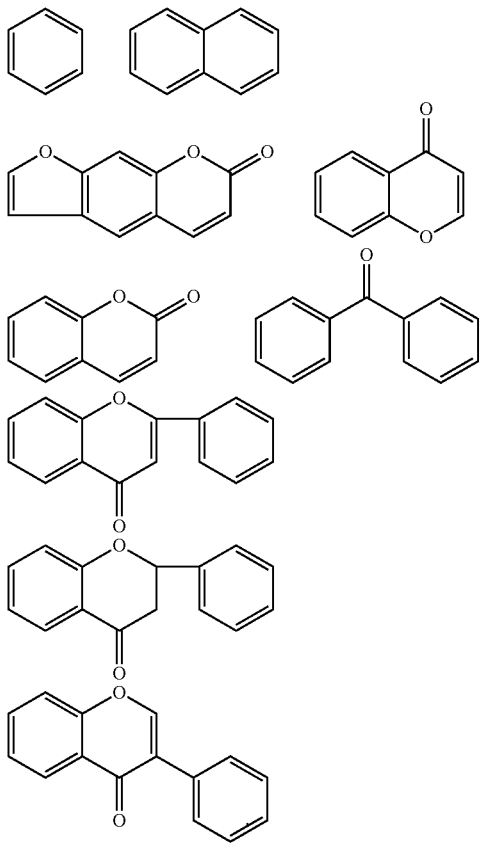

Each of the phenyl rings shown in the above examples can be substituted with 0, 1, or 2 OH groups, wherein at least one OH is present.

The Ar group of the present invention is substituted or unsubstituted. They can be substituted with (a) 1, 2, 3, 4, 5 or 6 R groups; (b) 1, 2, or 3 R groups; (c) 1 or 2 R; or (d) 1 R.

Examples of substituent R include H, =O, O-glycosides, —$(CH_2)_{0-2}$—$OR^a$, —$(CH_2)_{0-2}$—$C_6H_5$, —$(CH_2)_{0-2}$—CHO, Cl, F, Br, I, —$(CH_2)_{0-2}$—OC(O)—$R^a$, —$(CH_2)_{0-2}$—$CO_2$—$R^a$, —$(C(CH_3))_{0-2}$—$CO_2$—$R^a$, —$(CH_2)_{0-2}$—$CO_2$—$(CH_2)_{1-2}$—$CO_2$—$R^a$, —$(C(CH_3))_{0-2}$—$CO_2$—$(CH_2)_{1-2}$—$CO_2$—$R^a$, —$(CH_2)_{0-2}$—CO—$R^a$, —$O(CH_2)_{0-2}$—$C_6H_5$, —$O(CH_2)_{1-2}$—$CO_2$—$R^a$, —$O(C(CH_3))_{1-2}$—$CO_2$—$R^a$, —$O(CH_2)_{1-2}$—CO—$R^a$, —$CO_2(CH_2)_{1-2}$—$CO_2$—$R^a$, —$CO_2(C(CH_3))_{1-2}$—$CO_2$—$R^a$, —$(CH_2)_{0-2}$—$NO_2$, —$(CH_2)_{0-2}$—$NR^aR^a$, —$(CH_2)_{0-2}$—$NR^aCOR^a$, —$(CH_2)_{0-2}$—$NR^aC(O)(CH_2)_{1-2}OR^a$, —$C_6H_5$, —$C_6H_5OR^a$, and —$C_6H_5$—CH=$CHCO_2R^a$.

Examples of $R^a$ include H and $C_{1-6}$ alkyl;

As described herein, the functionalized phenolic compounds and polymers of the present invention are expected to be useful in medical applications/medical devices. Medical application/medical devices, as used herein, encompass medical and biomedical applications and include all types of applications involved in the practice of medicine that would benefit from a material that decomposes harmlessly within a known period of time. Examples include medical and surgical devices, which include drug delivery systems (e.g., a site-specific or systemic drug delivery systems or matrices), tissue engineering (e.g., tissue scaffold), stent coatings, stents, porous devices, implantable medical devices, molded articles (e.g., vascular grafts, stents, bone plates, sutures, implantable sensors, and barriers for surgical adhesion prevention), wound closure devices (e.g., surgical clips, staples, and sutures), coatings (e.g., for endoscopic instruments, sutures, stents, and needles), fibers or filaments (which may be attached to surgical needles or fabricated into materials including sutures or ligatures, multifilament yarn, sponges, gauze, tubes, and sheets for typing up and supporting damaged surface abrasions), rods, films (e.g., adhesion prevention barriers), knitted products, foodstuffs, nutritional supplements, nutriceuticals, cosmetics, pharmaceuticals, biodegradable chewing gums, flavors, enhanced drugs, drug intermediates, cancer preventing agents, antioxidants, controlled release preparations, and solvents for drugs. Examples of knitted products, woven or non-woven, and molded products include: burn dressings; hernia patches; medicated dressings; fascial substitutes; gauze, fabric, sheet, felt, or sponge for liver hemostasis; gauze bandages; arterial graft or substitutes; bandages for skin surfaces; suture knot clip; orthopedic pins, clamps, screws, and plates; clips (e.g., for vena cava); staples; hooks, buttons, and snaps; bone substitutes (e.g., mandible prosthesis); intrauterine devices (e.g., spermicidal devices); draining or testing tubes or capillaries; surgical instruments; vascular implants or supports; vertebral discs; extracorporeal tubing for kidney and heart-lung machines; and, artificial skin.

As used herein, "polymer" includes both polymers and copolymers depending on the number of different monomers used.

The present invention provides novel functionalized phenolic compounds of formula I or a pharmaceutically acceptable salt thereof:

$$Ar—[O—(X)_p—R']_q \quad \quad I$$

wherein:

Ar—$(O)_q$ is a phenolic residue;

X is selected from:

—$CH_2COO$— (glycolic acid moiety);

—$CH(CH_3)COO$— (lactic acid moiety);

—$CH_2CH_2OCH_2COO$— (dioxanone moiety);

—$CH_2CH_2CH_2CH_2CH_2COO$— (caprolactone moiety);

—$(CH_2)_yCOO$— where y is independently selected from 2, 3, 4, 6, 7, 8, 9, 10, 11, 12, 13, 14, 15, 16, 17, 18, 19, 20, 21, 22, 23, and 24; and, —$(CH_2CH_2O)_zCH_2COO$— where z is independently selected from 2, 3, 4, 5, 6, 7, 8, 9, 10, 11, 12, 13, 14, 15, 16, 17, 18, 19, 20, 21, 22, 23, and 24;

R' is selected from H, benzyl, and $C_{1-6}$ alkyl;

p is independently selected from 0, 1, 2, 3, and 4; and, q is selected from 1, 2, 3, 4, 5, 6, 7, 8, 9, 10, 11, 12, 13, 14, 15, 16, 17, 18, 19, 20, 21, 22, 23, 24, and 25;

provided that at least one X is present; and, further provided that when X is one and only one of —CH$_2$COO—, —CH(CH$_3$)COO—, or —CH$_2$CH$_2$CH$_2$CH$_2$CH$_2$COO— and q is 1 or 2, then p is ≥2.

Additional examples of q include (a) 1-10, (b) 1-5, (c) 1-3, (d) 1-2, and (e) 1.

It may also be advantageous for p to be ≥2, when q is 1 or 2 and X is one and only one —(CH$_2$)$_y$COO— where y is independently selected from 2, 3, 4, 6, and 7.

The group represented by X is attached via its carbon terminus to the oxygen group of the phenolic residue.

The rate of hydrolysis of the functionalized phenolics will depend upon a number of factors, including the functionalization species used and the number of functionalization species present on the functionalized phenolic (e.g., 1-6). Glycolic acid modified phenolics should hydrolyze faster than dioxanone modifies ones, where as lactic acid and caprolactone modified phenolics should take much longer to hydrolyze than glycolic acid and dioxanone modified phenolics. Furthermore, it is expected that the rate of hydrolysis will increase with the increase in the value of p and q. Thus, the desired time range may be obtained by altering the number and type of functionalization species used to functionalize the phenolic.

The present invention also provides novel functionalized phenolics of formula I, wherein:
  y is independently selected from 2, 3, and 4;
  z is independently selected from 2, 3, and 4;
  p is independently selected from 1, 2, and 3; and,
  q is selected from 1, 2, and 3.

The present invention also provides novel functionalized phenolics of formula I, wherein: X is selected from:
  —CH$_2$COO—;
  —CH(CH$_3$)COO—;
  —CH$_2$CH$_2$OCH$_2$COO—; and,
  —CH$_2$CH$_2$CH$_2$CH$_2$CH$_2$COO—;
    p is 2; and,
    q is selected from 1 and 2;

Examples of phenolic compounds expected to be useful in the present invention include phenols (e.g., hydroxy-benzene, dihydroxy-benzene (e.g., resorcinol, catechol, and hydroquinone), and tri-hydroxy-phenyls), naphthols (e.g., hydroxy-naphthyl, dihydroxy-naphthyl, tri-hydroxy-naphthyl, and tetra-hydroxy-napthyl), hydroxy-benzoic acids (e.g., hydroxy-benzoic acid and dihydroxy-benzoic acid), indoles, acetophenones, benzophenones, drugs containing phenolic groups (e.g., phenolic non-steroidal anti-inflammatory drugs, which include naproxen, paracetanol, acetaminophen, and acetylsalicylic acid), and, natural products containing phenolic groups, Examples of naturally occurring phenolics include the following compounds and their derivatives: cinnamic acids (e.g., 4-hydroxycinnamic acid, caffeic acid, chlorogenic acid, and ferulic acid), capsaicin, coumarins (e.g., 4-hydroxycoumarin), furanocoumarins (e.g., psoralen, bergapten, bergaptol, xanthotoxin, isopimpinellin, and 4,5',8-trimethylenepsoralen), alkaloids, catechins, chromones (including synthetic chromones), chalcones (including synthetic chromones), daidzein, 2,5-dihydroxybenzoic acid, flavonoids or bioflavonoids, isoflavones, resveratrol, sinapic acid, vanillic acid, and vanillin Examples of drugs containing phenolic groups include: acenocoumarol, acetarsol, actinoquinol, adrenalone, alibendol, amodiaquine, anethole, balsalazide, bamethan, benserazide, bentiromide, benzarone, benzquinamide, bevantolol, bifluranol, buclosamide, bupheniode, chlorotrianisene, chloroxylenol, cianidanol, cinepazide, cinitapride, cinepazide, cinmetacin, clebopride, clemastine, clioquinol, cyclovalone, cynarine, denopamine, dextroythyroxine, diacerein, dichlorophen, dienestrol, diethylstilbestrol, diflunisal, diiodohydroxyquinoline, dilazep, dilevalol, dimestrol, dimoxyline, diosmin, dithranol, dobutamine, donepezil, dopamine, dopexamine, doxazosin, entacapone, epanolol, epimestrol, epinephrine, estradiol valerate, estriol, estriol succinate, estrone, etamivan, etamsylate, ethaverine, ethoxzolamide, ethyl biscoumacetate, etilefrine, etiroxate, exalamide, exifone, fendosal, fenoldopam mesilate, fenoterol, fenoxedil, fenticlor, flopropione, floredil, fluorescein, folescutol, formoterol, gallopamil, gentistic acid, glaziovine, glibenclamide, glucametacin, guajacol, halquinol, hexachlorophene, hexestrol, hexobendine, hexoprenaline, hexylresorcinol, hydroxyethyl salicylate, hydroxystilbamidine isethionate, hymecromone, ifenprodil, indometacin, ipriflavone, isoetarine, isoprenaline, isoxsuprine, itopride hydrochloride, ketobemidone, khellin, labetalol, lactylphenetidin, levodopa, levomepromazine, levorphanol, levothyroxine, mebeverine, medrylamine, mefexamide, mepacrine, mesalazine, mestranol, metaraminol, methocarbamol, methoxamine, methoxsalen, methyldopa, midodrine, mitoxantrone, morclofone, nabumetone, nitroxoline, norfenefrine, normolaxol, octopamine, omeprazole, orciprenaline, oxilofrine, oxitriptan, oxyfedrine, oxypertine, oxyphenbutazone, oxyphenisatin acetate, oxyquinoline, papaverine, paracetanol, parethoxycaine, phenacaine, phenacetin, phenazocine, phenolphthalein, phenprocoumon, phentolamine, phloedrine, picotamide, pimobendan, prenalterol, primaquine, progabide, propanidid, protokylol, proxymetacaine, raloxifene hydrochloride, repaglinide, reproterol, rimiterol, ritodrine, salacetamide, salazosulfapyridine, salbutamol, salicylamide, salicylic acid, salmeterol, salsalate, sildenafil, silibinin, sulmetozin, tamsulosin, terazosin, terbutaline, tetroxoprim, theodrenaline, tioclomarol, tioxolone, α-tocopherol (vitamin E), tofisopam, tolcapone, tolterodine, tranilast, tretoquinol, triclosan, trimazosin, trimetazidine, trimethobenzamide, trimethoprim, trimetozine, trimetrexate glucuronate, troxipide, verapamil, vesnarinone, vetrabutine, viloxazine, warfarin, and xamoterol.

Additional examples of phenolics (e.g., bioactive phenolics) include the following compounds and their derivatives: acacetin, 4-acetamido-2-methyl-1-naphthol, albuterol, allenolic acid, aloe emodin, aloin, β-amino-4-hydroxy-3,5-diiodohydrocinnamic acid, N-(5-amino-2-hydroxyphenyl)-benzeneacetamide, 4-amino-1-naphthol, 3-aminosalicylic acid, 4-aminosalicylic acid, anacardic acid, p-anol, anthragallol, anthralin, anthranol, anthrarobin, anthrarufin, apigenin, apiin, apocynin, aspidinol, baptigenin, benzestrol, benzoresorcinol, bisphenol a, bisphenol b, butylated hydroxyanisole, butylated hydroxytoluene, capobenic acid, trans-1-(3'-carboxy-4'-hydroxyphenyl)-2-(2",5"-dihydroxyphenyl)ethane, catechin, m-chlorophenol, 5-chloro-8-quinolinol, chloroxylenol, chloroquinaldol, chromonar, chrysin, cinametic acid, chlorophene, coniferyl alcohol, p-coumaric acid, coumestrol, coumetarol, daphnetin, datiscetin, deoxyepinephrine, 3,5-diiodothyronine, 3,5-diiodotyrosine, dimethophrine, diosmetin, diresorcinol, disoprofol, dopa, dopamine, drosophilin a, efloxate, ellagic acid, embelin, Equol, eriodictyol, esculetin, esculin, ethylnorepinephrine, ethyl vanillin, eugenol, eupatorin, fenadiazole, fisetin, 3-fluoro-4-hydroxyphenylacetic acid, fraxetin, fustin, galangin, gallacetophenone, gallic acid, gardenins, genistein, gentisyl alcohol, gepefrine, geranylhydroquinone, [6]-gingerol, gossypol, guaiacol, guaifenesin, harmalol, hematoxylin, hinderin, homoeriodictyol, homogentisic acid, homovanillic acid, hydroxyamphetamine, 2-hydroxy-5-(2,5-dihydroxybenzylamino)-2-hydroxybenzoic acid, 4-hydroxy-3-methoxymandelic acid, n-(p-hydroxyphenyl)glycine, hydroxyprocaine, 8-hydroxyquinoline, hypericin, irigenin, isoproterenol, isoquercitrin, isothebaine, kaempferol, liothyronine, luteolin, mangostin, 5,5'-methylenedisalicylic acid, n-methylepinephrine, metyrosine, morin, mycophenolic acid, myricetin, naringenin, nylidrin, orcinol, osalmid, osthole, oxantel, paroxypropione, pentachlorophenol, 3-pentadecylcatechol, p-pentyloxyphenol, phloretin, phloroglucinol, pinosylvine, plumbagin, pyrocatechol, pyrogallol, quercetagetin, quercetin, resacetophenone, rhamnetin, rhein, sakuranetin, salicyl alcohol, salicylanilide, 4-salicyloylmorpholine, salsalate, scopoletin, scutellarein, serotonin, (3,4,5-trihydroxyphenyl)methylenepropanedinitrile, thymol, thyropropic acid, thyroxine, and tiratricol.

Flavonoids, sometimes called bioflavonoids, are 3-ring phenolic compounds consisting of a double ring attached by a single bond to a third ring. Examples include flavonoids, flavanones, flavones, flavanols, anthocyanidins, proanthocyanidins, procyanidolic oligomers (PCO), catechins, biflavans, polyphenols, rutin, rutinosides, hydroxyethylrutosides (HER), hesperidin, quercetin, quercetrin, polyphenols, catechin, epicatechin, epicatechin gallate, epigallocatechin gallate, and leucoanthocyanins. Flavonoids include the water-soluble pigments, such as anthocyanins, that are found in cell vacuoles. Flavonols are colorless or yellow flavonoids found in leaves and many flowers.

A therapeutic dose of bioflavonoids is helpful for conditions related to Chronic Venous Insufficiency (CVI). Some examples are: thrombophlebitis, thrombosis, varicose veins, leg ulcers, spider veins, hemorrhoids, chronic nosebleeds, prolonged menstrual bleeding. Even eye problems like macular degeneration and diabetic retinopathy have been helped with bioflavonoids. Along with the anti-inflammatory effects, bioflavonoids can be very helpful for tendonitis, arthritis, rheumatoid arthritis, joint injury, fibromyalgia, cellulite, and gout. Bioflavonoids, specifically proanthcyanidins, are found in grape seed extract. The proanthcyanidins appear to enhance the activity of vitamin C. The bioflavonoids in grape seed extract may also reduce the painful inflammation of swollen joints and prevent the oxidation of cholesterol in arteries that leads to plaque in the arterial walls.

Isoflavones exert a broad spectrum of biological activities. Besides antioxidant and estrogenic activities, isoflavones protect against several chronic diseases. Results of epidemiological studies indicate that consumption of soybean isoflavones lowers the incidence of breast, prostate, urinary tract and colon cancers. They also provide protection against coronary heart diseases and osteoporosis. Examples of isoflavones include are glycitein (isoflavone), daidzein, prunetin, biochanin A, orobol, santal, pratensein, formononetin, genistein, glycitein, and the glucosides, β-glycosides and other derivatives of the aforementioned isoflavones.

Resveratrol has been shown to lower the risk for coronary heart disease by inhibiting the plaque build-up or clogging of arteries by increasing the level of high density lipoproteins (HDLs) in the blood. Resveratrol also reduces blood platelet aggregation or clotting (thrombosis) within the blood vessels. Resveratrol belongs to the class of plant chemicals called phytoalexin. Plants use them as a defense mechanism in response to attacks by fungi and insects. One interesting phytoalexin called psolaren, having a chemical structure similar to coumarin, has been used in the treatment of certain cancers, including T-cell lymphomas in AIDS patients.

The capsaicins are amides of vanillylamine and $C_8$ and $C_{13}$ branched fatty acids. Examples of indications for capsaicins include peripheral neuropathic pain, post-herpetic neuralgia, trigeminal neuralgia, psoriasis, fibromyalgia, diabetic neuropathy, cluster headaches, earache, osteo- and rheumatoid arthritis, and as a pain reliever.

Sinapinic acid (sinapic acid) and its esterified forms are the predominant phenolic acid compounds found in rapeseed, contributing to its flavor and aroma. The sinapinic acid compounds have been shown to exhibit an anti-inflammatory action and have antimicrobial properties.

Tea polyphenols have been shown to block the nitrosation of amines by reducing nitrate to nitric acid or by forming C-nitroso compounds, thus blocking hepatotoxicity, lowering the risk of breast cancer metastasis. An example a component of green tea, epigallocatechin-3-gallate.

Further examples of phenolics useful in the present invention can be found in the following texts, which are incorporated by reference.

a. Shahidi, Ferriodoon and Marian Naczk, *Phenolics in Food and Nutriceuticals*, Boca Raton, Fla.: CRC Press, 2003.
b. Kleemann, A. et al, *Pharmaceutical Substances,* 4th Edition, Thieme (2000).
c. *Phenolic Compounds in Food and Their Effects on Health II; Antioxidants and Cancer Prevention*, ACS Symposium Series No. 507, Washington, D.C.: ACS, 1992.
d. *Food Phytochemicals for Cancer Prevention I*, ACS Symposium Series N. 546, Washington, D.C.: ACS, 1994.
e. *ROMPP Encyclopedia Natural Products*, New York: Thieme, 2000.
f. *The Merck Index, 12$^{th}$* edition, Rahway, N.J.: Merck and Company, 1996.
g. *A Single Source for Flavonoids and Coumarins* (2003), INDOFINE Chemical Company, Inc. 2004.

The starting material for the compounds of the present invention may be a phenolic compound or may be a precursor to a phenolic, such as a methoxyphenol, benzyloxyphenol or acetoxyphenol.

The present invention also provides a blend comprising one or more of the functionalization species with one or more species of phenolic compounds.

The present invention also provides polymers formed from the functionalized phenolic compounds of this invention that are difunctional, that is those species having more than one hydroxyl, carboxyl, ester, amino, cyano, or other polymerizable group. If the functionalized phenolic of the present invention only has one polymerizable moiety, then it can only be used as an endcap. Polymers of the functionalized phenolics are expected to have specific ranges over which they release the active phenolic moiety. One can blend polymers made from functionalized phenolics derived from one or more of the functionalization species and one or more species of phenolic moieties to obtain the release range desired for the specific application into the body of a mammalian, including a human or the environment. This release range varies with the species used for functionalization as well as the phenolic compound. The combinations or blends of these entities may comprise an amount of from 0.5% to 99.5% by weight of each species.

In addition, the monomers of the present invention may be polymerized to form absorbable polymers that display excellent physical, chemical, and biological properties, which make them useful in medical applications. The polymers of the present invention are expected to form non-toxic degradation products by hydrolytic chain cleavage under physiological conditions. The novel polymers of the present invention are expected to have increased rate of degradation and bioresorption as well as controllable degradation profile in comparison to the currently available polymers.

For example, a phenol, such as resorcinol, can be functionalized to form a reactive compound, which can be polymerized to form an absorbable polymer with a specific absorption profile. Similarly, each the phenolics described above can be functionalized to form reactive monomers. The polymers derived from these monomers will have unique physical and biological properties with absorption profiles that are controllable.

Thus, the present invention provides novel polymers formed from functionalized phenolic compounds of formula I:

$$Ar-[O-(X)_p-R']_q \qquad I$$

wherein:
$Ar-(O)_q$ is a phenolic residue;
X is selected from:
—$CH_2COO$— (glycolic acid moiety);
—$CH(CH_3)COO$— (lactic acid moiety);
—$CH_2CH_2OCH_2COO$— (dioxanone moiety);
—$CH_2CH_2CH_2CH_2CH_2COO$— (caprolactone moiety);
—$(CH_2)_yCOO$— where y is independently selected from 2, 3, 4, 6, 7, 8, 9, 10, 11, 12, 13, 14, 15, 16, 17, 18, 19, 20, 21, 22, 23, and 24; and,
—$(CH_2CH_2O)_zCH_2COO$— where z is independently selected from 2, 3, 4, 5, 6, 7, 8, 9, 10, 11, 12, 13, 14, 15, 16, 17, 18, 19, 20, 21, 22, 23, and 24;
R' is selected from H, benzyl, and $C_{1-6}$ alkyl;
p is independently selected from 0, 1, 2, 3, and 4; and,
q is selected from 1, 2, 3, 4, 5, 6, 7, 8, 9, 10, 11, 12, 13, 14, 15, 16, 17, 18, 19, 20, 21, 22, 23, 24, and 25;
provided that at least one X is present; and,
further provided that when $Ar-[O]_q$ is a hydroxy benzene, then $(X)_p$ is other than —$CH_2COO$— or —$CH_2CH_2CH_2CH_2CH_2COO$—.

The functionalized phenolic compounds of the present invention can be polymerized via conventional polymerization process using diol, triols, dicarboxylic acids, tricarboxylic acids, diamines, or triamines based on the starting difunctionalized or trifunctionalized phenolics, including those processes that synthesize polymers traditionally considered hydrolytically stable and non-biodegradable.

The present invention encompasses a variety of different polymers, some of which are copolymers. The polymers of the present invention include (a) polymers formed from one functionalized phenolic; (b) copolymers formed from more than one (e.g., 2, 3, or 4) type of functionalized phenolic (e.g., a blend of functionalized phenolic compounds that is polymerized); (c) copolymers formed from at least one type of functionalized phenolic having at least two active sites (e.g, 2 or 3) and a difunctional molecule (e.g., dicarboxylic acids, dialcohols, diisocyanates, amino-alcohols, hydroxy-carboxylic acids, and diamines); and (d) copolymers formed from at least one of the polymers of (a)-(c) and at least one lactone monomer (e.g., glycolide, lactide, e-caprolactone, trimethylene carbonate, and p-dioxanone). The absorption profile of the polymers of the present invention will depend upon a number of factors, including the functionalization species used and the number of functionalization species present on the functionalized phenolic (e.g., 1-6). Glycolic acid based polymers should hydrolyze faster than dioxanone based, where as lactic acid and caprolactone based polymers should take much longer to hydrolyze than glycolic acid and dioxanone based polymers. The desired time range may be obtained by altering the number and type of functionalization species as well as the number of different functionalized phenolic compounds (e.g., a blend of two or more functionalized phenolics). The desired time range will also be impacted by moieties used for co-polymerization (e.g., difunctional compounds or lactone monomers).

The functionalized phenolic polymers can be used in various medical applications described herein or can be further polymerized with lactone monomers, such as glycolide, lactide, ϵ-caprolactone, trimethylene carbonate, and p-dioxanone, and the resulting absorbable functionalized phenolic/lactone copolymers can be used in the various medical applications described herein.

As noted above, more than one of the functionalized phenolic compounds of the present invention can be blended and polymerized to form a functionalized phenolic copolymer. The functionalized phenolic copolymers can be used in various medical applications described herein or can be further polymerized with lactone monomers, such as glycolide, lactide, ϵ-caprolactone, trimethylene carbonate, and p-dioxanone, and the resulting absorbable polymers can also have the medical applications described herein.

As noted above, the functionalized phenolic compounds of the present invention with at least two reactive sites can be polymerized with difunctional molecules (e.g., dicarboxylic acids, dialcohols, diisocyanates, amino-alcohols, hydroxy-carboxylic acids, and diamines) to form absorbable polymers, including but not limited to polyesters, polyester amides, polyurethanes, polyamides, and polyanhydrides by simple polycondensation reactions. The functionalized phenolic/difunctional molecule polymers can be used in various medical applications or can be further polymerized with lactone monomers, such as glycolide, lactide, ϵ-caprolactone, trimethylene carbonate, and p-dioxanone, and the resulting absorbable polymers potential have the medical applications described above.

In another example of the present invention, functionalized dihydroxy phenolic compounds of the present invention can be used in the preparation of polyesters by reacting with dicarboxylic acid compounds. Dicarboxylic acids useful in the present invention have the following structure:

$$HOOC-R-COOH$$

wherein R is selected from saturated and unsaturated, substituted and unsubstituted alkyl, aryl and alkylaryl groups having from 1, 2, 3, 4, 5, 6, 7, 8, 9, 10, 11, 12, 13, 14, 15, 16, 17, and 18 carbon atoms In another example of the present invention, functionalized dicarboxylic acid phenolic compounds of the present invention can be used in the preparation of polyesters by reacting with the dialcohol (i.e., diol) compounds. Dialcohols useful in the present invention have the following structure:

$$HO-R-OH$$

wherein R is selected from saturated and unsaturated, substituted and unsubstituted alkyl, aryl and alkylaryl groups having from 2, 3, 4, 5, 6, 7, 8, 9, 10, 11, 12, 13, 14, 15, 16, 17, and 18 carbon atoms. Alternatively, polyalkylene oxides have weight average molecular weights from about 500-5,000 can be used as a diol (i.e., a polydiol). Suitable diols or polydiols for use in the present invention are diol or diol repeating units with up to 8 carbon atoms. Examples of suitable diols include 1,2-ethanediol (ethylene glycol); 1,2-propanediol (propylene glycol); 1,3-propanediol; 1,4-butanediol; 1,5-pentanediol; 1,3-cyclopentanediol; 1,6-hexanediol; 1,4-cyclohexanediol; 1,8-octanediol; and, combinations thereof. Examples of polydiols include polyethylene glycol and polypropylene glycol with weight average molecular weights of 500-5000.

In another example of the present invention, functionalized dihydroxy phenolic compounds of the present invention can be used in the preparation of polyurethanes by reacting with diisocyante compounds. Examples of diisocyanates include hexamethylene diisocyante, lysine diisocyanate, methylene diphenyl diisocyanate (e.g., MDI), Hated MDI (e.g., methylene dicyclohexyl diisocyanate), and isophorone diisocyanate.

In another example of the present invention, functionalized hydroxy-amino phenolic compounds of the present invention can be used in the preparation of polyesteramides by reacting with dicarboxylic acid compounds described above.

In another example of the present invention, functionalized dicarboxylic acid phenolic compounds of the present invention can be used in the preparation of polyesteramides by reacting with the amino-alcohol compounds Amino-alcohols useful in the present invention have the following structure:

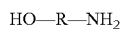

HO—R—NH$_2$ wherein R is selected from saturated and unsaturated, substituted and unsubstituted alkyl, aryl and alkylaryl groups having from 2, 3, 4, 5, 6, 7, 8, 9, 10, 11, 12, 13, 14, 15, 16, 17, and 18 carbon atoms.

In another example of the present invention, functionalized hydroxy-carboxylic acid phenolic compounds of the present invention can be used in the preparation of polyesters by reacting with hydroxycarboxylic acid compounds. Hydroxycarboxylic acids useful in the present invention have the following structure:

HO—R—COOH wherein R is selected from saturated and unsaturated, substituted and unsubstituted alkyl, aryl and alkylaryl groups having from 1, 2, 3, 4, 5, 6, 7, 8, 9, 10, 11, 12, 13, 14, 15, 16, 17, and 18 carbon atoms, In another example of the present invention, functionalized amino-carboxylic acid phenolic compounds of the present invention can be used in the preparation of polyesteramides by reacting with the hydroxycarboxylic acid compounds described above.

In another example of the present invention, functionalized dicarboxylic acid phenolic compounds of the present invention can be used in the preparation of polyamides by reacting with the diamine compounds. Diamines useful in the present invention have the following structure:

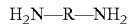

H$_2$N—R—NH$_2$ wherein R is selected from saturated and unsaturated, substituted and unsubstituted alkyl, aryl and alkylaryl groups having from 2, 3, 4, 5, 6, 7, 8, 9, 10, 11, 12, 13, 14, 15, 16, 17, and 18 carbon atoms. Alternatively, polyalkylene oxides that are diamines with weight average molecular weights from about 500-5,000 can be used.

In another example of the present invention, functionalized dicarboxylic acid phenolic compounds of the present invention can be used in the preparation of polyanhydrides by reacting with the dicarboxylic acid compounds described above.

The functionalized phenolic compounds of the present invention having more than two reactive groups (e.g., 3) are expected to be useful in the preparation of cross linked hydrogels and are prepared Examples of polymers of the present invention have weight-average molecular weights above about 20,000 daltons or above about 100,000 daltons, calculated from gel permeation chromatography (GPC) relative to polystyrene standards in tetrahydrofuran (THF) without further correction.

The polymers of the present invention should be able to be processed by known methods commonly employed in the field of synthetic polymers to provide a variety of useful articles with valuable physical and chemical properties. The useful articles can be shaped by conventional polymer-forming techniques such as extrusion, compression molding, injection molding, solvent casting, and wet spinning Shaped articles prepared from the polymers are expected to be useful as degradable devices for medical implant applications.

The present invention also relates to a composition, comprising: at least two (e.g., 2, 3, 4, or 5) functional phenolic compounds of the present invention. The present invention also relates to a composition, comprising: at least one functionalized phenolic, wherein the composition is suitable for use as at least one of the following: (a) a solvent for drugs; (b) a nutritional compound; (c) a cosmetic: and, (d) a pharmaceutical. Each of the compositions may further comprise an additional component suitable for such composition. For example, when the composition is suitable for use as a cosmetic it may further comprise: one or more cosmetic ingredients. Also, when the composition is suitable for use as a pharmaceutical it may further comprise: one or more pharmaceutically acceptable excipients. In addition, each of the compositions may comprise a functionalized phenolic derived from a phenolic having a property useful to that type of composition. For example, the starting phenolic may be (a) a nutritional supplement or a food intermediary; (b) an anti-cancer agent; (c) an antimicrobial agent; (d) an anti-inflammatory agent; (e) a pain-reducer; and, (f) an antioxidant agent. Also, the compositions may further comprise one of agents (a)-(f).

The compositions of the present invention may be suitable for administration via a route selected from oral, enteral, parenteral, topical, transdermal, ocular, vitreal, rectal, nasal, pulmonary, and vaginal.

The implantable medical devices of the present invention, comprise: at least one absorbable polymer of the present invention. For example, a polymer of the present invention can be combined with a quantity of a biologically or pharmaceutically active compound sufficient to be therapeutically effective as a site-specific or systemic drug delivery system (see Gutowska et al., J. Biomater. Res., 29, 811-21 (1995) and Hoffman, J. Controlled Release, 6, 297-305 (1987)). Another example of the present invention is a method for site-specific or systemic drug delivery by implanting in the body of a patient in need thereof an implantable drug delivery device comprising a therapeutically effective amount of a biologically or a physiologically active compound in combination with at least one absorbable polymer of the present invention.

In another example, at least one polymer of the present invention is formed into a porous device (see Mikos et al., Biomaterials, 14, 323-329 (1993) or Schugens et al., J. Biomed. Mater. Res., 30, 449-462 (1996)) to allow for the attachment and growth of cells (see Bulletin of the Material Research Society, Special Issue on Tissue Engineering (Guest Editor: Joachim Kohn), 21(11), 22-26 (1996)). Thus, the present invention provides a tissue scaffold comprising a porous structure for the attachment and proliferation of cells either in vitro or in vivo formed from at least one absorbable polymer of the present invention The present invention also relates to an article (e.g., an implantable medical device), comprising: a metal or polymeric substrate having thereon a coating, wherein the coating, comprises: at least one polymer of the present invention.

The present invention also relates to a molded article prepared from at least one polymer of the present invention.

The present invention also relates to a controlled drug delivery system, comprising: at least one polymer of the present invention physically admixed with a biologically or pharmacologically active agent. For example, the controlled drug delivery system can comprise: a biologically or pharmacologically active agent coated with at least one polymer of the present invention.

The present invention also relates to a controlled drug delivery system, comprising: a biologically or pharmacologically active agent physically embedded or dispersed into a polymeric matrix formed from at least one polymer of the present invention.

The present invention also relates to a tissue scaffold having a porous structure for the attachment and proliferation of cells, either in vitro or in vivo, formed from one least one polymer of the present invention.

The present invention also relates to a composition, comprising: at least one polymer of the present invention, which has been further polymerized with at least one lactone monomer selected from: glycolide, lactide, p-dioxanone, trimethylene carbonate, and caprolactone.

The present invention also relates to an implantable biomedical device, comprising: at least one polymer that has been further polymerized with at least one lactone monomer.

The present invention also relates to a biodegradable chewing gum composition, comprising: an effective amount of at least one polymer that has been further polymerized with at least on lactone monomer.

The present invention also relates to an article (e.g., an implantable medical device), comprising: a metal or polymeric substrate and having thereon a coating, wherein said coating comprises at least one polymer that has been further polymerized with at least one lactone monomer.

The present invention also relates to a molded article prepared from at least one polymer that has been further polymerized with at least one lactone monomer.

The present invention also relates to a monofilament or multifilament prepared from at least one polymer that has been further polymerized with at least one lactone monomer.

The present invention also relates to a controlled drug delivery system, comprising: at least one polymer that has been further polymerized with at least one lactone monomer, which has been physically admixed with a biologically or pharmacologically active agent.

The present invention also relates to a controlled drug delivery system, comprising: a biologically or pharmacologically active agent physically embedded or dispersed into a polymeric matrix formed from at least one polymer that has been further polymerized with at least one lactone monomer.

The present invention also relates to a tissue scaffold having a porous structure for the attachment and proliferation of cells, either in vitro or in vivo, formed from at least one polymer that has been further polymerized with at least one lactone monomer.

The present invention also relates to low molecular weight polymers or oligomers of the functionalized phenolic compounds of the present invention that are further reacted to form reactive end groups (e.g., isocyanates, expoxides, and acrylates). Low-molecular weight polymers or oligomers as used herein means a polymer having a number average molecular weight of about 500-20,000 or 500-10,000. For example, some of the functionalized phenolic compounds behave chemically like diols. They can be reacted with dicarboxylic acids to form polyesters, which are usually hydroxyterminated. These hydroxyterminated oligomers can be further reacted to form isocyanates, epoxides and acrylates. Similarly the functionalized phenolic compounds can be reacted with isocyanates to make urethanes. Thus, the present invention also includes a composition, comprising: at least one polymer of the present invention, which has been further reacted to form reactive end groups.

The present invention also relates to polymers made from functionalized phenolic compounds that have been sterilized by cobalt-60 radiation, electron beam radiation, and/or ethylene oxide.

"Bioabsorbable" or "absorbable" as used herein means that the material readily reacts or enzymatically degrades upon exposure to bodily tissue for a relatively short period of time, thereby experiencing a significant weight loss in that short period of time. Complete bioabsorption/absorption should take place within twelve months, although it may be complete within nine months or within six months. In this manner, the polymers of the present invention can be fabricated into medical and surgical devices, which are useful for a vast array of applications requiring complete absorption within a relatively short time period.

The biological properties of the bioabsorbable polymers of the present invention used to form a device or part thereof, as measured by its absorption rate and its breaking strength retention in vivo (BSR), can be varied to suit the needs of the particular application for which the fabricated medical device or component is intended. This can be conveniently accomplished by varying the ratio of components of the polymer chosen.

"Pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 1,2-ethanedisulfonic, 2-acetoxybenzoic, 2-hydroxyethanesulfonic, acetic, ascorbic, benzenesulfonic, benzoic, bicarbonic, carbonic, citric, edetic, ethane disulfonic, ethane sulfonic, fumaric, glucoheptonic, gluconic, glutamic, glycolic, glycollyarsanilic, hexylresorcinic, hydrabamic, hydrobromic, hydrochloric, hydroiodide, hydroxymaleic, hydroxynaphthoic, isethionic, lactic, lactobionic, lauryl sulfonic, maleic, malic, mandelic, methanesulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, and toluenesulfonic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences,* 18th ed., Mack Publishing Company, Easton, Pa., 1990, p 1445, the disclosure of which is hereby incorporated by reference.

"Therapeutically effective amount" includes an amount of a compound of the present invention that is effective when administered alone or in combination to treat the desired indication.

"Alkyl" includes both branched and straight-chain saturated aliphatic hydrocarbon groups having the specified number of carbon atoms. $C_{1-6}$ alkyl, for example, includes $C_1$, $C_2$, $C_3$, $C_4$, $C_5$, and $C_6$ alkyl groups. Examples of alkyl include methyl, ethyl, n-propyl, i-propyl, n-butyl, s-butyl, t-butyl, n-pentyl, s-pentyl, and n-hexyl.

Polymers of the present invention may be made in the form of random copolymers or block copolymers. A coupling agent may also be added to the polymers of the present invention. A coupling agent is a reagent that has a least two functional groups that are capable of covalently bonding to two different monomers. Examples of coupling agents include trifunctional or tetrafunctional polyols, oxycarboxylic acids, and polybasic carboxylic acids (or acid anhydrides thereof). Other coupling agents include the difunctional groups (e.g., diols, diacids, diamines, and hydroxy-acids) previously discussed. The addition of the coupling agents causes the branching of long chains, which can impart desirable properties in the molten state to the pre-polymer. Examples of polyfunctional coupling agents include trimethylol propane, glycerin, pentaerythritol, malic acid, citric acid, tartaric acid, trimesic acid, propane tricarboxylic acid, cyclopentane tetracarboxylic anhydride, and combinations thereof.

A "pre-polymer" is a low-molecular weight polymer, as previously defined, that have reactive endgroups (e.g., hydroxy groups) that can be further reactive with, for example, the lactone monomers.

The amount of coupling agent to be added before gelation occurs is a function of the type of coupling agent used and the polymerization conditions of the polymer or molecular weight of the pre-polymer to which it is added. Generally in the range of from about 0.1 to about 10 mole percent of a trifunctional or a tetrafunctional coupling agent may be added based on the moles of polymers present or anticipated from the synthesis.

The polymerization of a polyester of the present invention can be performed under melt polycondensation conditions in the presence of an organometallic catalyst at elevated temperatures. The organometallic catalyst can be a tin-based catalyst (e.g., stannous octoate or dibutyl tin oxide). The catalyst can be present in the mixture at a mole ratio of diol, dicarboxylic acid, and optionally lactone monomer to catalyst will be in the range of from about 15,000/1 to 80,000/1. The reaction can be performed at a temperature not less than about 120° C. under reduced pressure. Higher polymerization temperatures may lead to further increases in the molecular weight of the copolymer, which may be desirable for numerous applications. The exact reaction conditions chosen will depend on numerous factors, including the properties of the polymer desired, the viscosity of the reaction mixture, and the glass transition temperature and softening temperature of the polymer. Desired reaction conditions of temperature, time and pressure can be readily determined by assessing these and other factors. Generally, the reaction mixture will be maintained at about 220° C. The polymerization reaction can be allowed to proceed at this temperature until the desired molecular weight and percent conversion is achieved for the copolymer, which will typically take about 15 minutes to 24 hours. Increasing the reaction temperature generally decreases the reaction time needed to achieve a particular molecular weight.

Polymerization conditions for the preparation of other types of polymers of the present invention (e.g., polyamides and polyurethanes) are described in the literature. Those skilled in the art will recognize that the polymers described herein can be made from known procedures.

Copolymers of the absorbable polymers of the present invention can be prepared by preparing a pre-polymer under melt polycondensation conditions, then adding at least one lactone monomer or lactone pre-polymer. The mixture could then be subjected to the desired conditions of temperature and time to copolymerize the pre-polymer with the lactone monomers.

A lactone pre-polymer is a pre-polymer formed by ring opening polymerization with a known initiator (e.g., ethylene glycol, diethylene glycol, glycerol, or other diols or triols).

The molecular weight of the pre-polymer as well as its composition can be varied depending on the desired characteristic, which the pre-polymer is to impart to the copolymer. For example, the pre-polymers of the present invention, from which the copolymer is prepared, generally have a molecular weight that provides an inherent viscosity between about 0.2 to about 2.0 deciliters per gram (dl/g) as measured in a 0.1 g/dl solution of hexafluoroisopropanol at 25° C. Those skilled in the art will recognize that the pre-polymers described herein can also be made from mixtures of more than one diol or dicarboxylic acid.

One of the beneficial properties of the polyesters of the present invention is that the ester linkages are hydrolytically unstable, and therefore the polymer is bioabsorbable because it readily breaks down into small segments when exposed to moist bodily tissue. In this regard, while it is envisioned that co-reactants could be incorporated into the reaction mixture of the dicarboxylic acid and the diol for the formation of the polyester pre-polymer, it is preferable that the reaction mixture does not contain a concentration of any co-reactant which would render the subsequently prepared polymer nonabsorbable. The reaction mixture can be substantially free of any such co-reactants if the presence thereof results in a nonabsorbable polymer.

The polymers of the present invention can be melt processed by numerous methods to prepare a vast array of useful devices. These polymers can be injection or compression molded to make implantable medical and surgical devices, especially wound closure devices.

Alternatively, the polymers can be extruded to prepare fibers. The filaments thus produced may be fabricated into sutures or ligatures, attached to surgical needles, packaged, and sterilized by known techniques. The polymers of the present invention may be spun as multifilament yarn and woven or knitted to form sponges or gauze, (or non-woven sheets may be prepared) or used in conjunction with other molded compressive structures as prosthetic devices within the body of a human or animal where it is desirable that the structure have high tensile strength and desirable levels of compliance and/or ductility. Examples include tubes, including branched tubes, for artery, vein, or intestinal repair, nerve splicing, tendon splicing, sheets for typing up and supporting damaged surface abrasions, particularly major abrasions, or areas where the skin and underlying tissues are damaged or surgically removed.

Additionally, the polymers can be molded to form films which, when sterilized, are useful as adhesion prevention barriers. Another alternative processing technique for the polymers of the present invention includes solvent casting, particularly for those applications where a drug delivery matrix is desired.

The polymers of the present invention can be used to coat a surface of a surgical article to enhance the lubricity of the coated surface. The polymer may be applied as a coating using conventional techniques. For example, the polymer may be solubilized in a dilute solution of a volatile organic solvent (e.g. acetone, methanol, ethyl acetate, or toluene), and then the article can be immersed in the solution to coat its surface. Once the surface is coated, the surgical article can be removed from the solution where it can be dried at an elevated temperature until the solvent and any residual reactants are removed.

For coating applications, the polymer should exhibit an inherent viscosity, as measured in a 0.1 gram per deciliter (g/dl) of hexafluoroisopropanol (HFIP), between about 0.05-2.0 dl/g or about 0.10-0.80 dl/g. If the inherent viscosity were less than about 0.05 dl/g, then the polymer may not have the integrity necessary for the preparation of films or coatings for the surfaces of various surgical and medical articles. On the other hand, it is possible to use polymers with an inherent viscosity greater than about 2.0 dl/g, though it may be difficult to do so.

Although numerous surgical articles (including but not limited to endoscopic instruments) can be coated with the polymer of the present invention to improve the surface properties of the article, specific surgical articles include surgical sutures, stents, and needles. For example the surgical article can be a suture, which can be attached to a needle. The suture can be a synthetic absorbable suture. These sutures are derived, for example, from homopolymers and copolymers of lactone monomers such as glycolide, lactide, ε-caprolactone, 1,4-dioxanone, and trimethylene carbonate. The suture can be a braided multifilament suture composed of polyglycolide or poly(glycolide-co-lactide).

The amount of coating polymer to be applied on the surface of a braided suture can be readily determined empirically, and will depend on the particular copolymer and suture chosen. Ideally, the amount of coating copolymer applied to the surface of the suture may range from about 0.5-30 percent of the weight of the coated suture or from about 1.0-20 weight percent, or from 1-5 percent by weight. If the amount of coating on the suture were greater than about 30 weight percent, then it may increase the risk that the coating may flake off when the suture is passed through tissue Sutures coated with the polymers of the present invention are desirable because they have a more slippery feel, thus making it easier for the surgeon to slide a knot down the suture to the site of surgical trauma. In addition, the suture is more pliable, and therefore is easier for the surgeon to manipulate during use. These advantages are exhibited in comparison to sutures which do not have their surfaces coated with the polymer of the present invention.

When the article of the present invention is a metal stent, the amount of coating applied to the surface of the article is an amount which creates a layer with a thickness ranging, for example, between about 2-20 microns on the stent or about 4-8 microns. If the amount of coating on the stent were such that the thickness of the coating layer was greater than about 20 microns, or if the thickness was less than about 2 microns, then the desired performance of the stent as it is passed through tissue may not be achieved.

When the article of the present invention is a surgical needle, the amount of coating applied to the surface of the article is an amount which creates a layer with a thickness ranging, for example, between about 2-20 microns on the needle or about 4-8 microns. If the amount of coating on the needle were such that the thickness of the coating layer was greater than about 20 microns, or if the thickness was less than about 2 microns, then the desired performance of the needle as it is passed through tissue may not be achieved.

The polymers of the present invention can also be used as a pharmaceutical carrier in a drug delivery matrix. To form this matrix the polymer can be mixed with a therapeutic agent to form the matrix. There are a variety of different therapeutic agents, which can be used in conjunction with the polymers of the invention. In general, therapeutic agents which may be administered via the pharmaceutical compositions of the invention include, antiinfectives such as antibiotics and antiviral agents; analgesics and analgesic combinations; anorexics; antihelmintics; antiarthritics; antiasthmatic agents; anticonvulsants; antidepressants; antidiuretic agents; antidiarrheals; antihistamines; antiinflammatory agents; antimigraine preparations; antinauseants; antineoplastics; antiparkinsonism drugs; antipruritics; antipsychotics; antipyretics, antispasmodics; anticholinergics; sympathomimetics; xanthine derivatives; cardiovascular preparations including calcium channel blockers and beta-blockers such as pindolol and antiarrhythmics; antihypertensives; diuretics; vasodilators including general coronary, peripheral and cerebral; central nervous system stimulants; cough and cold preparations, including decongestants; hormones such as estradiol and other steroids, including corticosteroids; hypnotics; immunosuppressives; muscle relaxants; parasympatholytics; psychostimulants; sedatives; and tranquilizers; and naturally derived or genetically engineered proteins, polysaccharides, glycoproteins, or lipoproteins.

The drug delivery matrix may be administered in any suitable dosage form including orally, parenterally, subcutaneously as an implant, vaginally, or as a suppository. Matrix formulations containing the polymers of the present invention may be formulated by mixing one or more therapeutic agents with the polymer. The therapeutic agent, may be present as a liquid, a finely divided solid, or any other appropriate physical form. Typically, but optionally, the matrix will include one or more additives, e.g., nontoxic auxiliary substances such as diluents, carriers, excipients, or stabilizers. Other suitable additives may be formulated with the polymers of the present invention and pharmaceutically active agent. If water is to be used, then it can be useful to add it just before administration.

The amount of therapeutic agent will be dependent upon the particular drug employed and medical condition being treated. Typically, the amount of drug represents about 0.001%-70%, 0.001%-50%, or 0.001%-20% by weight of the matrix.

The quantity and type of polymer incorporated into a composition (e.g., parenterally delivered composition) will vary depending on the release profile desired and the amount of drug employed. The product may contain blends of polymers of the present invention to provide the desired release profile or consistency to a given formulation.

The polymers of the present invention, upon contact with body fluids including blood or the like, undergoes gradual degradation (mainly through hydrolysis) with concomitant release of the dispersed drug for a sustained or extended period (as compared to the release from an isotonic saline solution). This can result in prolonged delivery (e.g., over 1-2,000 hours or 2-800 hours) of effective amounts (e.g., 0.0001 mg/kg/hour to 10 mg/kg/hour) of the drug. This dosage form can be administered as is necessary depending on the subject being treated, the severity of the affliction, and the judgment of the prescribing physician.

Individual formulations of drugs and polymers of the present invention may be tested in appropriate in vitro and in vivo models to achieve the desired drug release profiles. For example, a drug could be formulated with a polymer of the present invention and orally administered to an animal. The drug release profile could then be monitored by appropriate means such as, by taking blood samples at specific times and assaying the samples for drug concentration. Following this or similar procedures, those skilled in the art will be able to formulate a variety of formulations.

Functionalization

The functionalized phenolic compounds of the present invention are typically prepared from a starting phenolic compound as shown below.

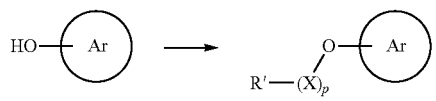

The desired X group(s) can be added using methods known to those of skill in the art, some of which are described below.

Glycolic acid and lactic acid are also known as alpha hydroxy acids (AHA) present in fruits and other foods. These acids are present in many healthiest foods we eat and drink, and they are considered to be safe when used correctly. Glycolic acid occurs naturally as the chief acidic constituent of sugar cane juice and occurs in beet juice and unripe grapes. Its formula is $HOCH_2COOH$ and is biodegradable. When glycolic acid is heated it readily loses water by self-esterification to form polyglycolic acid. Glycolic acid can function as both an acid and an alcohol. The process of attaching a glycolic acid moiety to the phenolic compound is defined as glycolation and will be referred to as such in describing this invention:

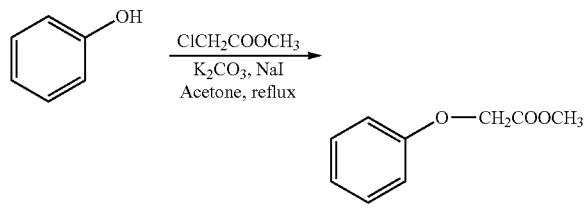

Lactic acid is a fermentation product of lactose. Lactic acid is produced commercially for use in foods and pharmaceuticals. Many surgical and orthopedic devices are made from polylactic acid. The process of attaching a lactic acid moiety to the phenolic compound is defined as lactolation and will be referred to as such in describing this invention:

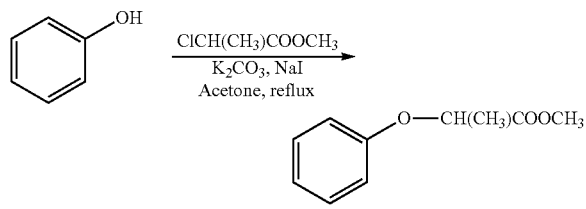

ε-Caprolactone is a cyclic monomer and is reactive, and the polymers derived are useful for tailoring specialty polyols and hydroxy-functional polymer resins with enhanced flexibility. The monomer polymerizes under mild conditions to give low viscosity products superior to conventional aliphatic polyesters. Copolymers of caprolactone with glycolide and lactide exhibit unique physical and biological properties as well as different hydrolysis profiles based on the composition of the monomers. The process of attaching an open chain ε-caprolactone moiety to the phenolic compound is defined as caprolation and will be referred to as such in describing this invention:

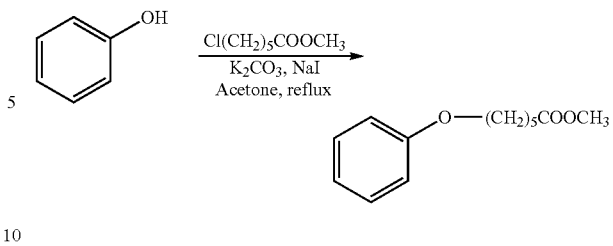

p-Dioxanone (1,4-dioxan-2-one) is a cyclic monomer and polymers are made via ring opening polymerization. Polyesters derived from this monomer are used in making absorbable surgical devices with longer absorption profile (slower hydrolysis) compare to polyglycolic acid. The absorbable surgical devices made from 1,4-dioxan-2-one are proved to be biologically safe, and biocompatible. The process of attaching an open chain p-dioxanone moiety (dioxanone) to the phenolic compound is defined as dioxonation and will be referred to as such in describing this invention:

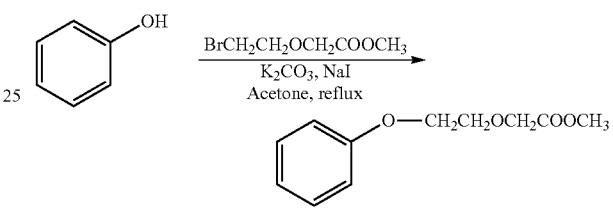

Many examples of both the phenolic compounds and the functionalization moieties have been shown to be safe and biocompatible. The new functionalized phenolics can have controllable hydrolysis profiles, improved bioavailability, improved efficacy and enhanced functionality. The difunctional compounds can readily polymerize into biodegradable polyesters, polyester amides, polyurethanes, polydiamides, and polyanhydrides, for example, useful for many applications, including biomedical applications, foodstuffs, nutritional supplements, cosmetics, medicaments, coatings and others readily apparent to one skilled in the art.

An object of this invention is to combine these molecules, such as glycolic acid, lactic acid, p-dioxanone, ε-caprolactone, —$(CH_2)_yCOO$—, where y is one of the integers 2, 3, 4 and between 6 and 24 inclusive, and —$(CH_2CH_2O)_zCH_2COO$—, where z is an integer between 2 and 24 inclusive, with phenolic compound, to form a new chemical entity. Preferential examples of functionalization molecules are glycolic acid, lactic acid, p-dioxanone, and ε-caprolactone. This functionalization enhances the native value of the phenolic compound by releasing the phenolic moiety by hydrolysis or degradation of the compound. The compound degrades under controllable conditions in the environment, in the body of an animal, for example a mammalian, including a human.

The glycolic acid moiety, lactic acid moiety, dioxanone moiety, caprolactone moiety, moieties of —$(CH_2)_yCOO$— where y is one of the numbers 2, 3, 4 and 6-24, and moieties of —$(CH_2CH_2O)_zCH_2COO$— where z is an integer between 2 and 24, including 2 and 24, have different hydrolysis or degradation rates and times over which they release the active phenolic moiety and thus do the functionalized phenolic acid made from them. The species used for functionalization supplies the release time or range dictated by the application. Glycolic acid based compounds hydrolyze faster than p-dioxanone based, where as lactic acid and caprolactone based compounds take much longer to hydrolyze than glycolic acid and p-dioxanone based compounds. This desired time range may be obtained by using a combination of functionalized phenolic compounds, that is, a blend of two or more functionalized compounds made from any two or more of the species glycolide, lactide, dioxanone and polydioxanone combined with one phenolic compound.

One aspect of the present invention combines the phenolic compound with one or more of the selected group of compounds to form a functionalized phenolic compound with uses in medicine, as enhanced drugs, drug intermediates, cancer preventing agents, nutrition supplements, nutriceuticals, antioxidants, controlled release preparations, cosmetic applications, flavors, coatings, drug intermediates, solvents for drugs, new monomers for polymerization, and when polymerized, as polymers for biomedical applications, drugs, nutrition supplements, nutriceuticals, drug delivery, cosmetic applications, flavors, and coatings.

The array of functionalized phenolic compounds developed as an aspect of the invention, have a wide range of hydrolysis rates that are controllable. The specific moiety or combination of moieties used for functionalization yields a compound or mixture with specific hydrolysis ranges.

The new functionalized phenolic compounds have more controllable hydrolysis profiles, improved bioavailability, improved efficacy and enhanced functionality. The difunctional compounds polymerize into biodegradable polymers, for example, useful for applications, including biomedical applications, foodstuffs, cosmetics, medicaments, coatings and other uses readily apparent to one skilled in the art.

The functionalized phenolics can be prepared according to any recognized method, but the Williamson ether synthesis method is the preferred method.

Synthesis

Preparation of ethers is an important reaction for which a wide variety of procedures have been developed during the last 100 years. The most commonly used method for the preparation of symmetrical and unsymmetrical ethers is the Williamson synthesis, involving a halide and an alkoxide. It is possible to mix the halide and alcohol with solid KOH and DMSO. The reaction involves an SN2 reaction in which an alkoxide ion replaces a halogen, sulfonyl, or a sulfate group. Usually, alkyl halides are used. The alkoxide can be prepared by the reaction of the corresponding alcohol with an active metal such as metallic sodium or a metal hydride like NaH acting upon the alcohol. The resulting alkoxide salt is then reacted with the alkyl halide (sulfonate or sulfate) to produce the ether in an SN2 reaction.

Recently several new procedures for Williamson synthesis have developed in which the phase transfer catalysis (PTC) appear to very convenient and the reactions can be run under mild conditions with high yields. Most recently, it was reported that ethers could be prepared directly from alcohol and alkyl halides under microwave irradiation in the presence of a quaternary ammonium salt.

For the synthesis of aromatic ethers, the phenolic compound was reacted with one member of the group Na metal, NaH, and potassium carbonate to form a phenoxide and then reacted with an alkyl halide to form an aromatic ether as shown below:

The first step of the Williamson ether synthesis is the reaction of sodium hydride with a phenolic compound. Phenols are more acidic than alkanols because of resonance stabilization of the conjugated anion.

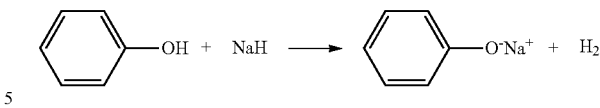

The resulting phenoxide ion is a powerful nucleophile, and reacts well with alkyl halide to form an ether.

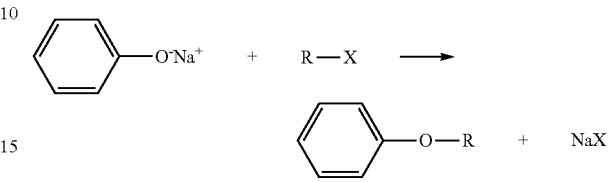

The alkyl halide should be primary so that the backside attack is not sterically hindered. When it is not primary, elimination usually results.

The general procedure for functionalizing phenolic compounds: To a mixture of phenolic compound, anhydrous potassium carbonate, sodium iodide and disodium phosphate in anhydrous acetone, while refluxing, the alkyl halide is added and refluxed for a period of from a few hours to several days until the reaction is essentially complete. Then the acetone is distilled off, water is added, and crude product is filtered and recrystallized from a solvent or mixture of solvents. Some times the products are purified by column chromatography. Solvent systems, reaction conditions, and purification methods are modified based on the phenol compound.

The process of preparing a phenolic ester with glycolic acid is shown below:

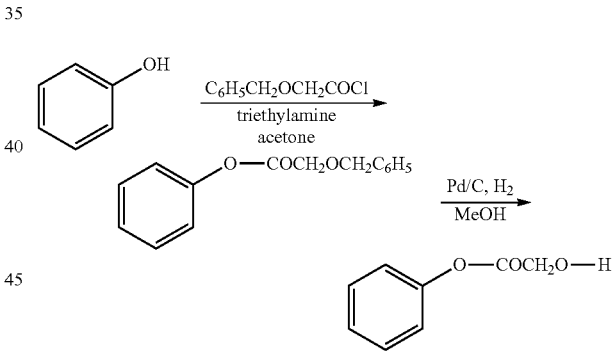

Benzyloxy acetyl chloride ($C_6H_5CH_2OCH_2COCl$) can be prepared as described in the following reaction scheme:

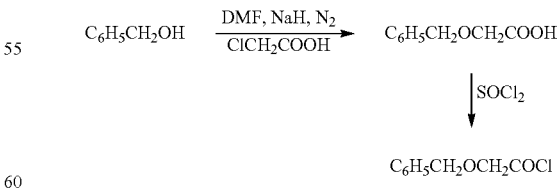

Using a similar method, $C_6H_5CH_2OCH(CH_3)COCl$, $C_6H_5CH_2O(CH_2)_5COCl$, and $C_6H_5CH_2OCH_2CH_2OCH_2COCl$ were synthesized for preparation of phenolic esters.

Lactic acid can function as both an acid and an alcohol. This dual functionality leads to a variety of chemical reactions and valuable physical properties. The process of preparing a phenolic ester with lactic acid is shown below:

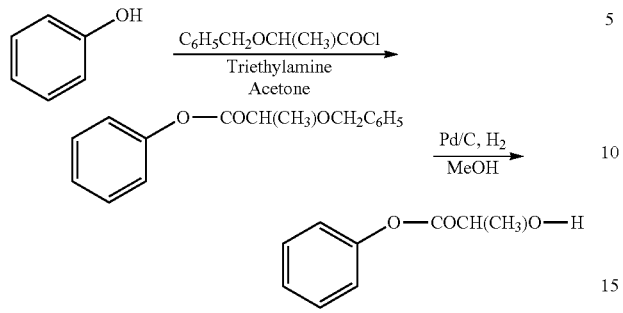

ε-Caprolactone, can function as both an acid and an alcohol. This dual functionality leads to a variety of chemical reactions and valuable physical properties. The process of preparing a phenolic ester with ε-caprolactone is shown below:

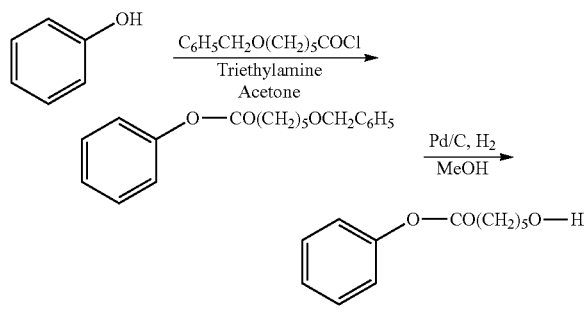

p-Dioxanone can function as both an acid and an alcohol. This dual functionality leads to a variety of chemical reactions and valuable physical properties. The process of preparing a phenolic ester with p-dioxanone is shown below:

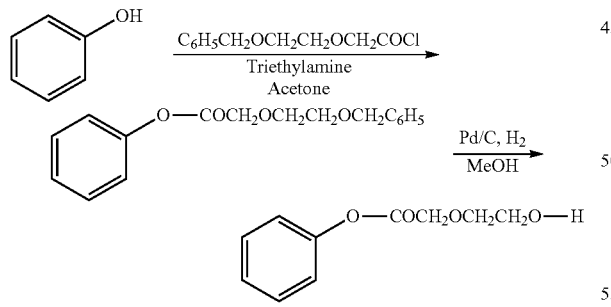

Synthesis of Phenolic Amides:

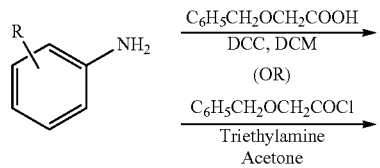

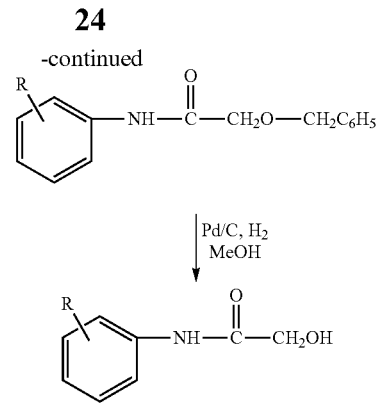

Benzyloxyamides are prepared by reacting benzyloxy acetic acid with an amine using dicyclohexylcarbodiimide (DCC) as coupling agent, in dichloromethane (DCM) as a solvent. The amine is dissolved in DCM and benzyloxyacetic acid is added. While maintaining below room temperature, DCC solution in DCM is added dropwise. The reaction generally proceeds cleanly for the formation of an amide. The urea formed is not soluble in DCM, and the urea can be filtered off to get the amide. In a second method the amines are reacted with the acid chloride directly using a base, such as $K_2CO_3$, $NaHCO_3$ or triethyl amine to neutralize the HCl that is formed during the reaction. Acetone is a good solvent for this reaction. Both methods are suitable for preparing benzyloxyamides.

Synthesis of Phenolic Esters:

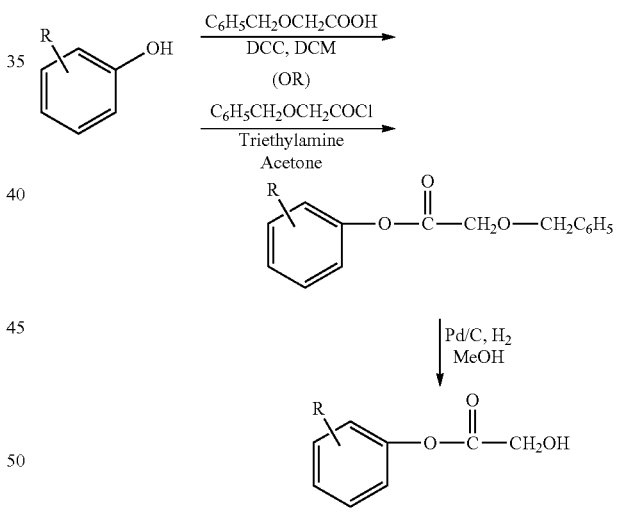

Conditions similar to those listed above can be used for preparing benzyloxyesters.

Debenzylation

Debenzylations were done using 50% wet Pd/C (5%) with H pressure up to 4 kg. MeOH or DMF can be as solvents. Dry Pd/C (5%) can be also used to avoid any moisture to avoid ester hydrolysis. DMF, MeOH, or Ethyl acetate can be used for this reaction.

Biodegradable Chewing Gums

After conventional chewing gum is chewed, the gum cud that remains that must be discarded. Unfortunately, conventional gum cuds can easily adhere to any dry surface, such as wood, concrete, paper and cloth. When gum cuds are improperly discarded, they can be difficult to remove from such surfaces, causing some environmental concerns. Recently, there has been a move to develop a chewing gum which is either ingestible or that creates a gum cud that is easily removable and degradable. Therefore, one of the objects of the present invention is to develop hydrolyzable and flexible elastomers that can be used in conventional and specialized biomedical chewing gum. Some of the compositions of the present invention can provide improved chewing gum and gum bases. The improved chewing gum and gum bases are biodegradable and do not cause environmental concerns if improperly discarded.

Bioactive Formulations

In other aspects of the present invention some functionalized phenolic compounds of the present invention are further manufactured into formulations suitable for oral, rectal, parenteral (for example, subcutaneous, intramuscular, intradermal, or intravenous), transdermal, vitreal or topical administration. The most suitable route in any given case will depend on the nature and severity of the condition being treated and on the nature of the particular active compound that is being used. The formulations of a pharmaceutical composition are typically admixed with one or more pharmaceutically or veterinarially acceptable carriers and/or excipients as are well known in the art.

Formulations suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion.

Compositions of the present invention suitable for parenteral administration conveniently comprise sterile aqueous preparations of the active compounds, which preparations are preferably isotonic with the blood of the intended recipient.

Formulations suitable for rectal administration are preferably presented as unit dose suppositories.

Formulations suitable for ocular or vitreal administration may be presented as bioabsorbable coatings for implantable medical devices, injectables, liquids, gels or suspensions.

Formulations or compositions suitable for topical administration to the skin preferably take the form of an ointment, cream, lotion, paste, gel, spray, aerosol, or oil. Examples of carriers that conventionally used include Vaseline, lanoline, polyethylene glycols, alcohols, and combination of two or more thereof.

Formulations suitable for transdermal administration may be presented as discrete patches adapted to remain in intimate contact with the epidermis of the recipient for a prolonged period of time.

The active compounds may be provided in the form of foodstuffs or nutrition supplements, such as being added to, admixed into, coated, combined or otherwise added to a foodstuff. The term foodstuff is used in its widest possible sense and includes liquid formulations such as drinks including dairy products, biodegradable chewing gums, and other foods, such as health bars, desserts, etc. Food formulations containing compounds of the invention can be readily prepared according to standard practices.

Compounds of the formula used as medicaments or pharmaceuticals are typically administered in a manner and amount as is conventionally practiced. See, for example, Goodman and Gilman, *The Pharmaceutical Basis of Therapeutics*, current edition.

Compounds of the present invention have potent antioxidant activity and increased acidity of their phenolic component, as well as the improved biodegradation provided by the functionalization, and thus find wide application in pharmaceutical and veterinary uses, in cosmetics such as more effective skin creams to prevent skin ageing, in sun screens, in foods, health drinks, nutritional supplements, shampoos, and the like.

Examples of functionalized phenolic compounds of the present invention are provided for some embodiments of the current invention. It can be extended to other species. This selection is not meant to limit the scope of the invention in any way. Other variations in the procedure may be readily apparent to those skilled in the art.

EXAMPLE 1

4-Methoxycarbonylmethoxy-benzoic acid methyl ester (1)

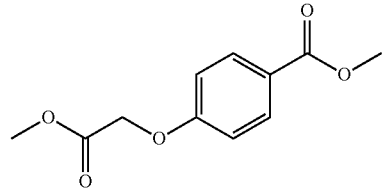

To a refluxing mixture of methyl 4-hydroxy benzoate (152 grams, 1 mol) and Methyl chloro acetate (136.2 grams, 1.255 mol) in anhydrous methanol (450 mL) under nitrogen was added 30% sodium methoxide solution in methanol (180 mL, 1 mol) drop wise over a period of 2 hours. Further refluxed for 16 hours, cooled to 5°, filtered, dried and recrystallized from methanol to give pure 1 (157 grams, 70%) as a white shining powder.

The melting point was measured for all the products by using Polmon (MP 96) melting point apparatus, and the melting point found to be 92.2-93.8° C. For all the products IR was run using Perkin Elmer FTIR Spectrophotometer, Model: Spectrum RXI FTIR. The I.R of this confirms the structure. For all the products, NMR was run using Varian 200 MHz and tetramethyl-silane as the internal standard. The structure was confirmed by NMR. $^1$HNMR (CDCl$_3$) δ 3.82 (s,3H,Ester), 3.88(s, 3H, Ester), 4.68(s,2H,OCH$_2$), 6.91(dd,2H,Ar), 7.98 (dd,2H,Ar).

EXAMPLE 2

4-(1-Methoxycarbonyl-ethoxy)-benzoic acid methyl ester (2)

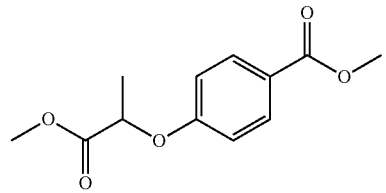

To a mixture of methyl 4-hydroxy benzoate (75 grams, 493 mmol), anhydrous K$_2$CO$_3$ (270 grams, 1.954 mol) and Sodium iodide (5 grams, 33.3 mmol) in anhydrous acetone (1400 mL) was added methyl 2-chloro propionate (90.3 grams, 737 mmol) and refluxed for 24 hours. Acetone was distilled and water (1000 mL) was added. Crude 2 was extracted into Ethyl acetate, dried over Na$_2$SO$_4$, distilled and purified by column chromatography on silica gel using Hexane to give pure 2 (45 grams, 38.5%) as a pale yellow syrup. The structure was confirmed by NMR. $^I$HNMR (CDCl$_3$) δ 1.65(d,3H,CH$_3$), 3.77 (s, 3H, Ester), 3.88(s, 3H, Ester), 4.34 (q,1H,CH), 6.88(d,2H,Ar), 7.98 (d, 2H,Ar).

EXAMPLE 3

4-(5-Methoxycarbonyl-pentyloxy)-benzoic acid methyl ester (3)

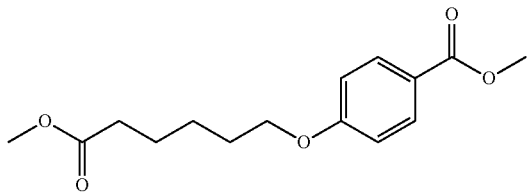

To a refluxing mixture of methyl 4-Hydroxy benzoate (25 grams, 164 mmol), and anhydrous K$_2$CO$_3$ (62.5 grams, 452 mmol) in anhydrous acetone (300 mL) was added methyl 6-bromo hexanoate (42.5 grams, 203 mmol) and refluxed for 48 hours. Acetone was distilled and water (300 mL) was added. Crude 3 was filtered dried and recrystallized from methanol to give pure 3 (33 grams, 72%) as a white powder. The melting was found to be 42.5-44.5° C. The structure was confirmed by NMR. $^I$HNMR (CDCl$_3$) δ 1.54 (m, 2H, CH$_2$), 1.71(m, 2H, CH$_2$), 1.84(m, 2H, CH$_2$), 2.36 (t, 2H,CH$_2$) 3.68 (s,3H,Ester), 3.88 (s, 3H,Ester), 4.05(t,2H,OCH$_2$), 6.88(d, 2H,Ar), 7.94(d,2H,Ar).

EXAMPLE 4

4-(2-Methoxycarbonylmethoxy-ethoxy)-benzoic acid methyl ester (4)

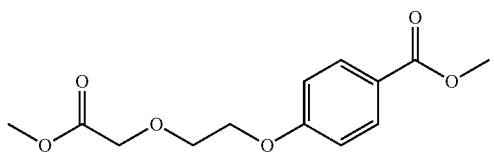

To a mixture of methyl 4-hydroxy benzoate (10 grams, 66 mmol), anhydrous K$_2$CO$_3$ (21 grams, 152 mmol) Sodium iodide (3 grams, 20 mmol) in anhydrous acetone (100 mL) was added (2-Bromoethoxy) acetic acid methyl ester (21 grams, 106 mmol) and refluxed for 24 hours. Acetone was distilled and water (100 mL) was added. Crude 4 extracted into ethyl acetate, distill off Ethyl acetate and purified by column chromatography on silica gel using Hexane:Ethyl acetate (9:1) as eluant to give pure 4 as a white powder. The melting was found to be 66-62.5° C. The structure was confirmed by NMR. $^I$HNMR (CDCl$_3$) δ 3.72 (s, 3H,ester), 3.88 (s, 3H ester), 3.92(t, 2H,CH$_2$)4.20 (s, 2H,CH$_2$), 4.22(t,2H, CH$_2$), 6.90(d,2H Ar), 7.94(d, 2H,Ar).

EXAMPLE 5

2-Methoxycarbonylmethoxy-benzoic acid methyl ester (5)

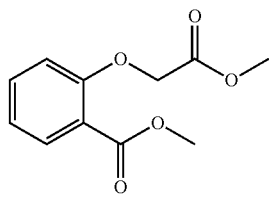 [SMILES: COC(=O)COc1ccccc1C(=O)OC]

To a mixture of methyl salicylate (100 grams, 657 mmol), anhydrous K$_2$CO$_3$ (360 grams, 2.605 mol) in anhydrous acetone (1000 mL) was added methyl chloro acetate (94 grams, 866 mmol) and refluxed for 36 hours. Acetone was distilled and water (1200 mL) was added. Crude 5 was extracted into Chloroform, dried over Na$_2$SO$_4$ distilled and purified by column chromatography on silica gel using Hexane as eluant to give pure 5 (25 grams, 17%) as a light yellow syrup. The structure was confirmed by NMR. $^I$HNMR (CDCl$_3$) δ 3.79(s, 3H,ester), 3.88(s,3H,ester), 4.70(s,2H,OCH$_2$), 6.88(dd,1H, Ar), 7.03 (m,1H,Ar), 7.42(m,1H,Ar), 7.81 (dd,1H,Ar).

EXAMPLE 6

2-(1-Methoxycarbonyl-ethoxy)-benzoic acid methyl ester (6)

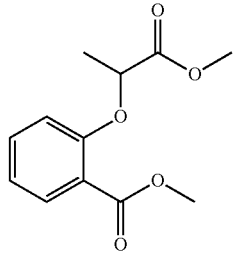 [SMILES: COC(=O)c1ccccc1OC(C)C(=O)OC]

To a mixture of methyl salicylate (100 grams, 657 mmol), anhydrous K$_2$CO$_3$ (360 grams, 2.605 mol) and Sodium iodide (5 grams, 33.3 mmol) in anhydrous acetone (1000 mL) was added methyl 2-chloro propionate (104 grams, 849 mmol) and refluxed for 48 hours. Acetone was distilled and water (1200 mL) was added. Crude 6 was extracted into Ethyl acetate, dried over Na$_2$SO$_4$, distilled and purified by column chromatography on silica gel using Hexane as eluant to give pure 6 (35 grams, 22.4%) as a light yellow syrup. The structure was confirmed by NMR. $^I$HNMR (CDCl$_3$) δ 1.58(d, 3H,CH$_3$), 3.65(s,3H,ester), 3.82(s,3H,ester), 4.72(q,1H,CH), 6.78 (d,1H,Ar), 6.85(m,1H,Ar), 7.32(m,1H,Ar), 7.74(d,1H Ar).

EXAMPLE 7

2-(5-Methoxycarbonyl-pentyloxy)-benzoic acid methyl ester

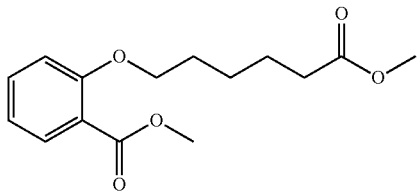 [SMILES: COC(=O)CCCCCOc1ccccc1C(=O)OC]

To a mixture of methyl salicylate (50 grams, 329 mmol), anhydrous K$_2$CO$_3$ (180 grams, 1.30 mol) and Sodium iodide (5 grams, 33.3 mmol) in anhydrous acetone (600 mL) was added methyl 6-bromo Hexanoate (76 grams, 364 mmol) and refluxed for 40 hours. Acetone was distilled and water (750 mL) was added. Crude 7 was extracted into Ethyl acetate, dried over Na$_2$SO$_4$, distilled and purified by column chromatography on silica gel using Hexane as eluant to give pure 7 (55 grams, 60%) as a light yellow syrup. The structure was confirmed by NMR. The structure was confirmed by NMR. $^I$HNMR (CDCl$_3$) δ 1.60(m, 2H,CH$_2$), 1.72(m, 2H,CH$_2$), 1.77 (m, 2H,CH$_2$), 2.35(t, 2H,CH$_2$), 3.66 (s,3H,ester), 3.88(s,3H, ester), 4.02(t,2H, OCH$_2$), 6.90(m,2H,Ar), 7.38(m,1H,Ar), 7.74(d,1H,Ar).

EXAMPLE 8

3-Methoxy-4-methoxycarbonylmethoxy-benzoic acid ethyl ester (8)

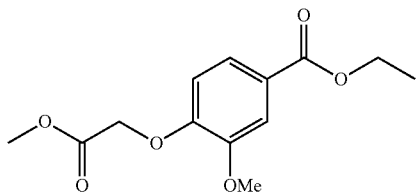 [SMILES: CCOC(=O)c1ccc(OCC(=O)OC)c(OC)c1]

To a mixture of Ethyl Vanillate (100 grams, 510 mmol), and anhydrous K$_2$CO$_3$ (300 grams, 2.17 mol) in anhydrous acetone (1000 mL) was added methyl chloro acetate (123.8 grams, 1.14 mmol) and refluxed for 8 hours. Acetone was distilled and water (1500 mL) was added. Crude 8 was filtered, dried, and recrystallized from a mixture of toluene: Hexane (1:5) to give pure 8 (95.7 grams, 70%) as a white powder. The melting point was found to be 72.7-74.3° C. The structure was confirmed by I.R and NMR. $^I$HNMR (CDCl$_3$) δ 1.40 (t, 3H,CH$_2$CH$_3$), 3.80(s, 3H, Ester), 3.92(s, 3H,OCH$_2$), 4.38 (q, 2H,OCH$_2$CH$_3$), 4.88(s,2H,OCH$_2$), 6.80(d, 1H,Ar), 7.59(d,1H,Ar), 7.66(dd,1H,Ar).

EXAMPLE 9

3-Methoxy-4-(5-methoxycarbonyl-pentyloxy)-benzoic acid ethyl ester (9)

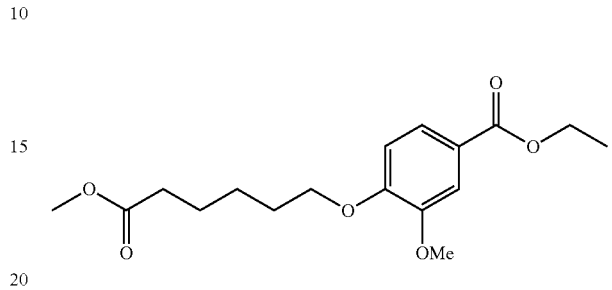

To a mixture of Ethyl vanillate (40 grams, 204 mmol), anhydrous K$_2$CO$_3$ (120 grams, 868 mmol) in anhydrous acetone (750 mL) was added methyl 6-bromo hexanoate (56 grams, 268 mmol) and refluxed for 6 hours. Acetone was distilled and water (600 mL) was added. Crude 9 was filtered, dried, and recrystallized from a mixture of Toluene:Hexane (1:6) to give pure 9 (46 grams, 96.6%) as a white powder. The melting point was found to be 42.5-43.5° C. The structure was confirmed by I.R and NMR. $^I$HNMR (CDCl$_3$) δ 1.38 (t, 3H,—OCH$_2$CH$_3$), 1.52(m, 2H, CH$_2$), 1.69(m, 2H,CH$_2$), 1.85 (m, 2H, CH$_2$), 2.32(t, 2H, CH$_2$), 3.62(s, 2H, OCH$_3$), 3.84(s, 2H, Ester), 4.02(t, 2H, —OCH$_2$), 4.34(q, 2H,—OCH$_2$CH$_3$), 6.83(d, 1H, Ar), 7.28(dd,1H,Ar), 7.58(dd,1H,Ar).

EXAMPLE 10

2,5-Bis-methoxycarbonylmethoxy-benzoic acid methyl ester (10)

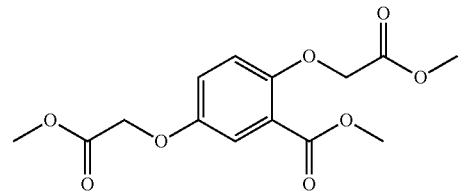

To a mixture of methyl 2,5-dihydroxy-benzoate (34 grams, 202 mmol), and anhydrous K$_2$CO$_3$ (204 grams, 1.476 mol), Sodium iodide (5 grams, 33.3 mmol) in anhydrous acetone (1000 mL) was added methyl chloro acetate (60.7 grams, 559 mmol) and refluxed for 20 hours. Acetone was distilled and water (1500 mL) was added. Crude 10 was filtered dried and recrystallized from Toluene to give pure 10 (50.5 grams, 80%) as a cream color powder. The melting point was found to be 90-94° C. The structure was confirmed by NMR. $^I$HNMR (CDCl$_3$) δ 3.78 (s, 3H,Ester), 3.80(s, 3H,Ester), 3.89

(s, 3H,Ester), 4.59 (s, 2H,OCH$_2$), 4.63(s, 2H,OCH$_2$), 6.88 (d, 1H,Ar), 7.02(dd,1H,Ar), 7.32(d,1H,Ar).

EXAMPLE 11

4-Ethoxycarbonylmethoxy-3,5-dimethoxy-benzoic acid methyl ester (11)

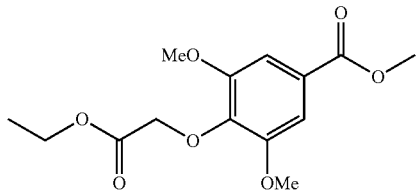 [SMILES: CCOC(=O)COc1c(OC)cc(C(=O)OC)cc1OC]

To a mixture of methyl syringate (100 grams, 472 mmol), anhydrous K$_2$CO$_3$ (250 grams, 1.809 mol) in anhydrous acetone (1200 mL) was added Ethyl bromo acetate (113 grams, 677 mmol) and refluxed for 48 hours. Acetone was distilled and water (1200 mL) was added. Crude 11 was filtered, dried, and recrystallized from toluene to give pure 11 (105 grams, 75%) as a white powder. The melting point was found to be 90.5-92.5° C. The structure was confirmed by I.R and NMR. $^1$HNMR (CDCl$_3$) δ 1.32 (t, 3H,CH$_2$CH$_3$), 3.88(s, 3H,Ester), 3.90(s, 6H,OCH$_3$), 4.25 (q, 2H,CH$_2$CH$_3$), 4.69(s, 2H,OCH$_2$), 7.24 (s, 2H,Ar).

EXAMPLE 12

(4-Methoxycarbonylmethoxy-phenyl)-acetic acid methyl ester (12)

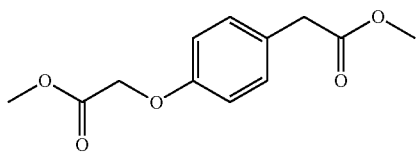

To a mixture of methyl 4-Hydroxy phenyl acetate (100 grams, 602 mmol), anhydrous K$_2$CO$_3$ (260 grams, 1.88 mol), Sodium iodide (21 grams, 140 mmol) in anhydrous acetone (1500 mL) was added methyl chloro acetate (75 grams, 691 mmol) and refluxed for 8 hours. Acetone was distilled and water (1200 mL) was added. Crude 12 was extracted into Ethyl acetate, dried over Na$_2$SO$_4$, distilled and purified by column chromatography on silica gel using benzene as eluant to give pure 12 (65 grams, 45.4%) as a white power. The melting point was found to be 52.5-55.4° C. The purity by HPLC was determined by using Waters 515 HPLC, and found to be 98.5%. The structure was confirmed by NMR. $^1$HNMR (CDCl$_3$) δ 3.52 (s, 2H,CH$_2$), 3.68(s,3H,ester), 3.78(s,3H,ester), 4.60(s,2H,OCH$_2$), 6.80(d,2H,Ar), 7.16 (d,2H,Ar).

EXAMPLE 13

2-(4-Methoxycarbonylmethyl-phenoxy)-propionic acid methyl ester (13)

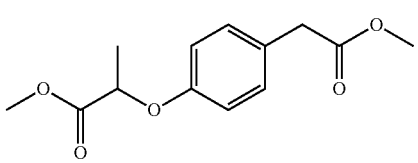

To a mixture of methyl 4-hydroxy phenyl acetate (100 grams, 602 mmol), anhydrous K$_2$CO$_3$ (260 grams, 1.88 mol), Sodium iodide (12 grams, 80 mmol) in anhydrous acetone (1500 mL) was added methyl 2-chloro propionate (90.3 grams, 737 mmol) and refluxed for 8 hours. Acetone was distilled and water (1200 mL) was added. Crude 13 was extracted into Ethyl acetate, dried over Na$_2$SO$_4$, distilled and purified by column chromatography on silica gel using Hexane as eluant to give pure 13 (100 grams, 66%) as a low melting solid. The purity was found to be 99.1% by HPLC. The structure was confirmed by NMR. $^1$HNMR (CDCl$_3$) δ 1.62 (d, 3H,CH$_3$), 3.55(s,2H,CH$_2$), 3.68(s,3H,ester), 3.75(s, 3H,ester), 4.75(q,1H,CH), 6.82 (d,2H,Ar), 7.16(d,2H,Ar).

EXAMPLE 14

6-(4-Methoxycarbonylmethyl-phenoxy)-hexanoic acid methyl ester (14)

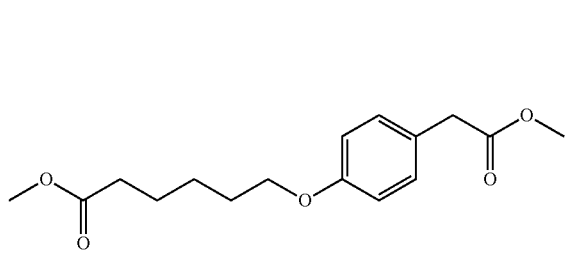

To a mixture of methyl 4-hydroxy phenyl acetate (125 grams, 752 mmol), anhydrous K$_2$CO$_3$ (325 grams, 2.352 mol) in anhydrous acetone (1500 mL) was added methyl 6-bromo hexanoate (203 grams, 971 mmol) and refluxed for 8 hours. Acetone was distilled and water (1500 mL) was added. Crude 14 was extracted into Ethyl acetate, dried over Na$_2$SO$_4$, distilled and purified by column chromatography on silica gel using Hexane as eluant to give pure 14 (125 grams, 56.6%) as a light yellow syrup. The structure was confirmed by NMR. $^1$HNMR (CDCl$_3$) δ 1.46 (m, 2H,CH$_2$), 1.70(m,2H,CH$_2$), 1.78

(m,2H,CH$_2$), 2.30(t,2H, CH$_2$), 3.48(s,2H,CH$_2$), 3.62 (s,6H, ester), 3.90(t,2H,OCH$_2$), 6.76(d,2H,Ar), 7.12(d,2H,Ar).

EXAMPLE 15

3-(4-Methoxycarbonylmethoxy-phenyl)-propionic acid methyl ester (15)

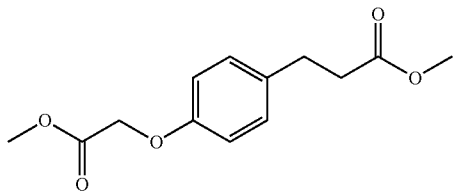

To a mixture of methyl 3(4-hydroxy phenyl)propionate (60 grams, 333 mmol), anhydrous K$_2$CO$_3$ (180 grams, 1.30 mol) in anhydrous acetone (1 liter) was added methyl chloro acetate (74.2 grams, 684 mmol) and refluxed for 40 hours. Acetone was distilled and water (1000 mL) was added. Crude 15 extracted into chloroform, distilled chloroform and high vacuum distilled to get pure 15 (30 grams, 36%) as a colorless low melting solid. Bp$_{12}$ 210-213° C. The structure was confirmed by NMR. $^I$HNMR (CDCl$_3$) δ 2.58 (t, 2H, CH$_2$), 2.90(t, 2H, CH$_2$), 3.62(s, 3H, ester), 3.80(s, 3H, ester), 4.60(s, 3H, OCH2), 6.80(d, 2H, Ar), 7.12(d, 2H, Ar).

EXAMPLE 16

3-(4-Methoxycarbonylmethoxy-phenyl)-acrylic acid methyl ester (16)

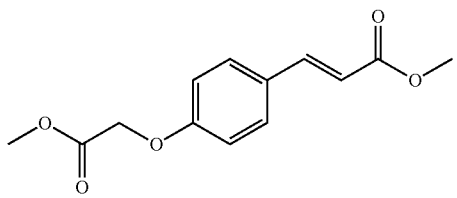

To a mixture of methyl 4-hydroxy cinnamale (20 grams, 112 mmol), anhydrous K$_2$CO$_3$ (48 grams, 347 mmol), Sodium iodide (2 grams, 13.3 mmol), disodium phosphate (2 grams, 14.2 mmol) in anhydrous acetone (200 mL) was added methyl chloro acetate (14.6 grams, 135 mmol) and refluxed for 8 hours. Acetone was distilled and water (200 mL) was added. Crude 16 was filtered, dried, and recrystallized from toluene to give pure 16 (20 grams, 71.4%) as a white shining powder. The melting point was found to be 107-108.8° C. The structure was confirmed by IR and NMR. $^I$HNMR (CDCl$_3$) δ 3.76(s, 3H, ester), 3.78 (s, 3H, Ester), 4.60(s, 2H,—OCH$_2$), 6.24(d, 1H, J=17.9 Hz, CH═CH), 6.84(dd, 2H, Ar), 7.44(dd, 2H,Ar), 7.56(d,1H,J=17.9 Hz, CH═CH).

EXAMPLE 17

3-(3,4-Bis-methoxycarbonylmethoxy-phenyl)-acrylic acid methyl ester (17)

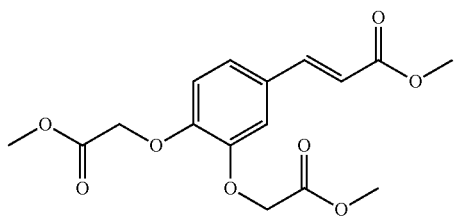

To a mixture of methyl caffiate (25 grams, 129 mmol), anhydrous K$_2$CO$_3$ (145 grams, 1.049 moles), Sodium iodide (10 grams, 67 mmol), disodium phosphate (10 grams, 71 mmol) in anhydrous acetone (750 mL) was added methyl chloro acetate (48.7 grams, 449 mmol) and refluxed for 20 hours. Acetone was distilled and water (1 liter) was added. Crude 17 was filtered, dried, and recrystallized from methanol to give pure 17 (27 grams, 62%) as a white powder. The melting point was found to be 120.2-123.1° C. The structure was confirmed by IR and NMR. $^I$HNMR (CDCl$_3$) δ 3.81 (s,9H,Ester), 4.75(s,4H,O—CH$_2$), 6.23(d, 1H, J=17.5 Hz, double bond) 6.80 (d,1H, Ar), 7.09(m, 2H, Ar), 7.59(d,1H, J=17.5 Hz, double bond).

EXAMPLE 18

3-[3,4-Bis-(1-methoxycarbonyl-ethoxy)-phenyl]-acrylic acid methyl ester (18)

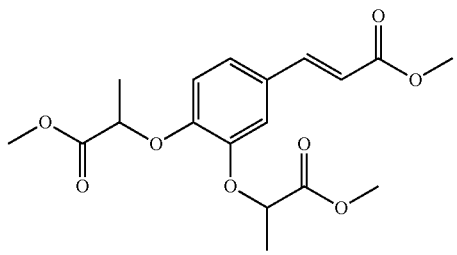

To a mixture of methyl caffiate (25 grams, 125 mmol), anhydrous K$_2$CO$_3$ (133 grams, 962 mmol), Sodium iodide (10 grams, 66.7 mmol), disodium phosphate (10 grams, 70.8 mmol) in anhydrous acetone (500 mL) was added methyl 2-chloro propionate (56 grams, 457 mmol) and refluxed for 100 hours. Acetone was distilled and water (750 mL) was added. Crude 18 was extracted into ethyl acetate, dried over Na$_2$SO$_4$, distilled and purified by column chromatography on silica gel using a mixture of Ethyl acetate:Hexane (1:9) to give pure 18 (25 grams, 53.2%) as a syrup.

EXAMPLE 19

6-[2-(5-Methoxycarbonyl-pentyloxy)-4-(2-methoxy-carbonyl-vinyl)-phenoxy]-hexanoic acid methyl ester (19)

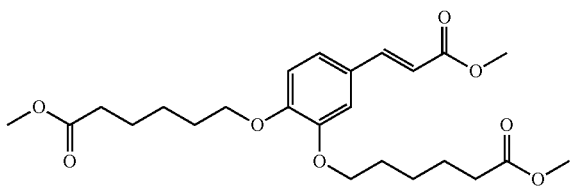

To a mixture of methyl caffiate (32 grams, 165 mmol), anhydrous K$_2$CO$_3$ (186 grams, 1.346 mol), Sodium iodide (13 grams, 87 mmol), disodium phosphate (13 grams, 92 mmol) in anhydrous acetone (100 mL) was added methyl 6-bromohexanoate (122 grams, 584 mmol) and refluxed for 8 hours. Acetone was distilled and water (1000 mL) was added. Crude 19 was filtered, dried, and recrystallized from chloroform to give pure 19 (52 grams, 72%) as a white powder. The melting point was found to be 57-60.8° C. The structure was confirmed by IR and NMR. $^1$HNMR (CDCl$_3$) δ 1.75 (m,12H,—CH$_2$—), 2.38(t,4H, —CH$_2$—), 3.69(s, 6H, ester) 3.80 (s,3H, Ester), 4.05(t, 4H, O—CH$_2$), 6.25(d,1H,J=16 Hz, CH═CH), 6.80(d,1H,Ar), 7.05 (m, 2H, Ar), 7.59 (d,1H,J=16 Hz, CH═CH).

EXAMPLE 20

3-(3-Methoxy-4-methoxycarbonylmethoxy-phenyl)-acrylic acid methyl ester (20)

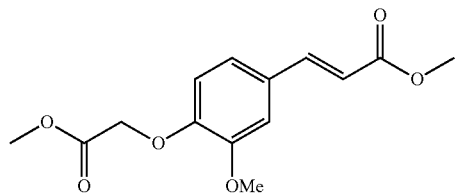

To a mixture of methyl ferulate (38 grams, 183 mmol), anhydrous K$_2$CO$_3$ (88 grams, 637 mmol), Sodium iodide (8 grams, 53 mmol), disodium phosphate (8 grams, 56 mmol) in anhydrous acetone (800 mL) was added methyl chloro acetate (27.2 grams, 251 mmol) and refluxed for 10 hours. Acetone was distilled and water (750 mL) was added. Crude 20 was filtered and recrystallized from methanol and further purified by column chromatography on silica gel using chloroform as eluant to give pure 20 (36 grams, 70.6%) as a white powder. The melting point found to be 105-106.8° C. The structure was confirmed with IR and NMR. $^1$HNMR (CDCl$_3$) δ 3.80 (s, 6H, ester), 3.92 (s, 3H, —OCH$_3$), 4.64 (s, 2H, O CH$_2$), 6.26 (d, 1H, J=17.5 Hz, CH═CH), 6.78 (d, 1H, Ar), 7.05 (m, 2H, Ar), 7.60 (d, 1H, J=17.5 Hz, CH═CH).

EXAMPLE 21

3-[3-Methoxy-4-(1-methoxycarbonyl-ethoxy)-phenyl]-acrylic acid methyl ester (21)

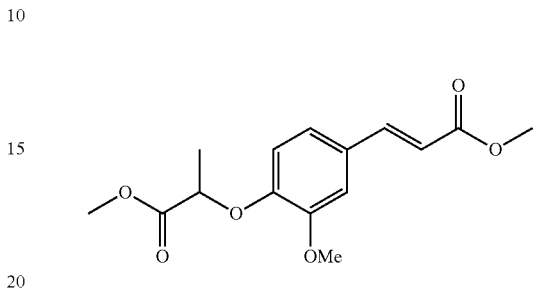

To a mixture of methyl ferulate (52 grams, 250 mmol), anhydrous K$_2$CO$_3$ (120 grams, 868 mmol), Sodium iodide (10.5 grams, 70 mmol), disodium phosphate (10.5 grams, 74 mmol) in anhydrous acetone (1040 mL) was added methyl 2-chloro propionate (42 grams, 343 mmol) and refluxed for 48 hours. Acetone was distilled and water (750 mL) was added. Crude 21 was extracted in to chloroform, dried over Na$_2$SO$_4$, distilled and the crude was recrystallized from a mixture of chloroform:hexane (1:6) to give pure 21 (40 grams, 54.4%) as a white powder. The melting point was found to be 69-70.7° C. The structure was confirmed with IR and NMR. $^1$HNMR (CDCl$_3$) δ 1.62 (d, 3H, CH$_3$), 3.66 (s, 3H, ester), 3.79 (s, 3H, —OCH$_3$), 3.86 (s, 3H, ester), 4.79 (q, 1H, OCH), 6.24 (d, 1H, J=16.9 Hz, —CH═CH), 6.75 (d,1H,Ar), 7.01 (m,2H, Ar), 7.55 (d, 1H, J=16.9 Hz, —CH═CH).

EXAMPLE 22

6-[2-Methoxy-4-(2-methoxycarbonyl-vinyl)-phenoxy]-hexanoic acid methyl ester (22)

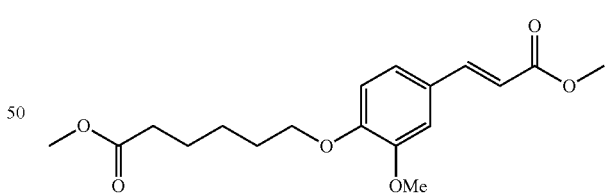

To a mixture of methyl ferulate (44 grams, 211 mmol), anhydrous K$_2$CO$_3$ (102 grams, 738 mmol), Sodium iodide (8.8 grams, 59 mmol), disodium phosphate (8.8 grams, 62 mmol) in anhydrous acetone (900 mL) was added methyl 6-bromo hexanoate (61 grams, 292 mmol) and refluxed for 16 hours. Acetone was distilled and water (600 mL) was added. Crude 22 was filtered, dried and recrystallized from methanol to give pure 22 (52 grams, 73.2%) as a white fluffy powder. The melting point was found to be 90-91.8° C. The structure was confirmed with IR and NMR. $^1$HNMR (CDCl$_3$) δ 1.53 (m, 2H,—CH$_2$—), 1.72(m, 2H, —CH2), 1.91(m, 2H, —CH$_2$—), 2.38 (q, 2H, CH$_2$), 3.65 (s, 3H, ester), 3.80 (s, 3H, —

OCH₃), 3.89 (s, 3H, ester), 6.30(d, 1H, J=17 Hz, C<u>H</u>=CH), 6.81 (d,1H,Ar), 7.02 (d,2H Ar), 7.12 (dd,1H,Ar), 7.62 (d, 1H, J=17 Hz, CH=C<u>H</u>).

EXAMPLE 23

3-(3,5-Dimethoxy-4-methoxycarbonylmethoxy-phenyl)-acrylic acid methyl ester (23)

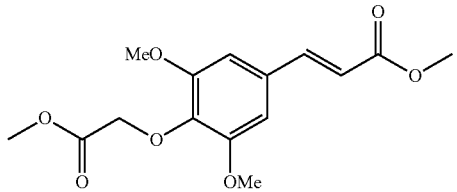

To a mixture of methyl sinapinate (40 grams, 168 mmol), anhydrous K₂CO₃ (80 grams, 579 mmol), Sodium iodide (10 grams, 66.7 mmol), disodium phosphate (10 grams, 70.62 mmol) in anhydrous acetone (1000 mL) was added methyl chloro acetate (20 grams, 224.5 mmol) and refluxed for 10 hours. Acetone was distilled and water (300 mL) was added. Crude 23 was filtered and purified by column chromatography on silica gel using chloroform to give pure 23 (21 grams, 40.3%) as a white powder. The melting point was found to be 90-93° C. The structure was confirmed with IR and NMR. ᴵHNMR (CDCl₃) δ 3.80(s, 6H, —O<u>CH₃</u>), 3.88(s, 6H, ester), 4.62 (s, 2H, O<u>CH₂</u>), 6.30(d, 1H, J=17.6 Hz, C<u>H</u>=CH), 6.73 (s, 2H, Ar), 7.58(d, 1H, J=17.6 Hz, CH=C<u>H</u>).

EXAMPLE 24

3-[3,5-Dimethoxy-4-(1-methoxycarbonyl-ethoxy)-phenyl]-acrylicacid methyl ester (24)

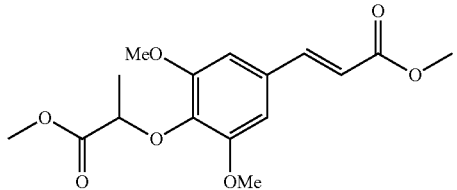

To a mixture of methyl sinapinate (20 grams, 84 mmol), anhydrous K₂CO₃ (40 grams, 289 mmol), Sodium iodide (2 grams, 13.3 mmol), disodium phosphate (5 grams, 35.4 mmol) in anhydrous acetone (500 mL) was added methyl 2-chloro propionate (15 grams, 122.8 mmol) and refluxed for 14 days. Acetone was distilled and water (200 mL) was added. Crude 24 was filtered and recrystallized from a mixture of chloroform:hexane (1:5) to give pure 24 (16 grams, 78.4%) as a white powder. The melting point was found to be 115.5-113° C. The structure was confirmed with IR and NMR. ᴵHNMR (CDCl₃) δ 1.58(d, 3H,—C<u>H₃</u>), 3.78(s, 3H, —O<u>CH₃</u>), 3.80(s, 3H, O<u>CH₃</u>), 3.82(s, 6H, ester), 3.84(s, 3H, ester), 4.73 (q, 1H, C<u>H</u>), 6.35(d, 1H, J=17.2 Hz, C<u>H</u>=CH), 6.75 (s, 2H, Ar), 7.60(d, 1H, J=17.2 Hz, CH=C<u>H</u>).

EXAMPLE 25

6-[2,6-Dimethoxy-4-(2-methoxy carbonyl-vinyl)-phenoxy]-hexanoic acid methyl ester (25)

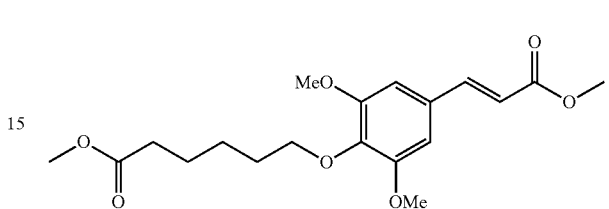

To a mixture of methyl sinapinate (30 grams, 126 mmol), anhydrous K₂CO₃ (69 grams, 499 mmol), Sodium iodide (7.5 grams, 50 mmol), disodium phosphate (15 grams, 106 mmol) in anhydrous acetone (300 mL) was added methyl 6-bromo hexanoate (33 grams, 158 mmol) and refluxed for 12 days. Acetone was distilled and water (300 mL) was added. Crude 25 was filtered and purified by column chromatography on silica gel using hexane:Ethyl acetate (99:1) to give pure 25 (4.5 grams, 9.7%) as a white powder. The melting point was found to be 87-89° C. The structure was confirmed with IR and NMR. ᴵHNMR (CDCl₃) δ 1.54(d, 2H,—C<u>H₂</u>), 1.78(m, 4H,—C<u>H₂</u>), 2.32(t, 2H,—C<u>H₂</u>), 3.69(s, 3H, —O<u>CH₃</u>), 3.80 (s, 3H, —O<u>CH₃</u>), 3.88(s, 6H, ester), 3.98(t, 2H —O<u>CH₂</u>), 6.28(d, 1H, J=17.7 Hz, C<u>H</u>=CH), 6.71 (s, 2H, Ar), 7.58(d, 1H, J=17.7 Hz, CH=C<u>H</u>).

EXAMPLE 26

3-[3,5-Dimethoxy-4-(2-methoxycarbonylmethoxy-ethoxy)-phenyl]-acrylic acid methyl ester (26)

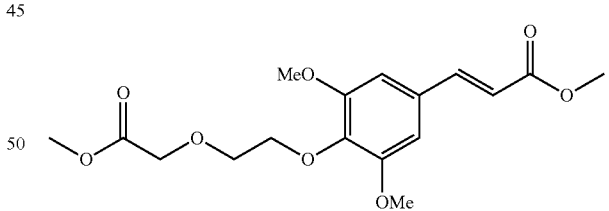

To a mixture of methyl sinapinate (20 grams, 84 mmol), anhydrous K₂CO₃ (50 grams, 361 mmol), Sodium iodide (5 grams, 33.4 m mol), disodium phosphate (7 grams, 49.4 mmol) in anhydrous acetone (300 mL) was added (2-Bromoethoxy)-acetic acid methyl ester (22 grams, 112 mmol) and refluxed for 12 days. Acetone was distilled and water (200 mL) was added. Crude 26 was filtered and purified by column chromatography on silica gel using hexane:Ethyl acetate (95: 5) to give pure 26 (2 grams, 6.7%) as a white powder. The melting point was found to be 66-68° C. The structure was confirmed with IR and NMR. ᴵHNMR (CDCl₃) δ 3.73(s, 3H, ester), 3.78(s, 3H, ester), 3.85(s, 6H, OCH₃), 3.88(t, 2H, OCH₂), 4.15 (t, 2H, OCH₂), 4.25 (t, 2H, OCH₂), 6.26(d, 1H, J=17.5 Hz, CH═CH), 6.70 (s, 2H, Ar), 7.56(d, 1H, J=17.5 Hz, CH═CH).

EXAMPLE 27

6-[4-(5-Methoxycarbonyl-pentyloxy)-phenoxy]-hexanoic acid methyl ester (27)

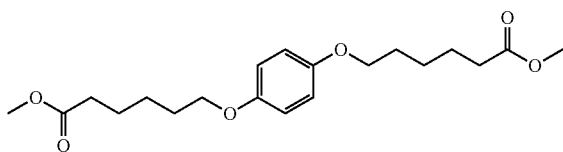

To a mixture of Hydroquinone (20 grams, 18.2 mmol), anhydrous K₂CO₃ (190 grams, 1.375 mmol), sodium iodide (3 grams, 20 mmol) in anhydrous acetone was added methyl 6-bromo hexanoate and refluxed for 60 hours. Acetone was distilled and water (500 mL) was added. Crude 27 was filtered, dried, and recrystallized from methanol to give pure 27 (43 grams, 64.7%) as a white powder. The melting point was found to be 77.2-78.9° C. The structure was confirmed with IR and NMR. ¹HNMR (CDCl₃) δ 1.52 (m, 4H,CH₂), 1.75(m, 12H, CH₂), 2.30(t, 4H,CH₂), 3.62 (s, 6H, Ester), 3.86 (t, 4H,OCH₂), 6.75 (s,4H,Ar).

EXAMPLE 28

(2-Acetyl-4-ethoxycarbonylmethoxy-phenoxy)-acetic acid ethyl ester (28)

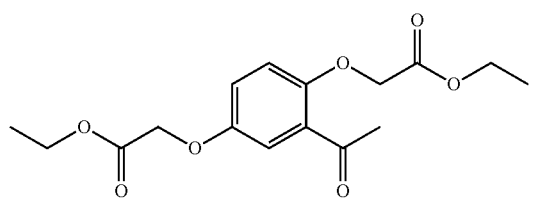 [SMILES: CCOC(=O)COc1ccc(OCC(=O)OCC)c(C(C)=O)c1]

To a mixture of 2',5'-Dihydroxy acetophenone (25 grams, 164 mmol), and anhydrous K₂CO₃ (150 grams, 1.08 mol) in anhydrous acetone (1000 mL) was added ethyl bromo acetate (75.3 grams, 451 mmol) and refluxed for 78 hours. Acetone was distilled and water (1000 mL) was added. Crude 28 was filtered dried and recrystallized from toluene to give pure 28 (40 grams, 75%) as a wheat color powder. The melting point found to be 56.8-59° C. The structure was confirmed with IR and NMR. ¹HNMR (CDCl₃) δ 1.34 (t, 6H, CH₂CH₃), 2.70(s, 3H, CH₃), 4.28(q, 4H, CH₂CH₃), 4.60 (s, 2H, OCH₂), 4.68(s, 2H,OCH₂), 6.80 (d,1H,Ar), 7.08(dd,1H,Ar), 7.28(d,1H,Ar).

EXAMPLE 29

2-(6-Hydroxy-naphthalen-2-yl)-propionic acid (29)

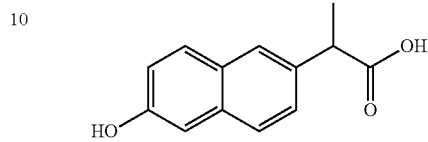

A mixture of Naproxen (500 grams, 2.774 mmol) and 48% HBr (1500 mL) was refluxed for 10 hours, poured onto ice water (3000 mL), and stirred for 30 minutes. Crude 29 was filtered, dried (380 grams, 81%), and used as such for the next stage.

EXAMPLE 30

2-(6-Hydroxy-naphthalen-2-yl)-propionic acid methyl ester

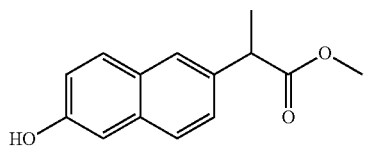 [SMILES: COC(=O)C(C)c1ccc2cc(O)ccc2c1]

To a solution of methanol (2100 mL) and sulphuric acid (84 mL) was added 2-(6-Hydroxy-naphthalen-2-yl)-propionic acid 29 (420 grams, 1.944 mmol), and refluxed for 6 hours. Methanol (1000 mL) was distilled and the cooled reaction mass was poured onto ice water (3000 mL) Crude 30 was filtered, dried, and recrystallized from a mixture of Ethyl acetate:Hexane (1:5) to give pure 30 (400 grams, 89.5%) as a white fluffy powder. The melting point found to be 89.5-92° C. The structure was confirmed with IR and NMR. ¹HNMR (CDCl₃) δ 1.60(d,3H,CH₃), 3.70(s,3H,Ester), 3.88 (q,1H, CH), 5.36(bs,1H,OH), 7.08(m,2H,Ar), 7.48(m,1H,Ar), 7.65 (m,3H,Ar).

EXAMPLE 31

2-(6-Methoxycarbonylmethoxy-naphthalen-2-yl)-propionic acid methyl ester (31)

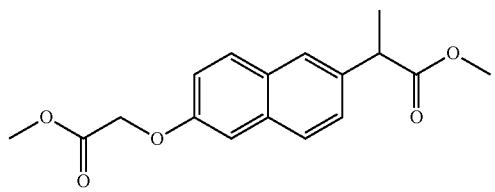

To a mixture of 2-(6-Hydroxy-naphthalen-2-yl)-propionic acid methyl ester 30 (175 grams, 761 mmol), anhydrous K₂CO₃ (315 grams, 2.279 mmol), sodium iodide (21 grams, 140 mmol) in anhydrous acetone (2000 mL) was added methyl Chloro acetate (104 grams, 958 mmol) and refluxed for 6 hours. Acetone was distilled and water (1500 mL) was added. Crude 31 was extracted into Ethyl acetate, dried over $Na_2SO_4$, distilled and purified by column chromatography on silica gel using Benzene as eluant to give pure 31 (125 grams, 54.3%) as a pale yellow syrup. The structure was confirmed with NMR. $^1HNMR$ (CDCl$_3$) δ 1.57 (d,3H,CH$_3$), 3.64 (s,3H, Ester), 3.78 (s,3H,Ester), 3.80(q,1H,CH), 4.70(s,1H,Ar), 7.22(d,1H,Ar), 7.36(m,2H,Ar), 7.68(m,3H,Ar).

EXAMPLE 32

2-[6-(1-Methoxycarbonyl-ethoxy)-naphthalen-2-yl]-propionic acid methylester (32)

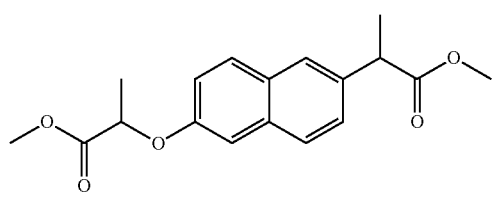

To a mixture of 2-(6-hydroxy-naphthalen-2-yl)-propionic acid methyl ester 30 (150 grams, 652 mmol), anhydrous $K_2CO_3$ (455 grams, 3.292 mol), sodium iodide (22.5 grams, 150 mmol) in anhydrous acetone (2000 mL) was added methyl 2-Chloro propionate (107.5 grams, 877 mmol) and refluxed for 50 hours. Acetone was distilled and water (1500 mL) was added. Crude 32 was extracted into Ethyl acetate, dried over $Na_2SO_4$, distilled and purified by column chromatography on silica gel using Hexane as eluant to give pure 32 (175 grams, 85%) as a light yellow syrup. The structure was confirmed with NMR. $^1HNMR$ (CDCl$_3$) δ 1.55(d,3H,CH$_3$), 1.68(d,3H,CH$_3$), 3.62(s,3H,Ester), 3.72(s,3H,Ester), 3.82 (q,1H,CH), 3.91(q,1H,OCH), 7.02(s,1H,Ar), 7.18(d,1H,Ar), 7.36(d,1H,Ar), 7.68 (m,3H,Ar).

EXAMPLE 33

6-[6-(1-Methoxycarbonyl-ethyl)-naphthalen-2-yloxy]-hexanoic acid methyl ester (33)

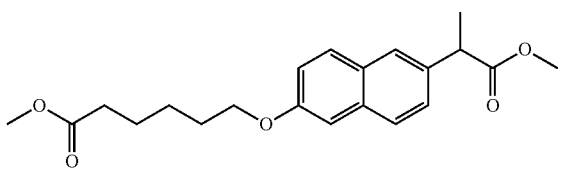

To a mixture of 2-(6-hydroxy-naphthalen-2-yl)-propionic acid methyl ester 30 (150 grams, 652 mmol), anhydrous $K_2CO_3$ (480 grams, 3.473 mol) sodium iodide (22.5 grams, 150 mmol) in anhydrous acetone (2000 mL) was added methyl 6-bromo hexanoate (216 grams, 1.033 mol) and refluxed for 60 hours. Acetone was distilled and water (1500 mL) was added. Crude 33 was extracted into Ethyl acetate, dried over $Na_2SO_4$, distilled and purified by column chromatography on silica gel using Hexane as eluant to give pure 33 (130 grams, 55.6%) as a light yellow syrup. The structure was confirmed with NMR. $^1HNMR$ (CDCl$_3$) δ 1.59(d,3H,CH$_3$), 1.60(d,2H,CH$_2$), 1.75(m,2H,CH$_2$), 1.89(m,2H,CH$_2$), 2.38(t, 2H,CH$_2$), 3.69(s,6H,Ester), 3.88(q,1H,CH), 4.08(t,2H, OCH$_2$), 7.10(m,2H,Ar), 7.40(d,1H,Ar), 7.68(m,3H,Ar).

EXAMPLE 34

(2-Oxo-2H-chromen-7-yloxy)-acetic acid methyl ester (34)

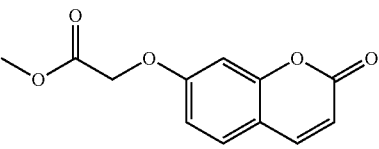 [SMILES: COC(=O)COc1ccc2ccc(=O)oc2c1]

To a mixture of 7-hydroxy coumarin (100 grams, 617 mmol) and anhydrous $K_2CO_3$ (400 grams, 2.894 mol) in anhydrous acetone (2000 mL) was added methyl chloro acetate (123.8 grams, 1.14 mol) and refluxed for 6 hours. Acetone was distilled and water (2000 mL) was added. Crude 34 was filtered, dried, and recrystallized from toluene to give pure 34 (110 grams, 76.38%) as a cream color shining powder. The melting point was found to be 145-147.1° C. The structure was confirmed with IR and NMR. $^1HNMR$ (CDCl$_3$) δ 3.80 (s, 3H,Ester), 4.69(s, 2H,OC$\underline{H}_2$), 6.24(d, 1H, Pyran), 6.76 (d, 1H,Ar), 6.88(dd,1H,Ar), 7.41(d,1H,Ar), 7.62(d,1H, pyran).

EXAMPLE 35

(2-Oxo-2H-chromen-4-yloxy)-acetic acid methyl ester (35)

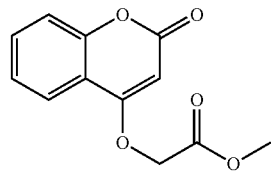 [SMILES: COC(=O)COc1cc(=O)oc2ccccc12]

To a mixture of 4-hydroxy coumarin (100 grams, 617 mmol) and anhydrous $K_2CO_3$ (450 grams, 3.256 mol) in anhydrous acetone (2000 mL) was added methyl chloro acetate (155 grams, 1.43 mols) and refluxed for 8 hours. Acetone was distilled and water (2000 mL) was added. Crude 34 was filtered, dried, and recrystallized from toluene to give pure 34 (25 grams, 17.4%) as a white fluffy powder. The melting point was found to be 179.6-181.2° C. The structure was confirmed with IR and NMR. $^1HNMR$ (CDCl$_3$) δ 3.84 (s, 3H,Ester), 4.80(s, 2H,O<u>CH</u>₂), 5.58(s,1H,Pyran), 7.28 (m, 2H,Ar), 7.59(m,1H,Ar), 7.88(dd,1H,Ar).

EXAMPLE 36

(4-Methyl-2-oxo-2H-chromen-6-yloxy)-acetic acid methyl ester (36)

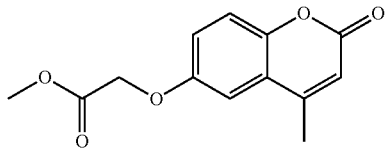 [SMILES: COC(=O)COc1ccc2oc(=O)cc(C)c2c1]

To a mixture of 6-hydroxy-4-methyl coumarin (110 grams, 624 mmol), anhydrous K₂CO₃ (176 grams, 1.273 mol), Sodium iodide (11 grams, 73.4 mmol), disodium phosphate (44 grams, 310 mmol) in anhydrous acetone (1100 mL) was added methyl chloro acetate (81.7 grams, 753 mmol) and refluxed for 12 hours. Acetone was distilled and water (1200 mL) was added. Crude 36 was filtered and recrystallized from a mixture of methanol:chloroform (2:1) to give pure 36 (112 grams, 72.2%) as a white shining powder. The melting point was found to be 153.8-155.5° C. The structure was confirmed with IR and NMR. $^{I}$HNMR (CDCl₃) δ 2.39 (s, 3H, <u>CH</u>₃), 3.79 (s, 3H, ester), 4.64 (s, 2H, O<u>CH</u>₂), 6.25 (s, 1H, pyran), 7.05 (m, 2H, Ar), 7.25 (d, 1H, Ar).

EXAMPLE 37

[3-(4-Methoxy-phenyl)-4-methyl-2-oxo-2H-chromen-6-yloxy]-acetic acid methyl ester (37)

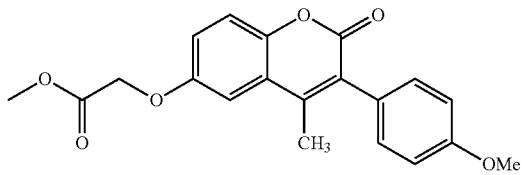 [SMILES: COC(=O)COc1ccc2oc(=O)c(-c3ccc(OC)cc3)c(C)c2c1]

To a mixture of 6-hydroxy-3-(4'-methoxy phenyl)-4-methyl coumarin (150 grams, 523 mmol), anhydrous K₂CO₃ (300 grams, 2.17 mol) in anhydrous acetone (1500 mL) was added methyl chloro acetate (148.5 grams, 1.369 mol) and refluxed for 8 hours. Acetone was distilled and water (1000 mL) was added. Crude 37 was filtered dried and recrystallized from methanol to give pure 37 (140 grams, 74.5%) as a cream color shining powder. The melting point was found to be 120.8-122.3° C. The structure was confirmed with IR and NMR. $^{I}$HNMR (CDCl₃) δ 2.28 (s, 3H, <u>CH</u>₃), 3.80(s, 3H,Ester), 3.84(s, 3H,O<u>CH</u>₃), 4.66 (s, 2H,O<u>CH</u>₂), 6.92(dd,2H,Ar), 7.20 (m, 5H,Ar).

EXAMPLE 38

(6-Methoxycarbonylmethoxy-4-methyl-2-oxo-2H-chromen-7-yloxy)-acetic acid methyl ester (38)

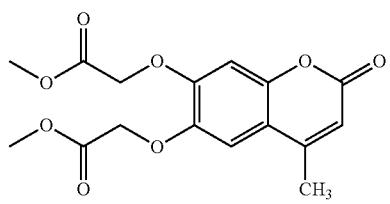 [SMILES: COC(=O)COc1cc2oc(=O)cc(C)c2cc1OCC(=O)OC]

To a mixture of 6,7-Dihydroxy-4-methyl coumarin (80 grams, 416 mmol), anhydrous K₂CO₃ (240 grams, 1.737 mol), Sodium iodide (16 grams, 107 mmol), disodium phosphate (64 grams, 451 mmol) in anhydrous acetone (1200 mL) was added methyl chloro acetate (109 grams, 1000 mmol) and refluxed for 12 hours. Acetone was distilled and water (1500 mL) was added. Crude 38 was filtered, dried, and recrystallized from acetic acid to give pure 38 (105 grams, 75%) as a white fluffy powder. The melting point was found to be 170-171.8° C. The structure was confirmed with IR and NMR. $^{I}$HNMR (CDCl₃) δ 2.38 (s, 3H, —<u>CH</u>₃), 3.79 (s, 3H, ester), 3.81 (s, 3H, Ester), 4.65 (s, 2H, —O<u>CH</u>₂), 4.67 (s, 1H, 2H, —O<u>CH</u>₂), 6.15 (s, 1H, pyran), 6.72 (s, 1H, Ar), 7.19 (s, 1H, Ar).

EXAMPLE 39

(7-Oxo-7H-furo[3,2-g]chromen-4-yloxy)-acetic acid methyl ester (39)

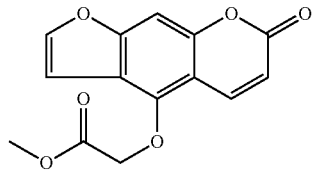 [SMILES: COC(=O)COc1c2ccoc2cc2oc(=O)ccc12]

To a mixture of Bergaptol (10 grams, 49.5 mmol), anhydrous K₂CO₃ (20 grams, 144.7 mmol), Sodium iodide (2.4 grams, 16 mmol), disodium phosphate (2.4 grams, 17 mmol) in anhydrous acetone (250 mL) was added methyl chloro acetate (9.3 grams, 85.6 mmol) and refluxed for 8 hours. Acetone was distilled and water (100 mL) was added. Crude 39 was filtered and recrystallized in a mixture of methanol:chloroform (9:1) to give pure 39 (3 grams, 22.1%) as a white powder. The melting point was found to be 180.6-182.8° C. The structure was confirmed with IR and NMR. $^{I}$HNMR (CDCl₃) δ 3.81(s, 2H, ester), 4.97(s, 2H,—O<u>CH</u>₂), 6.32(d, 1H, J=12.4 Hz, pyran), 6.83(d, 1H, J=1.1 Hz, furan), 7.21(s, 1H, Ar), 8.28(d, 1H, J=12.4 Hz, pyran).

EXAMPLE 40

2-(7-oxo-7H-furo[3,2-g]chromen-4-yloxy)-propionic acid methyl ester (40)

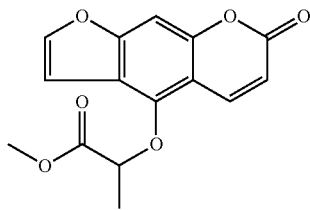 [SMILES: COC(=O)C(C)Oc1c2ccoc2cc2oc(=O)ccc12]

To a mixture of Bergaptol (10 grams, 49.5 mmol), anhydrous $K_2CO_3$ (20 grams, 144.7 mmol), Sodium iodide (2.4 grams, 16 mmol), disodium phosphate (2.4 grams, 17 mmol) in anhydrous acetone (250 mL) was added methyl 2-chloro propionate (10 mL, 87.7 mmol) and refluxed for 8 hours. Acetone was distilled and water (100 mL) was added. Crude 40 was filtered and recrystallized in a mixture of methanol:chloroform (9:1) to give pure 40 (5.5 grams, 38.5%) as a white powder. The melting point was found to be 149.6-151.6° C. The structure was confirmed with IR and NMR. $^I$HNMR (CDCl$_3$) δ 1.78(d, 3H,—CH$_3$), 3.68(s, 3H, ester), 5.18(q, 1H, CH), 6.31(d, 1H, J=12.1 Hz, pyran), 6.84(d, 1H, J=1.1 Hz, furan), 7.22(s, 1H, Ar), 7.64(d, 1H, J=1.1 Hz, furan), 8.36(d, 1H, J=12.1 Hz, pyran).

EXAMPLE 41

6-(7-oxo-7H-furo[3,2-g]chromen-4-yloxy)-hexanoic acid methyl ester (41)

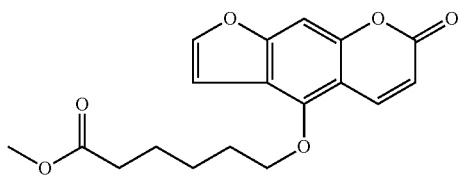 [SMILES: COC(=O)CCCCCOc1c2ccoc2cc2oc(=O)ccc12]

To a mixture of Bergaptol (5 grams, 24.7 mmol), anhydrous $K_2CO_3$ (12.5 grams, 90 mmol), Sodium iodide (7.5 grams, 50 mmol), disodium phosphate (12.5 grams, 88 mmol) in anhydrous acetone (250 mL) was added methyl 6-bromo hexanoate (7.5 grams, 35.9 mmol) and refluxed for 8 hours. Acetone was distilled and water (100 mL) was added. Crude 41 was filtered and recrystallized in methanol to give pure 41 (3 grams, 36.8%) as a white powder. The melting point was found to be 98.8-101.8° C. The structure was confirmed with IR and NMR. $^I$HNMR (CDCl$_3$) δ 1.62 (m, 3H,—CH$_2$), 1.75(m, 2H,—CH$_2$), 1.92(m, 2H,—CH$_2$), 2.38(t, 2H,—CH$_2$), 3.68(s, 3H, ester), 4.45(t, 2H, OCH$_2$), 6.22(d, 1H, J=12.5 Hz, pyran), 6.90(s, 1H, furan), 7.11(s, 1H, Ar), 7.55(s, 1H, furan), 8.19(d, 1H, J=12.5 Hz, pyran).

EXAMPLE 42

(7-Oxo-7H-furo[3,2-g]chromen-9-yloxy)-acetic acid methyl ester (42)

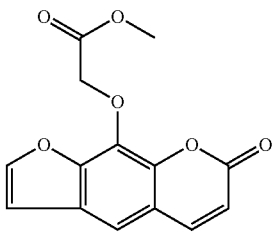 [SMILES: COC(=O)COc1c2occc2cc2ccc(=O)oc12]

To a mixture of Xanthotoxol (10 grams, 49.5 mmol), anhydrous $K_2CO_3$ (20 grams, 145 mmol), sodium iodide (2.5 grams, 16.7 mmol), disodium phosphate (2.5 grams, 17.7 mmol) in anhydrous acetone (250 mL) was added methyl chloro acetate (9.3 grams, 85.5 mmol) and refluxed for 10 hours. Acetone was distilled and water (25 mL) was added. Crude 42 was filtered, dried, and recrystallized from a mixture of methanol:chloroform (4:1) to give pure 42 (9 grams, 66.4%) as a white shining powder. The melting point was found to be 139.5-141° C. The structure was confirmed with IR and NMR. $^I$HNMR (CDCl$_3$) δ 3.81 (s, 2H,Ester), 5.18(s, 2H, OCH$_2$), 6.36(d, 1H,J=12.5H$_z$, pyran), 6.79 (d, 1H, J=1H$_z$, Furan), 7.38 (s,1H,Ar), 7.65 (d, 1H, J=1H$_z$, Furan), 7.74 (d, 1H,J=12.5H$_z$ pyran).

EXAMPLE 43

2-(7-Oxo-7H-furo[3,2-g]chromen-9-yloxy)-propionic acid methyl ester (43)

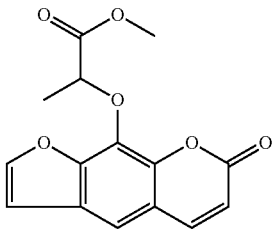 [SMILES: COC(=O)C(C)Oc1c2occc2cc2ccc(=O)oc12]

To a mixture of Xanthotoxol (10.5 grams, 52 mmol), anhydrous $K_2CO_3$ (21 grams, 152 mmol), sodium iodide (2.6 grams, 17.3 mmol) Disodium phosphate (2.6 grams, 18.4 mmol) in anhydrous acetone (270 mL) was added methyl 2-chloro propionate (11.3 grams, 92.2 mmol) and refluxed for 12 hours. Acetone was distilled and water (150 mL) was added. Crude 43 was filtered, dried, and recrystallized from a mixture of chloroform:Hexane (1:5) to give pure 43 (3.5 grams, 23.5%) as a white powder. The melting point was found to be 104.5-105.6° C. The structure was confirmed with IR and NMR. $^I$HNMR (CDCl$_3$) δ 1.78 (d, 3H, CH$_3$), 3.78(s, 2H,OCH$_2$), 5.34(q, 1H,OCH), 6.32 (d, 1H,J=12.6H$_z$, Pyran), 6.78 (d,1H,J=1.1 H$_z$,Furan), 7.32 (s, 1H,Ar), 7.68 (d, 1H,J=1.1H$_z$ Furan) 7.73(d,1H,J=12.6 H$_z$,Pyran).

EXAMPLE 44

6-(7-Oxo-7H-furo[3,2-g]chromen-9-yloxy)-hexanoic acid methyl ester (44)

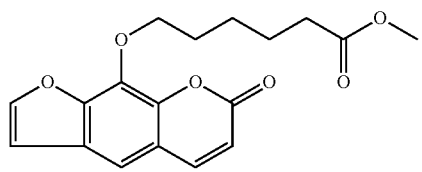 [SMILES: COC(=O)CCCCCOc1c2occc2cc2ccc(=O)oc12]

To a mixture of Xanthotoxol (10 grams, 49.5 mmol), anhydrous K$_2$CO$_3$ (25 grams, 180 mmol), sodium iodide (15 grams, 100 mmol), disodium phosphate (25 grams, 177 mmol) in anhydrous acetone (500 mL) was added methyl 6-bromo hexanoate (15 grams, 72 mmol) and refluxed for 18 hours. Acetone was distilled and water (200 mL) was added. Crude 44 was extracted into ethyl acetate, solvent distilled and purified by column chromatography on silica gel using benzene as a eluant to give pure 44 (1.5 grams, 9.2%) as a white powder. The melting point was found to be 49-50.5° C. The structure was confirmed with IR and NMR. $^1$HNMR (CDCl$_3$) δ 1.63 (m, 6H, —CH$_2$), 2.35(t, 2H,—CH$_2$$^-$), 3.62(s, 3H,Ester), 4.42 (t, 2H,OCH$_2$) 6.31(d,1H,J=12.6H$_z$, Pyran), 6.79 (d,1H,J=1 H$_z$,Furan), 7.31(s, 1H,Ar), 7.65 (d, 1H,J=1H$_z$, Furan), 7.73(d,1H,J=12.6 H$_z$, Pyran).

EXAMPLE 45

Psoralen quinine (45)

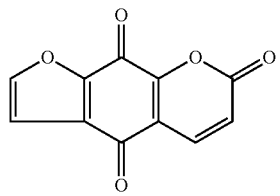 [SMILES: O=C1c2ccoc2C(=O)c2oc(=O)ccc21]

9-methoxy psoralene (30 grams, 138.7 mmol) was dissolved in 900 mL glacial acetic acid. To this solution was added 900 mL of 15% aqueous chromium trioxide solution. The resulting solution was brought just to boiling on the hot plate then poured immediately into 7500 mL water and cooled. The product was filtered, washed with ethanol to give 8 grams crude 45 as a rose powder (Ref: *J. Org. chem.* 1959, 24, 523-526).

EXAMPLE 46

4,9-Dihydroxy psoralen (46)

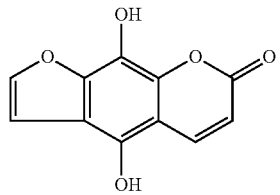 [SMILES: O=c1ccc2c(O)c3ccoc3c(O)c2o1]

Psoralen quinone 45 (5 grams, 23.2 mmol) was suspended in 1250 mL water and heated on the steam bath. This suspension was saturated with sulfur dioxide by bubbling the gas through the hot liquid for 10 minutes. At the end of this time, all the material had dissolved giving the solution a light green color. Upon cooling, green crystals 46 formed filtered and dried to give pure 46 (4.2 grams, 83.3%). (Ref: J. Org. chem. 1959, 24, 523-526).

EXAMPLE 47

(4-Methoxycarbonylmethoxy-7-oxo-7H-furo[3,2-g]chromen-9-yloxy)-acetic acid methyl ester (47)

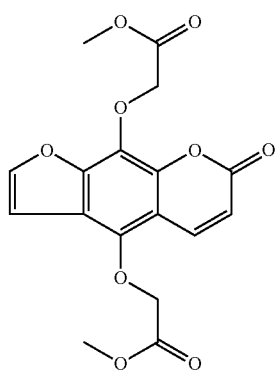 [SMILES: COC(=O)COc1c2ccoc2c(OCC(=O)OC)c2oc(=O)ccc12]

To a mixture of 4,9-dihydroxy psoralene 46 (10 grams, 45.8 mmol), anhydrous K$_2$CO$_3$ (200 grams, 1.447 mol), Sodium iodide (5 grams, 33.3 mmol), disodium phosphate (20 grams, 141.6 mmol) in anhydrous acetone (5 liter) was added methyl chloro acetate (20 mL, 228.2 mmol) and refluxed for 16 hours. Acetone was distilled and water (1 liter) was added. Crude 47 was extracted into chloroform, dried over Na$_2$SO$_4$, distilled and purified by column chromatography on silica gel using benzene:ethyl acetate (9:1) to give pure 47 (1 gram, 6.02%) as a off white powder. The melting point was found to be 165.5-169° C. The structure was confirmed with NMR. $^1$HNMR (CDCl$_3$) δ 3.82 (s, 6H, Ester), 4.90 (s, 2H, OCH2), 5.05 (s, 2H, OCH$_2$), 6.38 (d, 1H, J=12.5 Hz, pyran), 6.90 (d, 1H, J=1 Hz, furan), 7.69 (d, 1H, J=1 Hz, furan), 8.38 (d, 1H, J=12.5 Hz, pyran).

EXAMPLE 48

6-[4-(5-Methoxycarbonyl-pentyloxy)-7-oxo-7H-furo[3,2-g]chromen-9-yloxy]-hexanoic acid methyl ester (48)

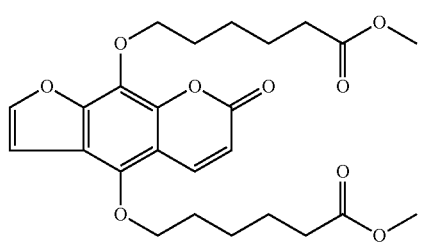 [SMILES: COC(=O)CCCCCOc1c2ccoc2c(OCCCCCC(=O)OC)c2oc(=O)ccc12]

To a mixture of 4,9-dihydroxy psoralene 46 (15 grams, 68.8 mmol), anhydrous K$_2$CO$_3$ (300 grams, 2.17 mol), Sodium iodide (7.5 grams, 50 mmol), disodium phosphate (30 grams, 212.5 mmol) in anhydrous acetone (5 liter) was added methyl 6-bromo hexanoate (75 grams, 358.8 mmol) and refluxed for 16 hours. Acetone was distilled and water (1 liter) was added. Crude 48 was extracted into ethyl acetate, dried over $Na_2SO_4$, distilled and purified by column chromatography on silica gel using benzene:ethyl acetate (95:5) to give pure 48 (325 mg, 1%) as a off-white powder. The melting point was found to be 75-78° C. The structure was confirmed with NMR. $^1$HNMR (CDCl$_3$) δ 1.70 (m, 12H, —CH$_2$—), 2.25 (t, 4H, —CH$_2$—), 3.65 (s, 6H, Ester), 4.35 (t, 4H, OCH$_2$), 6.38 (d, 1H, J=12.5 Hz, pyran), 6.91 (d, 1H, J=1 Hz, furan), 7.61 (d, 1H, J=1 Hz, furan), 8.13 (d, 1H, J=12.5 Hz, pyran).

EXAMPLE 49

(4-Oxo-3-phenyl-4H-chromen-7-yloxy)-acetic acid methyl ester (49)

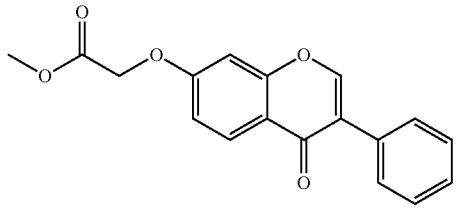 [SMILES: COC(=O)COc1ccc2c(=O)c(-c3ccccc3)coc2c1]

To a mixture of 7-Hydroxy isoflavone (35 grams, 147 mmol), anhydrous $K_2CO_3$ (84 grams, 608 mmol) in anhydrous acetone (500 mL) was added ethyl bromo acetate (29 grams, 174 mmol) and refluxed for 8 hours. Acetone was distilled and water (500 mL) was added. Crude 49 was filtered, dried, and recrystallized from toluene to give pure 49 (33 grams, 72.4%) as a white shining powder. The melting point was found to be 105-106.5° C. The structure was confirmed with IR and NMR. $^1$HNMR (CDCl$_3$) δ 1.31 (t, 3H,OCH$_2$,CH$_3$), 4.30(q, 2H, OCH$_2$, CH$_3$), 4.70(s, 2H,O CH$_2$), 6.84 (d, 1H,Ar), 7.05 (dd,1H,Ar), 7.41 (m, 3H,Ar), 7.57 (m, 2H,Ar), 7.97(s, 1H, Pyran), 8.24(d,1H,Ar).

EXAMPLE 50

6-(4-Oxo-3-phenyl-4H-chromen-7-yloxy)-hexanoic acid methyl ester (50)

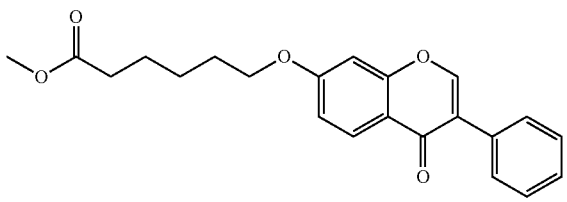 [SMILES: COC(=O)CCCCCOc1ccc2c(=O)c(-c3ccccc3)coc2c1]

To a mixture of 7-Hydroxy isoflavone (20 grams, 84 mmol), anhydrous $K_2CO_3$ (84 grams, 362 mmol) sodium iodide (4 grams, 27 mmol), disodium phosphate (4 grams, 28 mmol) in anhydrous acetone (250 mL) was added methyl 6-bromo hexanoate (22 grams, 105 mmol) and refluxed for 12 hours. Acetone was distilled and water (400 mL) was added. Crude 50 was filtered, dried, and recrystallized from methanol to give pure 50 (22 grams, 71.5%) as a white powder. The melting point was found to be 119.3-122.3° C. The structure was confirmed with IR and NMR. $^1$HNMR (CDCl$_3$) δ 1.52 (m, 2H,CH$_2$), 1.72(m, 2H, CH$_2$), 1.88(m, 2H,CH$_2$), 2.34 (t, 2H, CH$_2$), 3.68 (s,3H,Ester), 4.02 (t, 2H,—OCH$_2$) 6.78 (d, 1H,Ar), 6.95 (dd, 1H, Ar), 7.38(m,3H,Ar), 7.52(m,2H,Ar), 7.90(s,1H,Pyran), 8.24(d,1H,Ar).

EXAMPLE 51

6-[3-(4-Methoxy-phenyl)-4-oxo-4H-chromen-7-yloxy]-hexanoic acid methyl ester (51)

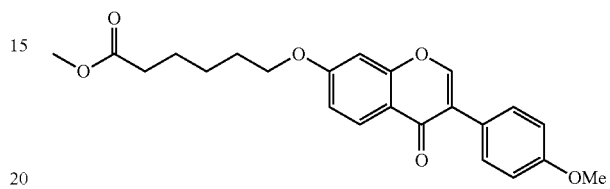

To a mixture of 7-hydroxy-4'-methoxy isoflavone (10 grams, 37.3 mmol), anhydrous $K_2CO_3$ (30 grams, 217 mmol), sodium iodide (2 grams, 13.3 mol), disodium phosphate (3 grams, 21.2 mmol) in anhydrous acetone was added methyl 6-bromo hexanoate (13 grams, 62.2 mmol) and refluxed for 28 hours. Acetone was distilled and water (150 mL) was added. Crude 51 was filtered, dried and purified by column chromatography on silica gel using chloroform as eluant to give pure 51 (8 grams, 54.2%) as a white powder. The melting point was found to be 130-133° C. The structure was confirmed with IR and NMR. $^1$HNMR (CDCl$_3$) δ 1.56 (m, 2H,CH$_2$), 1.74(m,2H, CH$_2$), 1.84(m,2H CH$_2$), 2.38(t 2H, CH$_2$), 3.66(s,3H,ester), 3.82 (s,3H,OCH$_3$), 4.04 (t,2H,O CH$_2$), 6.86(s,1H,Ar), 6.92(d,2H,Ar), 7.24(d,2H,Ar), 7.84 (s,1H,Pyran), 8.16(d,1H,Ar).

EXAMPLE 52

[3-(4-Methoxycarbonylmethoxy-phenyl)-4-oxo-4H-chromen-7-yloxy]-acetic acid methyl ester (52)

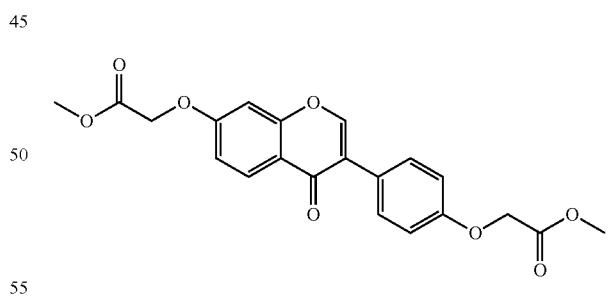

To a mixture of 4',7-dihydroxy isoflavone (20 grams, 79 mmol), anhydrous $K_2CO_3$ (100 grams, 723 mmol), Sodium iodide (8 grams, 53.4 mmol), disodium phosphate (8 grams, 57 mmol) in anhydrous acetone (600 mL) was added methyl chloro acetate (29.2 grams, 269 mmol) and refluxed for 6 hours. Acetone was distilled and water (600 mL) was added. Crude 52 was filtered, dried, and recrystallized from toluene to give pure 52 (22 grams, 70%) as a white powder. The melting point was found to be 163-165.7° C. The structure was confined with IR and NMR. $^1$HNMR (CDCl$_3$) δ 3.69(s, 3H, ester), 3.80 (s, 3H, Ester), 4.68(s, 2H, OCH$_2$), 4.79(s, 2H, OCH$_2$), 6.83(d, 1H, Ar), 6.88(dd,2H, B-ring), 7.02 (dd, 1H, Ar), 7.46 (dd,2H,B-ring), 8.00(s,1H,pyran), 8.18(dd,1H,Ar).

EXAMPLE 53

[6-Methoxy-3-(4-methoxy-phenyl)-4-oxo-4H-chromen-7-yloxy]-acetic acid methyl ester (53)

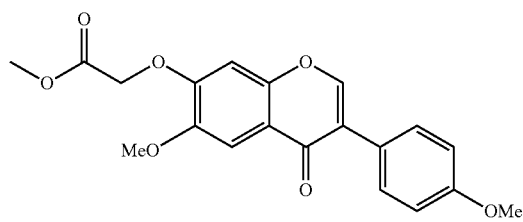 [SMILES: COC(=O)COc1cc2occ(-c3ccc(OC)cc3)c(=O)c2cc1OC]

To a mixture of 4',6-Dimethoxy-7-Hydroxyisoflavone (5 grams, 16.8 mmol), anhydrous K$_2$CO$_3$ (10 grams, 72 mmol), sodium iodide (1 gram, 6.7 mmol), disodium phosphate (1 gram, 7.1 mmol) in anhydrous acetone (60 mL) was added methyl chloro acetate (2.3 grams, 21 mmol) and refluxed for 8 hours. Acetone was distilled and water (40 mL) was added. Crude 53 was filtered, dried, and recrystallized from a mixture of methanol:chloroform (1:1) to give pure 53 (3 grams, 48.4%) as a white fluffy powder. The melting point was found to be 179-180.5° C. $^1$HNMR (CDCl$_3$) δ 3.80 (s, 6H,OCH$_3$), 3.98(s,3H,ester), 4.76(s, 2H,OCH$_2$), 6.72(s,1H,Ar), 6.90 (d, 2H, Ar), 7.42 (d,2H,Ar), 7.62(s,1H,Ar), 7.88(s,1H,Pyran).

EXAMPLE 54

[6-Methoxy-3-(4-methoxycarbonylmethoxy-phenyl)-4-oxo-4H-chromen-7-yloxy]-acetic acid methyl ester (54)

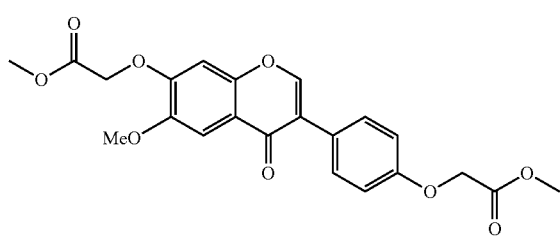

To a mixture of Glycitein (5 grams, 17.6 mmol), anhydrous K$_2$CO$_3$ (20 grams, 144.7 mmol), Sodium iodide (5 grams, 33.3 mmol), disodium phosphate (5 grams, 35.4 mmol) in anhydrous acetone (100 mL) was added methyl chloro acetate (5.8 mL, 65.1 mmol) and refluxed for 20 hours. Acetone was distilled and water (100 mL) was added. Crude 54 was filtered and recrystallized in a mixture of methanol:chloroform (6:1) to give pure 54 (5 grams, 66.3%) as a white powder. The melting point was found to be 151-153.5° C. The structure was confirmed with IR and NMR. $^1$HNMR (CDCl$_3$) δ 3.81(s, 3H, ester), 3.83(s, 3H, ester), 4.01(s, 3H, —OCH$_3$), 4.70(s, 2H,—OCH$_2$), 4.82(s, 2H,—OCH$_2$), 6.80(s, 1H, Ar), 6.98(d, 2H, B-ring), 7.53(d, 2H, B-ring), 7.68(s, 1H, Ar), 7.96(s, 1H, pyran).

EXAMPLE 55

6-{6-Methoxy-3-[4-5-methoxycarbonyl-pentyloxy)-phenyl]-4-oxo-4H-chromen-7-yloxy}-hexanoic acid methyl ester (55)

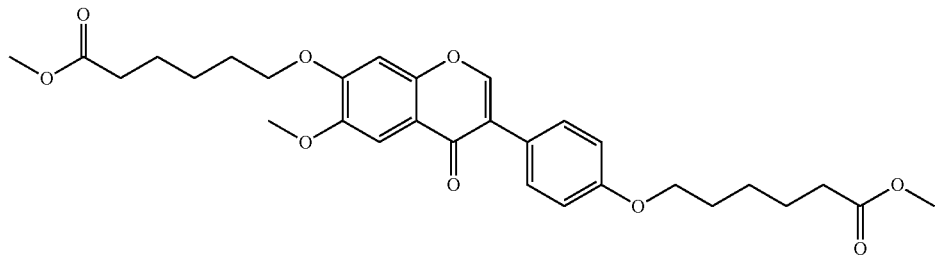

To a mixture of Glycitein (5 grams, 17.6 mmol), anhydrous K$_2$CO$_3$ (20 grams, 144.7 mmol), Sodium iodide (5 grams, 33.3 mmol), disodium phosphate (5 grams, 35.4 mmol) in anhydrous acetone (100 mL) was added methyl 6-bromo hexanoate (10 grams, 47.8 mmol) and refluxed for 26 hours. Acetone was distilled and water (100 mL) was added. Crude 55 was filtered and purified by column chromatography on silica gel using hexane:Ethyl acetate (8:2) to give pure 55 (1 gram, 10.5%) as a pale rose powder. The melting point was found to be 100-105° C. The structure was confirmed with IR and NMR.

EXAMPLE 56

{2-Methoxy-4-[(8-methyl-non-6-enoylamino)-methyl]-phenoxy}-acetic acid methyl ester (56)

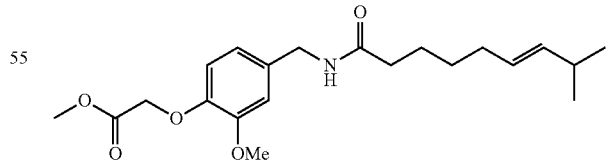

To a mixture of Capsaicin (17 grams, 55.7 mmol), anhydrous K$_2$CO$_3$ (26 grams, 188 mmol), sodium iodide (4.5 grams, 30 mmol) and Disodium phosphate (4.5 grams, 32 mmol) in anhydrous acetone (425 mL) was added methyl chloro acetate (9 grams, 83 mmol) and refluxed for 6 hours. Acetone was distilled and water (150 mL) was added. Crude 56 was filtered, dried, and recrystallized from toluene to give pure 56 (15 grams, 71.4%) as a white power. The melting point was found to be 99.5-103.5° C. It was analyzed by HPLC and found to be 99.3% pure.

EXAMPLE 57

2-{2-Methoxy-4-[(8-methyl-non-6-enoylamino)-methyl]-phenoxy}-propionic acid methyl ester (57)

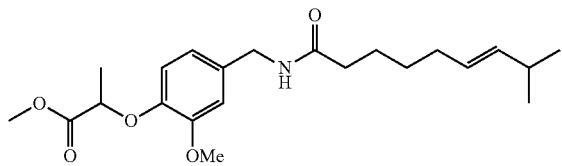 [SMILES: COC(=O)C(C)Oc1ccc(CNC(=O)CCCC/C=C/C(C)C)cc1OC]

To a mixture of Capsaicin (2 grams, 6.56 mmol), anhydrous $K_2CO_3$ (3 grams, 22 mmol), sodium iodide (2 grams, 14.2 mmol) in anhydrous acetone (50 mL) was added methyl 2-chloro propionate (1.2 grams, 10 mmol) and refluxed for 16 hours. Acetone was distilled and water (15 mL) was added. Crude 57 was filtered, dried, and recrystallized from a mixture of chloroform:Hexane (1:5) to give pure 57 (0.8 grams, 31.2%) as a white power. The melting point was found to be 62.3-64° C.

EXAMPLE 58

6-{2-Methoxy-4-[(8-methyl-non-6-enoylamino)-methyl]-phenoxy}-hexanoic acid methyl ester (58)

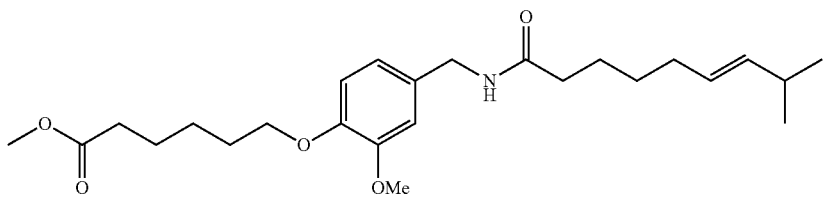 [SMILES: COC(=O)CCCCCOc1ccc(CNC(=O)CCCC/C=C/C(C)C)cc1OC]

To a mixture of Capsaicin (2 grams, 6.56 mmol), anhydrous $K_2CO_3$ (3 grams, 22 mmol), sodium iodide (2 grams, 13.3 mmol) and Disodium phosphate (2 grams, 14.2 mmol) in anhydrous acetone (50 mL) was added methyl 6-bromo Hexanoate (2 grams, 9.6 mmol) and refluxed for 24 hours. Acetone was distilled and water (15 mL) was added. Crude 58 was filtered, dried and purified by column chromatography on silica gel using Benzene:Ethyl acetate (9:1) to give pure 58 (1.5 grams, 52.8%) as a pale white power. The melting point was found to be 69.2-70.8° C.

EXAMPLE 59

(4-Acetylamino-phenoxy)-acetic acid ethyl ester (59)

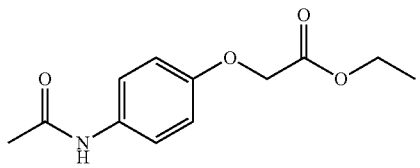 [SMILES: CCOC(=O)COc1ccc(NC(C)=O)cc1]

To a mixture of Paracetamol (300 grams, 1.984 mol), anhydrous $K_2CO_3$ (1.80 Kg, 7.814 mmol) in anhydrous acetone (3 liters) was added ethyl bromo acetate (452 grams, 2.7 mol) and refluxed for 16 hours. Acetone was distilled and water (5 liter) was added. Crude 59 was filtered, dried, and recrystallized from a mixture of toluene:Hexane (1:5) to give pure 59 (377 grams, 80%) as a white shining powder. The melting point was found to be 104.2-106.2° C.

EXAMPLE 60

(4-Amino-phenoxy)acetic acid HCl (60)

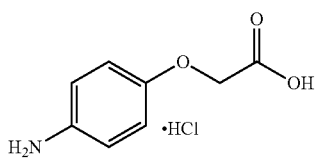

A mixture (4-acetylamino-phenoxy)-acetic acid ethyl ester 59 (375 grams, 1.582 mmol), in concentrated hydrochloric acid (9.36 liters) was refluxed for 12 hours. Excess concentrated hydrochloric acid was distilled off in vacuum and filtered hot. The mixture was cooled to 10° C., filtered and dried to give pure 60 (250 grams, 77.6%) as a wheat colored powder. The melting point was found to be 224-226° C. The structure was confirmed with NMR. $^1$HNMR ($D_2O$) δ 4.68(s, 2H, OCH2), 3.65(s,3H,ester), 7.0(d,2H,Ar), 7.30(d,2H,Ar

EXAMPLE 61

(4-Amino-phenoxy)-acetic acid methyl ester (61)

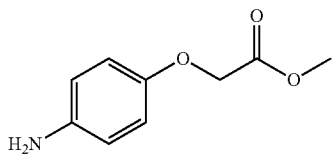

To a mixture (4-Amino-phenoxy)acetic acid HCl 60 (250 grams, 1.228 mol), in methanol (5 liters) was passed dry HCl gas at 10° C. for 1 hour and refluxed for 10 hours. Methanol (3.5 liters) was distilled and ice water (1 liter) was added and the pH was adjusted to 7.5 with $K_2CO_3$. Crude 61 was filtered, dried, and recrystallized from a mixture of Chloroform:Hexane (1:5) to give pure 61 (130 grams, 58.5%) as a light brown powder The melting point was found to be 65-66.8° C.

EXAMPLE 62

2-(4-Acetylamino-phenoxy)-propionic acid methyl ester (62)

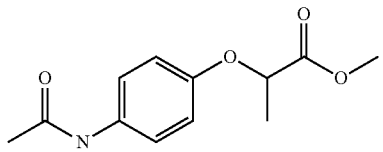 [SMILES: COC(=O)C(C)Oc1ccc(NC(C)=O)cc1]

To a mixture of Paracetamol (150 grams, 992 mmol), anhydrous $K_2CO_3$ (540 Kg, 3.91 mol), sodium iodide (18 grams, 120 mmol) in anhydrous acetone (3 liters) was added methyl 2-chloro propionate (180 grams, 1.469 mmol) and refluxed for 80 hours. Acetone was distilled and water (3 liter) was added. Crude 62 was extracted into chloroform, dried over $Na_2SO_4$, distilled and added hexane (750 mL), filtered and recrystallized in methanol to give pure 62 (95 grams, 40.4%) as a white powder. The melting point was found to be 96.5-98.2° C. The product was tested by HPLC and found to be 99%+ pure. The structure was confirmed with NMR. $^1$HNMR (CDCl$_3$) δ 1.60(d, 3H,CH$_3$), 2.08(s, 3H,O=C—CH$_3$), 3.76 (s,3H,ester), 4.66(q,1H,CH), 6.72 (d,2H,Ar), 7.32(d,2H,Ar), 8.04(bs,1H,NH).

EXAMPLE 63

2-(4-Amino-phenoxy)-propionic acid (63)

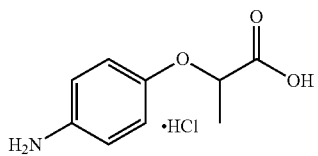

To a mixture 2-(4-acetylamino-phenoxy)-propionic acid methyl ester 62 (320 grams, 1.35 mol) in concentrated hydrochloric acid (8 liters) was refluxed for 48 hours. Excess concentrated hydrochloric acid was distilled in vacuum and filtered hot. The mixture was cooled to 10° C., filtered and dried to give pure 63 (240 grams, 81.7%) as a brown powder. The melting point was found to be 175-180° C.

EXAMPLE 64

2-(4-Amino-phenoxy)-propionic acid methyl ester (64)

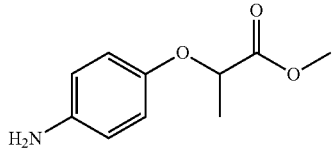

To a mixture of 2-(4-Amino-phenoxy)-propionic acid 63 (240 grams, 1.103 mmol), in Methanol (4.8 liters) was passed dry HCl gas at 10° C. for 1 hour and refluxed for 48 hours. Methanol (2.5 liter) was distilled, ice water (1 liter) was added and the pH was adjusted to 7.5 with $K_2CO_3$. Crude 64 was extracted into chloroform, washed with 5% NaHCO$_3$ solution, water, dried over Na$_2$SO$_4$ and distilled to give 64 (80 grams, 37.2%) as a brown syrup. The structure was confirmed with NMR. $^1$HNMR (CDCl$_3$) δ 1.56(d, 3H,CH$_3$), 2.9(bs, 2H,—NH$_2$), 3.72(s,3H,ester), 4.58(q,1H,CH), 6.53 (d,2H, Ar), 6.68(d,2H,Ar).

EXAMPLE 65

6-(4-Acetylamino-phenoxy)-hexanoic acid methyl ester (65)

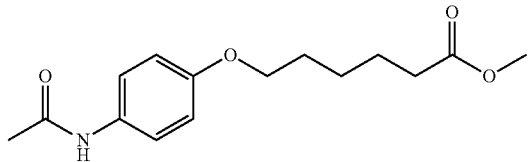 [SMILES: COC(=O)CCCCCOc1ccc(NC(C)=O)cc1]

To a mixture of Paracetamol (250 grams, 1.654 mmol), anhydrous $K_2CO_3$ (800 grams, 5.789 mmol), sodium iodide (17 grams, 113 mmol) in anhydrous acetone (5 liters) was added methyl 6-bromo hexanoate (470 grams, 2.25 mmol) and refluxed for 60 hours. Acetone was distilled and water (3 liter) was added. Crude 65 was filtered, dried, and recrystallized from a mixture of chloroform:Hexane (1:5) to give pure 65 (195 grams, 66%) as a white powder. The melting point was found to be 96.4-98.8° C. The product was tested by HPLC and found to be 99%+ pure. The structure was confirmed with NMR. $^1$HNMR (CDCl$_3$) δ 1.54(m, 2H,CH$_2$), 1.80(m, 4H, CH$_2$), 2.14(s, 3H, O=C—CH$_2$), 2.38(t, 2H, CH$_2$), 3.68(s,3H,ester), 3.92(t,2H,OCH$_2$), 6.68(d,2H,Ar), 7.05 (bs,1H,NH), 7.38 (d,2H,Ar).

EXAMPLE 66

6-(4-Amino-phenoxy)-hexanoic acid Hydrochloride (66)

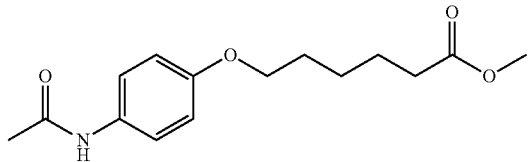 [SMILES: COC(=O)CCCCCOc1ccc(NC(C)=O)cc1]

To a mixture of 6-(4-Acetylamino-phenoxy)-hexanoic acid methyl ester 65 (290 grams, 1.04 moles), in concentrated hydrochloric acid (7.12 Liter) was refluxed for 48 hours. Excess concentrated hydrochloric acid was distilled off in vacuum and filtered hot. The mixture was cooled to 10° C.,

EXAMPLE 67

6-(4-Amino-phenoxy)-hexanoic acid methyl ester (67)

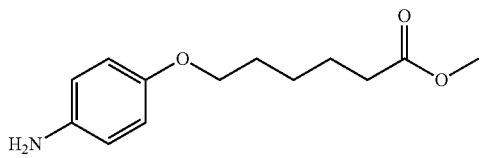 [SMILES: COC(=O)CCCCCOc1ccc(N)cc1]

To a mixture of 6-(4-Amino-phenoxy)-hexanoic acid Hydrochloride 66 (150 grams, 578 mmol), in methanol (3 liters) was passed dry HCl gas at 10° C. for 1 hour and refluxed for 48 hours. Methanol (1.5 liter) was distilled, ice water (1 liter) was added and the pH was adjusted to 7.5 with $K_2CO_3$. Crude 67 was extracted into chloroform, washed with 5% $NaHCO_3$ solution, water, dried over $Na_2SO_4$ and distilled to give 67 (60 grams, 43.8) as a thick brown syrup. The structure was confirmed with NMR. $^1$HNMR ($CDCl_3$) δ 1.5 (m, $2H,CH_2$), 1.72(m, $4H, CH_2$), 2.34(t, $2H, CH_2$), 3.66 (s,3H,ester), 3.85(t,$2H,OCH_2$), 6.56(d,2H,Ar), 6.68(d,2H,Ar).

EXAMPLE 68

(4-Formylphenoxy)acetic acid methyl ester (68)

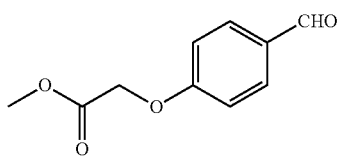

To a mixture of 4-hydroxy benzaldehyde (200 grams, 1.64 mol), anhydrous $K_2CO_3$ (600 grams, 4.34 mol) and sodium iodide (20 grams, 133 mol) in anhydrous acetone (2500 mL) was added methyl chloro acetate (223 grams, 2.055 mol) and refluxed for 12 hours. Acetone was distilled and water (1800 mL) was added. Crude 68 was extracted in to chloroform, dried over $Na_2SO_4$, distilled and purified by column chromatography on silica gel using hexane as eluant to give pure 68 (210 grams, 66.1%) as a white powder.

EXAMPLE 69

(4-Hydroxymethyl-phenoxy)-acetic acid methyl ester (69)

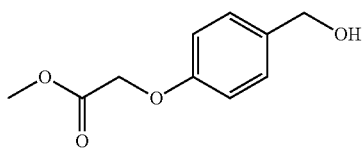

To a solution of (4-Formylphenoxy)acetic acid methyl ester 68 (160 grams, 825 mmol) in methanol (800 mL) at 0° C. was added Sodium borohydrate (18 grams, 476 mmol) in small portions, further stirred at 0° C. for 2 hours and poured on to ice water (1500 mL). The pH of mixture was adjusted to 2 with concentrated hydrochloric acid. Crude 69 was extracted into chloroform, dried over $Na_2SO_4$, distilled and purified by column chromatography on silica gel using hexane:ethyl acetate (7:3) to give 69 (100 grams, 62%) as white powder

EXAMPLE 70

(4-Acetoxymethyl-phenoxy)-acetic acid methyl ester (70)

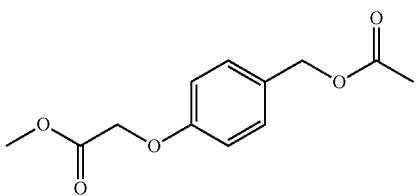 [SMILES: COC(=O)COc1ccc(COC(C)=O)cc1]

A solution of (4-hydroxymethyl-phenoxy)-acetic acid methyl ester 69 (100 grams, 509 mmol), acetic anhydride (250 mL) and pyridine (20 mL) was refluxed for 4 hours. Reaction mixture was poured in to ice water (1000 mL) and crude 70 was extracted into chloroform, dried over $Na_2SO_4$, and distilled. The crude was vacuum distilled to give pure 70 (75 grams, 61.7%) as a light yellow syrup, $Bp_{15}$ 206-210° C. The structure was confirmed with NMR. $^1$HNMR ($CDCl_3$) δ 2.05 (s, $3H,O=C-CH_3$), 3.78(s, 3H,ester), 4.62(s, $2H,OCH_2$), 5.02 (s, 2H, $CH_2$), 6.88 (d,2H,Ar), 7.33 (d, 2H,Ar).

EXAMPLE 71

(4-Formyl-2-methoxy-phenoxy)acetic acid methyl ester (71)

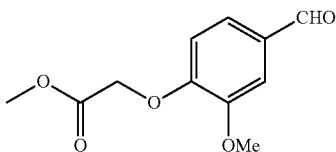 [SMILES: COC(=O)COc1ccc(C=O)cc1OC]

To a mixture of Vanillin (125 grams, 821.5 mmol), anhydrous $K_2CO_3$ (300 grams, 2.17 mol) and sodium iodide (10 grams, 66.7 mmol) in anhydrous acetone (1250 mL) was added methyl chloro acetate (111 grams, 1.023 mol) and refluxed for 8 hours. Acetone was distilled and water (1200 mL) was added. Crude 71 was filtered, dried, and recrystallized from a mixture of Toluene:Hexane (1:5) to give pure 71 (139 grams, 75.5%) as a white powder. The melting point was found to be 93.5-95.5° C. The structure was confirmed with IR and NMR. $^1$HNMR ($CDCl_3$) δ 3.80 (s, 3H,ester), 3.96(s, $3H,OCH_3$), 4.78(s, $2H,OCH_2$), 6.82(d, 1H,Ar), 7.38(m, 2H,Ar), 9.82(s 1H,CHO).

EXAMPLE 72

(4-Hydroxymethyl-2-methoxy-phenoxy)-acetic acid methyl ester (72)

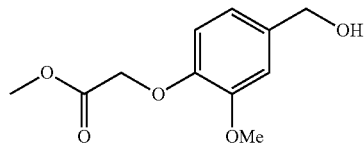 [SMILES: COC(=O)COc1ccc(CO)cc1OC]

To a solution of (4-Formyl-2-methoxy-phenoxy)acetic acid methyl ester 71 (50 grams, 223 mmol) in methanol (500 mL) at 0° C. was added Sodium boro hydrate (4 grams, 106 mmol) in small portions, further stirred at 0° C. for 30 minutes and poured on to ice water (200 mL). The pH of mixture was adjusted to 2 with concentrated hydrochloric acid. Crude 72 was extracted into chloroform, dried over $Na_2SO_4$ and distilled to give 72 (40 grams, 62%) as a light yellow syrup.

EXAMPLE 73

(4-Acetoxymethyl-2-methoxy-phenoxy)-acetic acid methyl ester (73)

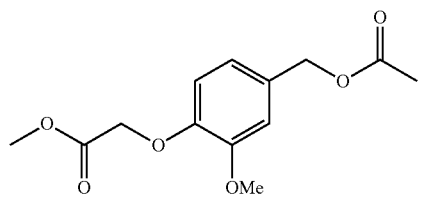 [SMILES: COC(=O)COc1ccc(COC(C)=O)cc1OC]

A solution of (4-Hydroxymethyl-2-methoxy-phenoxy)-acetic acid methyl ester 72 (40 grams, 177 mmol), Acetic anhydride (80 mL) and pyridine (4 mL) was refluxed for 4 hours. Reaction mixture was poured in to ice water (200 mL) and crude 73 was extracted into chloroform, dried over $Na_2SO_4$, and distilled. The crude was vacuum distilled to give pure 73 (30 grams, 64%) as a color less liquid, $B_{p15}$ 210° C. The structure was confirmed with IR and NMR. $^1$HNMR (CDCl$_3$) δ 2.08 (s, 3H,O=C—CH$_3$), 3.78(s, 3H,ester), 3.90 (s, 3H, OCH$_3$), 4.65(s, 2H,OCH$_2$), 5.00 (s, 2H, CH$_2$), 6.76(d, 1H,Ar), 6.80 (d, 2H,Ar), 6.85 (dd,1H,Ar).

EXAMPLE 74

[2-(4-Nitrophenoxy)-ethoxy]acetic acid methyl ester (74)

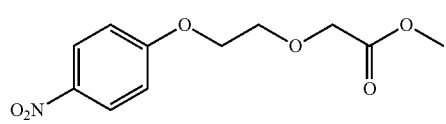 [SMILES: COC(=O)COCCOc1ccc([N+](=O)[O-])cc1]

To a mixture of 4-Nitrophenol (5 grams, 36 mmol), anhydrous $K_2CO_3$ (20 grams, 145 mmol) and sodium iodide (2 grams, 13.3 mmol) in anhydrous acetone (100 mL) was added (2-Bromoethoxy)acetic acid methyl ester (11 grams, 56 mmol) and refluxed for 24 hours. Acetone was distilled and water (100 mL) was added. Crude 74 was filtered, dried and purified by column chromatography on silica gel using benzene as eluant give pure 74 (4 grams, 43.6%) as a white fluffy powder. The melting point was found to be 96-97.8° C. The structure was confirmed with IR and NMR. $^1$HNMR (CDCl$_3$+ DMSO) δ 3.72 (s, 3H,ester), 3.94(t, 2H,OCH$_2$), 4.18(s, 2H,OCH$_2$), 4.30(t, 2H,OCH$_2$), 7.08(d, 2H,Ar), 8.18(d,2H, Ar).

EXAMPLE 75

[2-(4-Amino-phenoxy)-ethoxy]-acetic acid methyl ester (75)

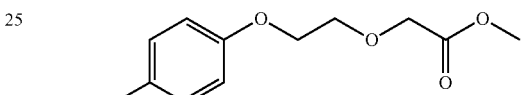

[2-(4-Nitrophenoxy)-ethoxy]acetic acid methyl ester 74 (1 grams, 3.9 mmol) was dissolved in anhydrous ethyl acetate (20 mL), palladium carbon (10%, 0.1 gram) added and the mixture stirred under an atmosphere of H using balloon for 30 minutes. The catalyst was filtered, the filtrate concentrate hexane (3 mL) added, filtered solid to give 75 (625 mg, 70.9%) as a light brown powder. The melting point was found to be 51-52.5° C. The structure was confirmed with IR and NMR. $^1$HNMR (CDCl$_3$) 3.04 (bs, 2H,NH$_2$), 3.72 (s, 3H,ester), 3.88(t, 2H,OCH$_2$), 4.08(t, 2H,OCH$_2$), 4.20(s, 2H,OCH$_2$), 6.58(d, 2H,Ar), 6.70(d,2H,Ar).

EXAMPLE 76

4-Carboxymethoxy-benzoic acid (76)

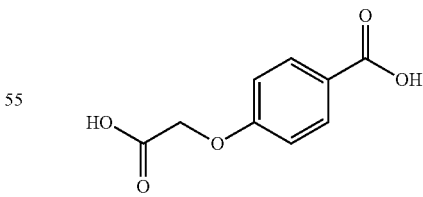

4-Methoxycarbonylmethoxy-benzoic acid methyl ester 1 (50 grams, 223 mmol) was added to a solution of 2.5 M sodium hydroxide (250 mL) and heated to 80° C. for 5 hours. The reaction mixture was dilated with water (100 mL) and pH adjusted to 1 with concentrated HCl. Crude 76 was filtered, dried and given hot ethyl acetate slurry to give 76 (40 grams, 91.4%) as a white powder. M.p: >280° C.

EXAMPLE 77

4-Methoxycarbonylmethoxycarbonylmethoxy-benzoic acid methoxycarbonyl methyl ester (77)

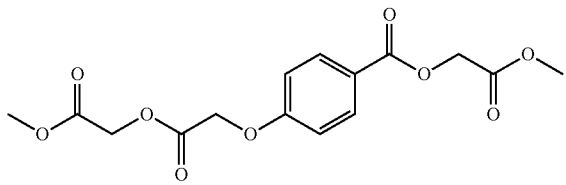

To a mixture of 4-carboxymethoxy-benzoic acid 76 (22 grams, 112.2 mmol), triethylamine (29.4 grams, 290.5 mmol) in acetone (100 mL) was added methyl chloro acetate (31 grams, 285.6 mmol) drop wise, later heated to reflux for 18 hours. The solids were filtered, acetone distilled and water (100 mL) was added. Crude 77 was filtered, dried and purified by column chromatography on silica gel using chloroform as eluant to give pure 77 (25 grams, 65.5%) as a white powder. M.p: 61-64° C.

EXAMPLE 78

4-Methoxycarbonylmethoxy-benzoic acid methoxycarbonylmethyl ester (78)

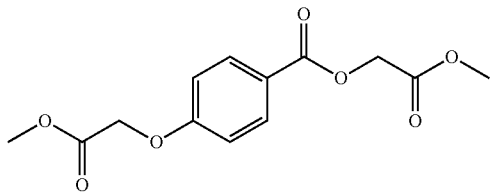

To a mixture of 4-hydroxy benzoic acid (210 grams, 1.519 mole), anhydrous $K_2CO_3$ (945 grams, 6.838 mol) in anhydrous dimethyl formamide (2 liter) at 90° C. was added methyl chloro acetate (388 grams, 3.575 mol) drop wise and maintained 90° C. for 16 hours. Reaction mixture was cooled to room temperature and poured onto ice water (3 liter). Crude 78 was extracted into chloroform, dried over $Na_2SO_4$, distilled and purified by column chromatography on silica gel using hexane as eluant to give pure 78 (35 grams, 8.2%) as a white powder. M.p: 53-57° C. $^1$HNMR (CDCl$_3$) δ 3.80(s,3H, ester), δ 3.81(s,3H, ester), 4.68(s,2H,OCH$_2$), 4.88(s, 2H,OCH$_2$), 6.92(d,2H,Ar), 8.04(d,2H,Ar).

EXAMPLE 79

2-Methoxycarbonylmethoxy-benzoic acid methoxycarbonylmethyl ester (79)

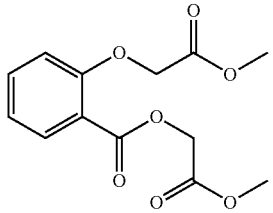 [SMILES: COC(=O)COC(=O)c1ccccc1OCC(=O)OC]

To a mixture of Salicylic acid (10 g, 72.46 mmol), Triethylamine (8.8 g, 86.96 mmol) in acetone (50 mL) was added methyl chloro acetate (9.4 g, 86.66 mmol) drop wise and heated to reflux for 10 hrs. The Solids were filtered off and to the acetone layer was added Potassium carbonate (25 g, 180.89 mmol), Sodium Iodide (2 g, 13.34 mmol), disodium Phosphate (2 g, 14.16 mmol), methyl chloro acetate (9.4 g, 86.66 mmol) and refluxed for 16 hrs. Acetone was distilled and water (125 mL) added. The crude 79 was extracted into chloroform, washed with 5% sodium bicarbonate solution (2×50 mL), water (2×50 mL), dried over sodium sulphate and distilled. The crude 79 was purified by column chromatography on silica gel using benzene to get pure 79 (12 g, 58.7%) as a syrup.

EXAMPLE 80

2-Carboxymethoxy-benzoic acid (80)

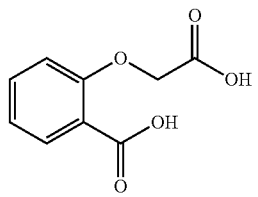 [SMILES: O=C(O)COc1ccccc1C(=O)O]

To 10% Solution of Sodium hydroxide (475 mL) was added 2-Methoxycarbonylmethoxy-benzoic acid methyl ester 5 (95 grams, 424 mmol) and heated to 80° C. for 4 hours. Reaction mixture was cooled to room temperature and pH adjusted so 2 with dilute Hydrochloric acid. The crude 80 was purified by dissolving in 10% NaOH and precipitating by acidifying with HCl, to get pure 80 (65 grams, 78.2%) as white powder. M.p: 189-192° C.

EXAMPLE 81

2-Methoxycarbonylmethoxycarbonylmethoxy-benzoic acid methoxycarbonyl methyl ester (81)

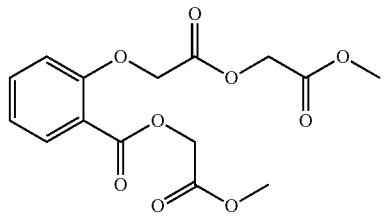 [SMILES: COC(=O)COC(=O)COc1ccccc1C(=O)OCC(=O)OC]

To mixture of 2-Carboxymethoxy-benzoic acid 80 (34 grams, 173.5 mmol) Triethylamine (37 grams, 365.6 mmol) in acetone (100 mL) was added methyl chloro acetate (39 grams, 359 mmol) drop wise, later stirred under reflux for 24 hours. The solids were filtered off, acetone distilled and cold water (150 mL) was added. Crude 81 was extracted into chloroform, washed with 5% Sodium bicarbonate (2×100 mL), water (2×100 mL), dried over sodium sulphate and distilled. The crude 81 was purified by column chromatography on silica gel using Hexane as eluant to get pure 81 (31 grams, 52.5%) as a light yellow syrup.

EXAMPLE 82

(4-Methoxycarbonylmethoxy-phenoxy)-acetic acid methyl ester (82)

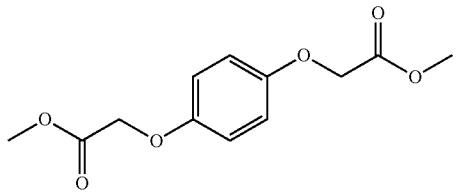

To a mixture of sodium hydride (60%, 92 grams, 2.3 moles) in DMF (400 mL) at 0° C. was added hydroquinone (100 grams, 909 mmol) carefully and stirred for 30 minutes. Methyl chloro acetate (247 grams, 2.276 moles) was added drop wise and later stirred at room temperature for 2 hours. Reaction mixture was carefully quenched into ice water (2 lit). Crude 82 was filtered, dried, and recrystallized from a mixture of Ethyl acetate:Hexane (1:6) to give pure 82 (95 grams, 41.1%) as a white powder. M.p: 96-98° C. $^{1}$H NMR (CDCl$_3$) δ 3.68(s,3H,Ester), 4.54(s, 2H,OCH$_2$), 6.82(s,2H, Ar).

EXAMPLE 83

(4-Carboxymethoxy-phenoxy)-acetic acid (83)

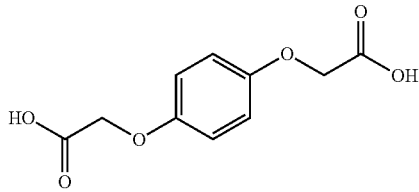 [SMILES: O=C(O)COc1ccc(OCC(=O)O)cc1]

(4-Methoxycarbonylmethoxy-phenoxy)-acetic acid methyl ester 82 (100 grams, 394 mmol) was added to 3.25 M-sodium hydroxide solution (600 mL) and heated to 70° C. for 20 hours and poured onto ice cold water (1 lit) and the pH adjusted to 1 with concentrated hydrochloric acid. Crude 83 was filtered, dried, and recrystallized from DMF by precipitating with water to give pure 83 (60 grams, 67.4%) as a white powder. M.p: 254-256.5° C. $^{1}$H NMR (CDCl$_3$+DMSO, d$_6$) 4.44(s,2H,OCH$_2$), 6.72(s,2H,Ar).

EXAMPLE 84

(4-Methoxycarbonylmethoxycarbonylmethoxy-phenoxy)-acetic acid methoxycarbonyl methyl ester (84)

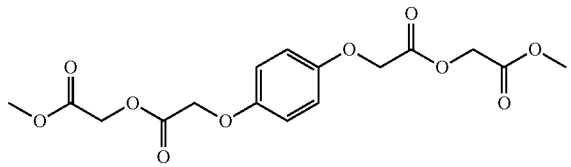

To a mixture of (4-Carboxymethoxy-phenoxy)-acetic acid 83 (50 grams, 221 mmol), Triethylamine (51 grams, 504 mmol) in acetone (250 mL) was added methyl chloro acetate (53 grams, 488 mmol) drop wise and heated to reflux for 18 hours. The solids were filtered, acetone distilled and water (200 mL) was added. Crude 84 was extracted into chloroform, washed with 5% sodium bicarbonate solution (2×100 mL), water (2×100 mL), dried over sodium sulphate and distilled. Crude 84 was recrystallized from a mixture of chloroform:Hexane (1:6) to give pure 84 (57 grams, 69.7%) as a white powder. M.p: 124-126° C. $^{1}$H NMR (CDCl$_3$) δ 3.80(s, 3H,Ester), 4.70(s,2H,OCH$_2$), 4.72(s,2H,OCH$_2$), 6.90(s,2H, Ar).

EXAMPLE 85

2-{2-[4-(1-Methoxycarbonyl-ethoxycarbonyl-methoxy)-phenoxy]-acetoxy}-propionic acid methyl ester (85)

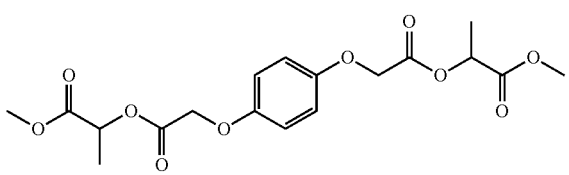

To mixture of (4-Carboxymethoxy-phenoxy)-acetic acid 83 (20 grams, 88.4 mmol), Triethylamine (45 grams, 444.7 mmol) in Acetone (300 mL) was added methyl chloroacetate (32.5 grams, 265 mmol) drop wise at reflux temperature and further refluxed for 48 hours. The solids were filtered, acetone distilled and water (200 mL) was added. Crude 85 was extracted into chloroform, washed with 5% Sodium bicarbonate (2×100 mL), water (2×100 mL), dried over sodium sulphate and distilled. The crude 85 was purified by column chromatography over silica gel using chloroform as eluant to get pure 85 (11 grams, 31.2%) as a light yellow syrup. $^{1}$H NMR (CDCl$_3$) δ 1.5(d,3H,CH$_3$), 3.72(s,3H,Ester), 4.62(s, 2H,OCH$_2$), 5.14 (q,1H,CH), 6.82(s,2H,Ar).

EXAMPLE 86

2-[4-(1-Methoxycarbonyl-ethoxy)-phenoxy]-propionic acid methyl ester

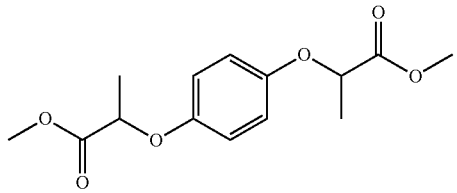

To a mixture of hydroquinone (50 grams, 454.5 mmol), potassium carbonate (252 grams, 1.823 moles), sodium iodide (5 grams, 33.3 mmol), disodium phosphate (5 grams, 35.4 mmol) in anhydrous DMF (750 mL) at 70° C. was added methyl 2-chloro propionate (139 grams, 1.135 moles) drop wise. Later heated to 100° C. for 20 hours. Reaction mixture was cooled to room temperature and poured onto ice cold water (2.5 lit). Crude 86 was extracted into chloroform, washed with water (2×500 mL), dried over sodium sulphate, distilled and purified by column chromatography on silica gel using benzene as eluant to give pure 86 (44 grams, 34.3%) as a low melting white solid. $^1$H NMR (CDCl$_3$) δ 1.60 (d,3H, CH$_3$), 3.75(s,3H,Ester), 4.64(q,1H,CH), 6.78(s,2H,Ar).

EXAMPLE 87

2-[4-(1-Carboxy-ethoxy)-phenoxy]-propionic acid (87)

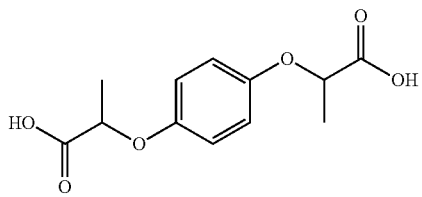 [SMILES: CC(Oc1ccc(OC(C)C(=O)O)cc1)C(=O)O]

A mixture of 2-[4-(1-Methoxycarbonyl-ethoxy)-phenoxy]-propionic acid methyl ester 86 (20 grams, 70.9 mmol) in concentrated hydrochloric acid (100 mL) was heated to 90° C. for 8 hours. The reaction mixture was poured onto ice cold water (200 mL) and filtered the separated solid, washed with methanol and dried to give crude 87 (7 grams, 38.8%) as a white solid. M.p: 235-239.7° C.

EXAMPLE 88

2-[4-(1-Methoxycarbonylmethoxycarbonyl-ethoxy)-phenoxy]-propionic acid methoxy carbonyl methyl ester (88)

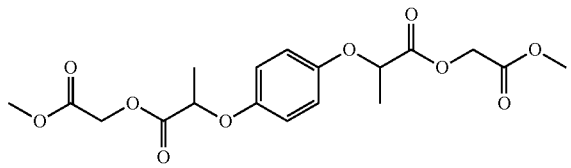

To a mixture of 2-[4-(1-carboxy-ethoxy)-phenoxy]-propionic acid 87 (5 grams, 19.68 mmol), Triethylamine (10.16 grams, 100 mmol) in acetone was added methyl chloro acetate (7.4 grams, 68.2 mmol) drop wise and later refluxed for 6 hours. The solids were filtered, acetone distilled and water (50 mL) was added. Crude 88 was extracted into chloroform, washed with 5% sodium bicarbonate (2×20 mL), water (2×20 mL), dried over sodium sulphate and distilled. The crude 88 was purified by column chromatography on silica gel using chloroform as eluant to give pure 88 (7 grams, 89.3%) as a white powder. Analytical sample was prepared by recrystallising the above solid in a mixture of chloroform: Hexane to get 4 grams of pure 88. M.p: 90.5-92.5° C. $^1$HNMR (CDCl$_3$) δ 1.66(d,3H,CH$_3$), 3.75(s,3H,Ester), 4.64(s,2H, OCH$_2$), 4.72(q,1H,CH), 6.80(s,2H,Ar).

EXAMPLE 89

2-(6-Carboxymethoxy-naphthalen-2-yl)-propionic acid (89)

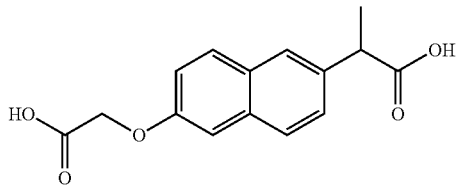 [SMILES: CC(C(=O)O)c1ccc2cc(OCC(=O)O)ccc2c1]

A mixture of 2-(6-Methoxycarbonylmethoxy-naphthalen-2-yl)-propionic acid methyl ester 31 (23 grams, 76.16 mmol) in 4 N—NaOH solutions (230 mL) was heated on a water bath at 90° C. for 8 hours. The reaction mass was cooled to room temperature and the pH adjusted to 2 with concentrated hydrochloric acid. Crude 89 was filtered, dried, and recrystallized from a mixture of ethyl acetate:hexane (1:6) to give pure 89 (15 grams, 71.9%) as a white powder. Mp: 185-188° C. $^1$H NMR (DMSO-d$_6$) δ 1.54(d,3H,CH$_3$), 3.80(q,1H,CH), 4.74(s,2H,OCH$_2$), 7.08(s,1H,Ar), 7.22(m,1H,Ar), 7.42(m,1H,Ar), 7.66(m,3H,Ar).

EXAMPLE 90

2-(6-Methoxycarbonylmethoxycarbonylmethoxy-naphthalen-2-yl)-propionic acid methoxy carbonyl-methyl ester (90)

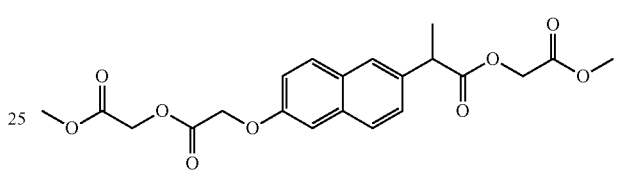

To a mixture of 2-(6-carboxymethoxy-naphthalen-2-yl)-propionic acid 89 (18 g, 65.69 mmol) Triethyl amine (20.25 g, 200.1 mmol) in acetone (180 mL) was added methyl chloro acetone (22.2 g, 204.5 mmol) drop wise, later heated to reflux for 21 hrs. Solids were filtered off, acetone distilled and water (100 mL) was added. Crude 90 was extracted into chloroform, washed with 5% sodium bicarbonate (2×50 mL), water (2×50 mL), dried over sodium sulphate and distilled. The crude 90 was purified by column chromatography on silica gel using Benzene as eluant to give pure 90 (21 g, 76.5%) as a light yellow syrup. $^1$HNMR (CDCl$_3$) δ 1.60(d,3H,CH$_3$), 3.68(s,3H,Ester), 3.74(s,3H,Ester), 3.92(q,1H,CH), 4.55(dd, 2H,CH$_2$), 4.70(s,2H,CH$_2$), 4.80 (s,2H,CH$_2$), 7.08(d,1H,Ar), 7.18 (m,1H,Ar), 7.30(s,1H,Ar), 7.40(m,1H,Ar), 7.68(m,2H, Ar).

EXAMPLE 91

2-(6-Hydroxy-naphthalen-2-yl)-propionic acid methoxycarbonylmethyl ester (91)

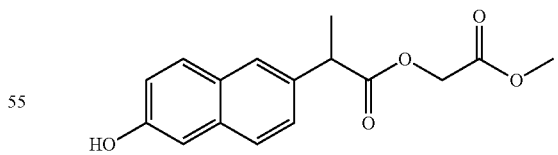

To a mixture of 2-(6-Hydroxy-naphthalen-2-yl)-propionic acid 29 (10 grams, 46.2 mmol), Triethylamine (4.7 grams, 46.4 mmol) in acetone (100 mL) was added methyl chloro acetate (8 grams, 73.7 mmol) and refluxed for 24 hours. The solids were filtered, acetone distilled, crude 91 extracted into chloroform, washed with 5% sodium bicarbonate (2×15 mL), water (2×15 mL), dried over sodium sulphate and distilled. Crude 91 was purified by crystallization from a mixture of Chloroform:Hexane (1:6) to get pure 91 (7 grams, 52.5%) as white powder. M.p: 84.5-87° C. $^1$HNMR (CDCl$_3$) δ 1.62(d, 3H,CH$_3$), 3.72(s,3H,Ester), 3.94(q,1H,CH), 4.62 (d,2H, CH$_2$), 7.00(m,2H,Ar), 7.3 (d,1H,Ar), 7.56(m,3H,Ar).

EXAMPLE 92

2-(6-Methoxycarbonylmethoxy-naphthalen-2-yl)-propionic acid methoxy carbonyl methyl ester (92)

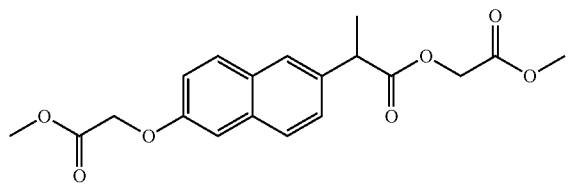

To a mixture of 2-(6-Hydroxy-naphthalen-2-yl)-propionic acid 29 (25 g, 115.74 mmol) Triethylamine (15.2 g, 150.2 mmol) in acetone (125 mL) was added methyl chloro acetate (13.8 g, 127.16 mmol) drop wise and heated to reflux for 24 hrs. The Solids were filtered off and to the acetone layer was added Potassium carbonate (30 g, 217 mmol), Sodium Iodide (4 g, 26.68 mmol), disodium Phosphate (4 g, 28.33 mmol), methyl chloro acetate (18 g, 165.86 mmol) and refluxed for 6 hrs. Acetone was distilled and water (125 mL) added. The crude 92 was extracted into chloroform, washed with 5% sodium bicarbonate solution (2×50 mL), water (2×50 mL), dried over sodium sulphate and distilled. The crude 92 was purified by column chromatography on silica gel using Hexane:Ethyl acetate (95:5) to get pure 92 (10 g, 24%) as a light yellow syrup. $^1$HNMR (CDCl$_3$) δ 1.64(d,3H,CH$_3$), 3.72(s, 3H,Ester), 3.84(s,3H,Ester), 3.95(q,1H,CH), 4.58(dd,2H, CH$_2$), 4.62(s,2H,CH$_2$), 7.04(d,1H,Ar), 7.22(m,1H,Ar), 7.40 (m,1H,Ar), 7.70(m,3H,Ar).

EXAMPLE 93

Methyl (4-Nitro phenoxy)acetate (93)

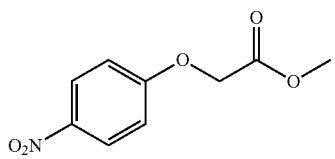

To a mixture of 4-Nitro phenol (100 grams, 719 mmol), anhydrous K$_2$CO$_3$ (400 grams, 2.894 moles) in anhydrous acetone (950 mL) was added methyl chloroacetate (114 grams, 1.050 moles) and refluxed for 12 hours. Acetone was distilled and water (1500 mL) was added. Crude 93 was filtered, dried, and recrystallized from a mixture of Ethyl acetate:Hexane (1:5) to give pure 93 (110 grams, 72.5%) as a white fluffy powder. M.p: 97-98.4° C.

EXAMPLE 94

(4-Nitro phenoxy)acetic acid (94)

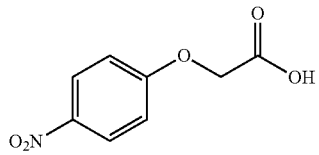 [SMILES: O=C(O)COc1ccc([N+](=O)[O-])cc1]

A mixture of methyl (4-Nitro phenoxy)acetate 93 (100 grams, 474 mmol) and concentrated HCl (1000 mL) was refluxed for 8 hours. The reaction mass was cooled to room temperature. Crude 94 was filtered, dried, and recrystallized from a mixture of Ethyl acetate:Hexane (1:5) to give pure 94 (86 grams, 92.1%) as a white shining powder. M.p: 186-188.5° C.

EXAMPLE 95

(4-Nitro-phenoxy)-acetic acid methoxycarbonylmethyl ester (95)

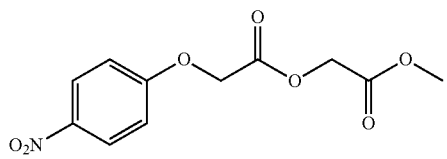

To a mixture (4-Nitrophenoxy)acetic acid 94 (150 grams, 761.4 mmol), Triethylamine (85 grams, 840 mmol) in acetone (750 mL) was added methyl chloroacetate (91.6 grams, 844 mmol) drop wise, later stirred under reflux for 8 hours. Solids were filtered off and poured on to cold 5% sodium bicarbonate solution (4 lit). Crude 95 was filtered, dried, and recrystallized from chloroform:hexane (1:6) to get pure 95 (186 grams, 90.8%) as a white powder. M.p: 88-90° C. $^1$H NMR (CDCl$_3$) δ 3.80(s,3H,Ester), 4.75(s,2H,OCH$_2$), 4.88(s,2H, OCH$_2$), 7.02(d,2H,Ar), 8.22(d,2H,Ar).

EXAMPLE 96

(4-Amino-phenoxy)-acetic acid methoxycarbonylmethyl ester (96)

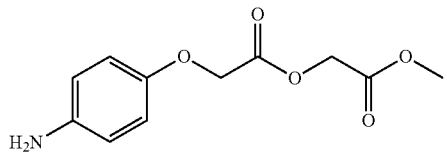 [SMILES: COC(=O)COC(=O)COc1ccc([N+](=O)[O-])cc1]

(4-Nitro-phenoxy)-acetic acid methoxycarbonylmethyl ester 95 (20 grams, 74.3 mmol) was dissolved in dimethyl formamide (100 mL) in a pressure vessel, palladium on carbon (5%, 8 grams) added, and the mixture stirred under an atmosphere of H (4 Kg) for 2 hours. The catalyst was removed by filtration and to the filtrate; ice water (400 mL) was added. Crude 96 was extracted into ethyl acetate, dried over $Na_2SO_4$ and distilled, crude 3 was recrystallized from chloroform: hexane (1:6) to get pure 96 (13 grams, 73%) as a light brown shining powder. M.p: 76.5-78.5° C. $^1$H NMR (CDCl$_3$) δ 3.32 (bs,2H,NH$_2$), 3.76(s,3H,Ester), 4.70(s,2H,OCH$_2$), 4.74(s, 2H,OCH$_2$), 6.60(d,2H,Ar), 6.74(d,2H,Ar).

EXAMPLE 97

[3-(4-Carboxymethoxy-phenyl)-4-oxo-4H-chromen-7-yloxy]-acetic acid (97)

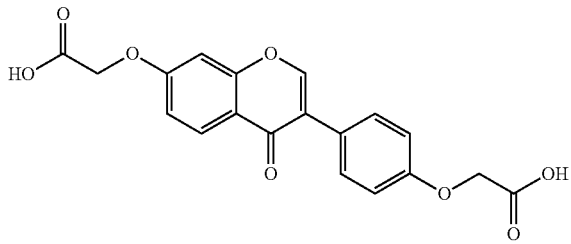 [SMILES: O=C(O)COc1ccc(-c2coc3cc(OCC(=O)O)ccc3c2=O)cc1]

To mixture of [3-(4-Methoxycarbonylmethoxy-phenyl)-4-oxo-4H-chromen-7-yloxy]-acetic acid methyl ester 52 (45 grams, 113.5 mmol) and concentrated hydrochloric acid (250 mL) was heated at 90° C. for 5 hours. The reaction mixture was cooled to room temperature and poured onto ice water (250 mL), filtered the solids, washed with water, methanol and dried. Crude 97 was recrystallized from Dimethyl formamide and Precipitated with water to give pure 97 (36 grams, 86.1%) as a white powder. M.p: 270-272.2° C.

EXAMPLE 98

[4-(7-Methoxycarbonylmethoxycarbonylmethoxy-4-oxo-4H-chromen-3-yl)-phenoxy]-acetic acid methoxycarbonylmethyl ester (98)

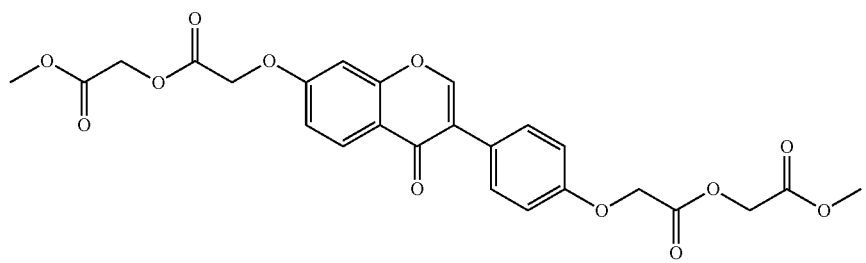

To mixture of [3-(4-Carboxymethoxy-phenyl)-4-oxo-4H-chromen-7-yloxy]-acetic acid 97 (30 grams, 81 mmol), Triethylamine (41 grams, 405 mmol) in acetone (300 mL) was added methyl chloro acetate (31 grams, 286 mmol) drop wise and heated to reflux for 8 hours. Solids were filtered; acetone distilled and poured onto 5% Sodium bicarbonate solution (200 mL). Crude 98 was extracted into chloroform, dried over sodium sulphate and distilled. Crude 98 was recrystallized from a mixture of Chloroform:Hexane (1:6) to get pure 98 (38.5 grams, 92.3%) as a white powder. M.p: 111-114° C. $^1$HNMR (CDCl$_3$+DMSO-d$_6$) δ 3.78(s, 6H, ester×2) 4.74(s, 4H,CH$_2$×2), 4.84(s,2H,CH$_2$), 5.00(s,2H,CH$_2$), 7.00(m,4H, Ar), 7.50(d,2H,Ar), 8.10(d,1H,Ar), 8.18(s,1H,Ar).

In Vitro Hydrolysis of Functionalized Phenolics

A few selected compounds were examined for the rate of hydrolysis by conducting in vitro hydrolysis studies at reflux temperature (100° C.). For each experiment, 500 mg of a functionalized compound and 50 mL of pH 7.4 buffer solution (purchased from Aldrich chemical company) were charged into a 100 mL round bottom flask fitted with a condenser and the contents were refluxed. In vitro hydrolysis of the functionalized phenolic was monitored by thin layer chromatography (TLC) using corresponding starting material (original amino acid) as a control. In vitro hydrolysis was continued at reflux until the functionalized molecule hydrolyzed to the starting compound.

EXAMPLE 99

4-Methoxycarbonylmethoxycarbonylmethoxy-benzoic acid methoxycarbonyl methyl ester (Example 77) was hydrolyzed under the above conditions in 26.5 hours as shown below (99)

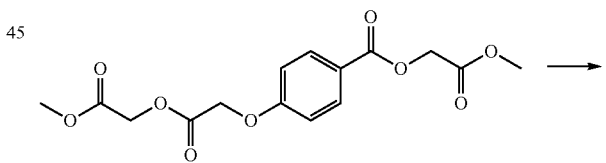

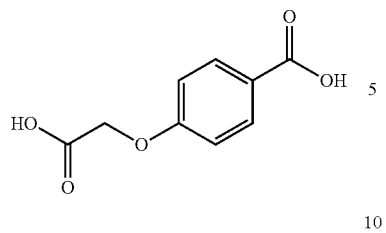

EXAMPLE 100

4-Methoxycarbonylmethoxy-benzoic acid methoxycarbonylmethyl ester (Example 78) was hydrolyzed under the above conditions in 33.0 hours as shown below (100)

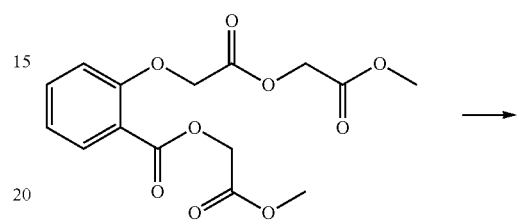

EXAMPLE 101

2-Methoxycarbonylmethoxy-benzoic acid methoxycarbonylmethyl ester (Example 79) was hydrolyzed under the above conditions in eight hours as shown below (101)

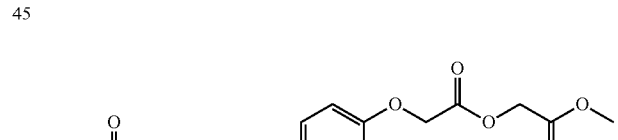

EXAMPLE 102

2-Methoxycarbonylmethoxycarbonylmethoxy-benzoic acid methoxycarbonyl methyl ester (Example 81) was hydrolyzed under the above conditions in two hours as shown below (102)

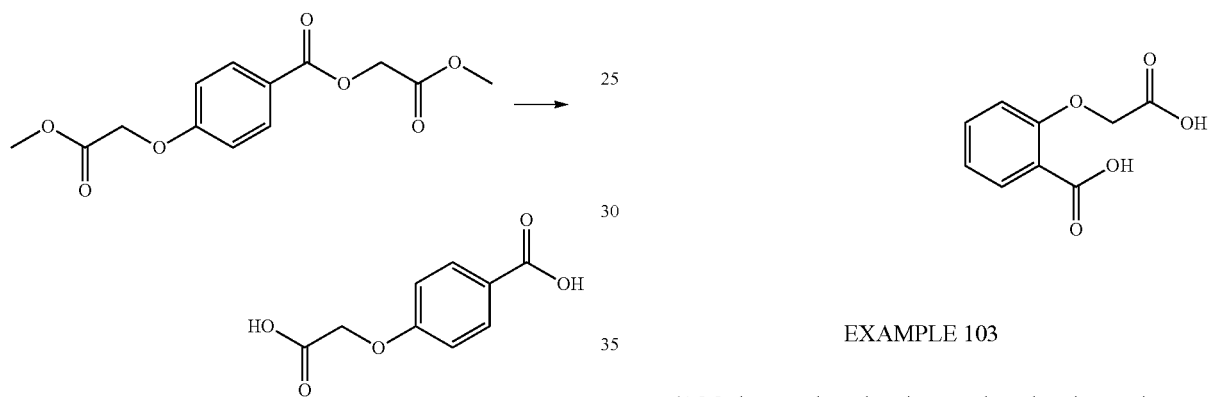

EXAMPLE 103

(4-Methoxycarbonylmethoxycarbonylmethoxy-phenoxy)-acetic acid methoxy carbonyl methyl ester (Example 84) was hydrolyzed under the above conditions in one hour as shown below (103)

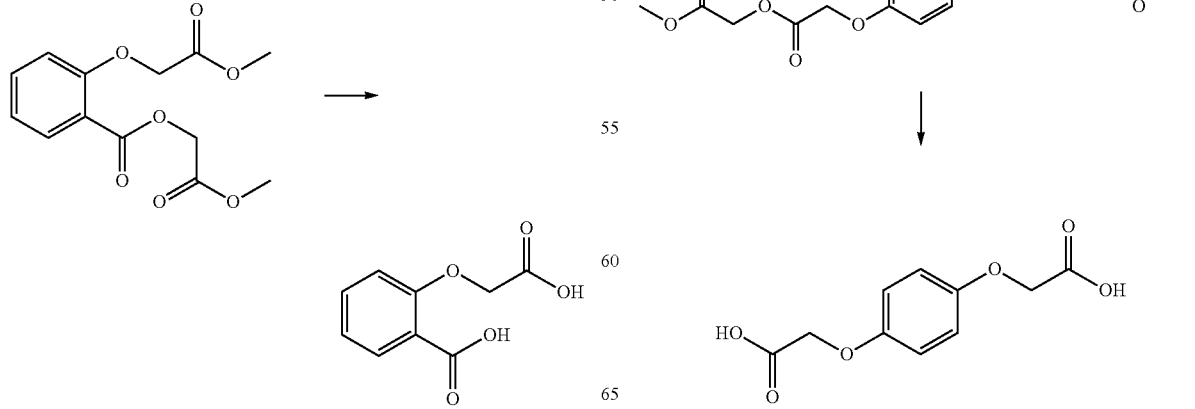

EXAMPLE 104

2-{2-[4-(1-Methoxycarbonyl-ethoxycarbonyl-methoxy)-phenoxy]-acetoxy}-propionic acid methyl ester (Example 85) was hydrolyzed under the above conditions in two hours as shown below (104)

EXAMPLE 105

2-(6-Methoxycarbonylmethoxycarbonylmethoxy-naphthalen-2-yl)-propionic acid methoxy carbonyl methyl ester (Example 90) was hydrolyzed under the above conditions in four hours as shown below (105)

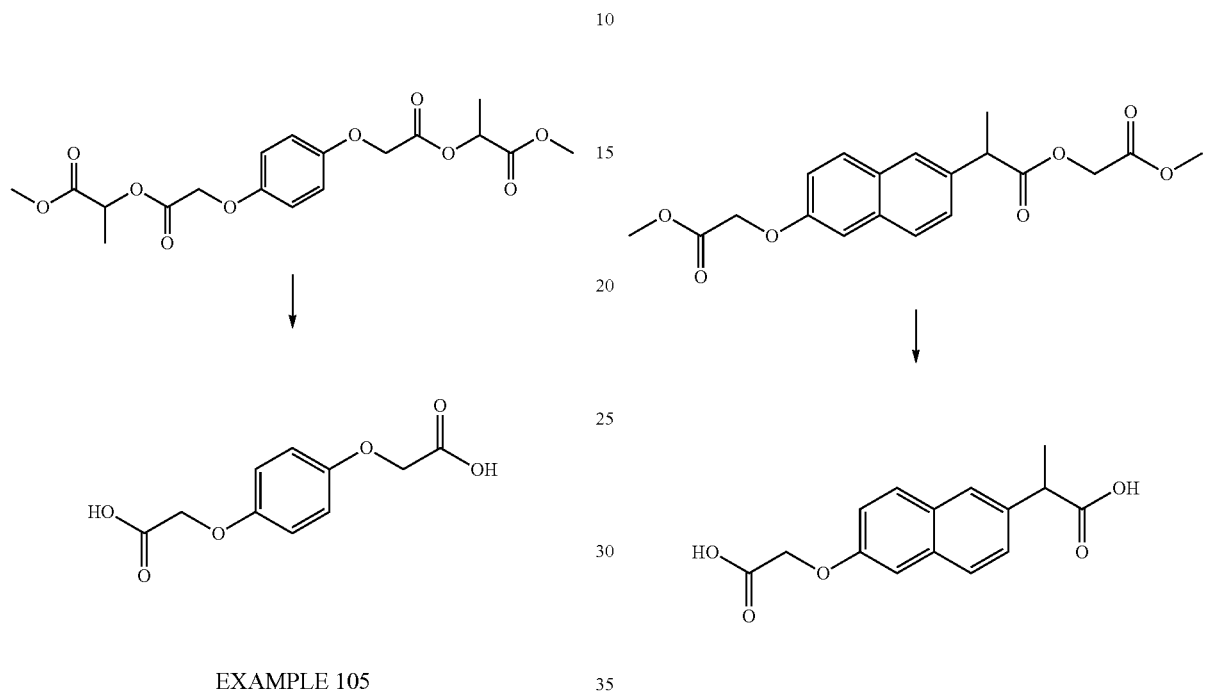

EXAMPLE 106

2-(6-Methoxycarbonylmethoxy-naphthalen-2-yl)-propionic acid methoxy carbonyl methyl ester (Example 92) was hydrolyzed under the above conditions in four hours as shown below (106)

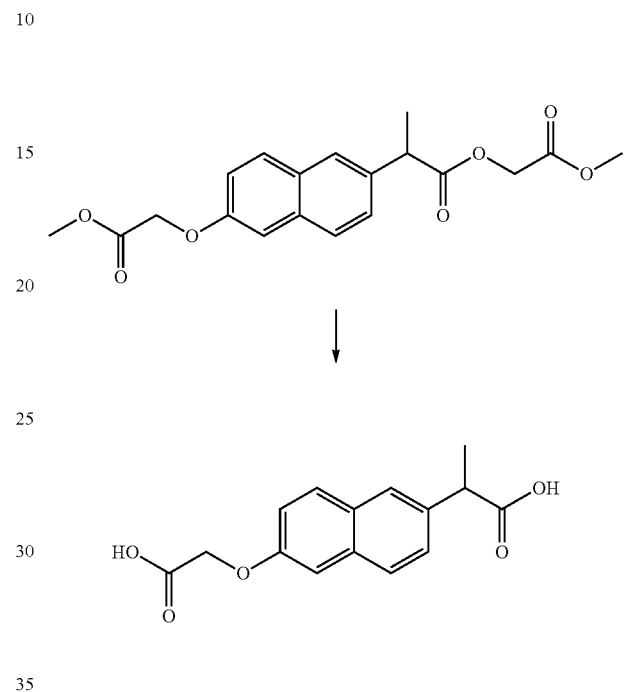

EXAMPLE 107

(4-Amino-phenoxy)-acetic acid methoxycarbonylmethyl ester (Example 96) was hydrolyzed under the above conditions in three hours as shown below (107)

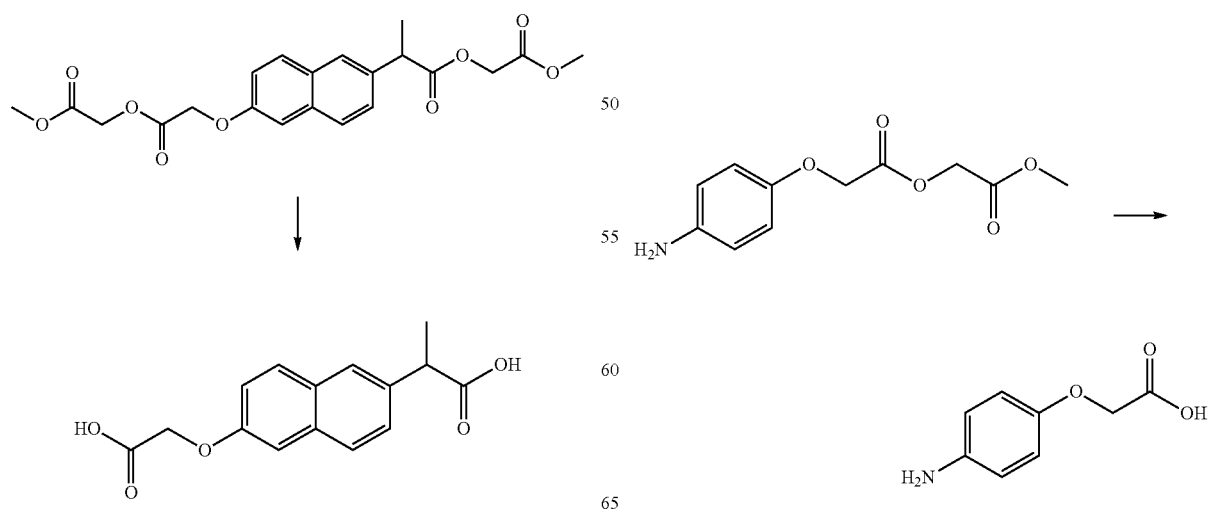

EXAMPLE 108

[4-(7-Methoxycarbonylmethoxycarbonylmethoxy-4-oxo-4H-chromen-3-yl)-phenoxy]-acetic acid methoxy carbonyl methyl ester (Example 98) was hydrolyzed under the above conditions in ten hours as shown below (108)

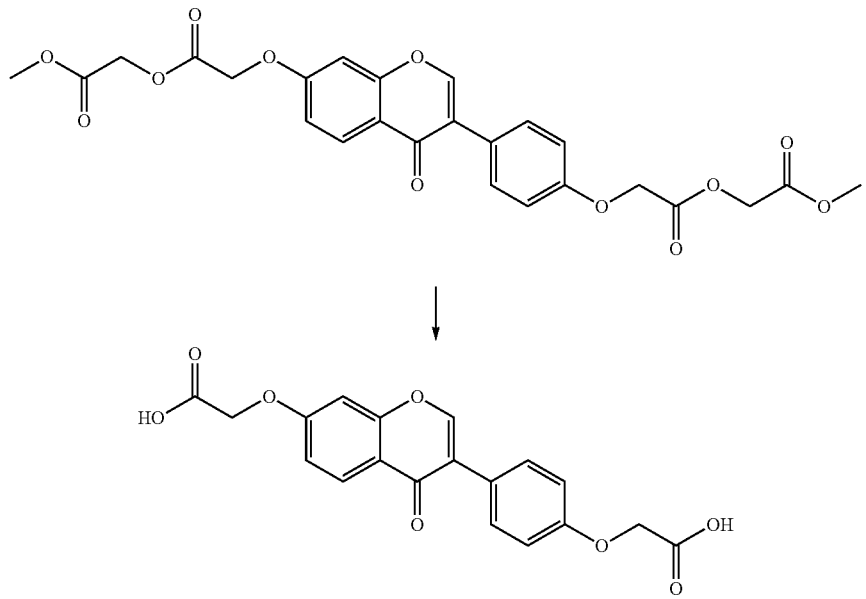

This indicates that the functionalized phenolics of the present invention hydrolyze and also that polymers derived from the functionalized phenolics should hydrolyze. Therefore, using the functionalized phenolics, one can develop polymers with controlled hydrolysis profiles.

What is claimed:

1. A compound of formula (I) or a pharmaceutically acceptable salt thereof:

Ar—[O—(X)$_p$—R']$_q$     (I)

wherein:
Ar is the remainder of a phenolic residue and is selected from: resorcinol, catechol, dihydroxy-naphthyl, tri-hydroxy-naphthyl, tetra-hydroxy-naphthyl, unsubstituted hydroquinone, tri-hydroxy-phenyl, di-hydroxy-benzoic acids, and isoflavones;
X is independently at each occurrence selected from: —CH$_2$COO—; —CH(CH$_3$)COO—; —CH$_2$CH$_2$OCH$_2$COO—; —CH$_2$CH$_2$CH$_2$CH$_2$CH$_2$COO—; —(CH$_2$)$_y$COO—; and, —(CH$_2$CH$_2$O)$_z$CH$_2$COO—;
y is independently selected from 2, 3, 4 and 6-24;
z is independently selected from 2-24;
R' is selected from H, benzyl, and C$_{1-6}$ alkyl;
p is independently selected from 2, 3, and 4; and,
q is selected from 2, 3, 4, 5, 6, 7, 8, 9, and 10.

2. The compound according to claim 1, wherein X is selected from:
—CH$_2$COO—;
—CH(CH$_3$)COO—;
—CH$_2$CH$_2$OCH$_2$COO—; and,
—CH$_2$CH$_2$CH$_2$CH$_2$CH$_2$COO—; and,
q is 2.

3. The compound according to claim 1, wherein X is independently at each occurrence selected from: —CH$_2$COO—; —CH(CH$_3$)COO—; —CH$_2$CH$_2$OCH$_2$COO—; —CH$_2$CH$_2$CH$_2$CH$_2$CH$_2$CO O—; —(CH$_2$)$_y$COO—; and, —(CH$_2$CH$_2$O)$_z$CH$_2$COO—;
y is independently selected from 2, 3, and 4;
z is independently selected from 2, 3, and 4;
p is independently selected from 2 and 3; and,
q is selected from 2 and 3.

4. The compound according to claim 1, wherein: the phenolic residue is a di-hydroxy-benzoic acid.

5. A compound according to claim 1, wherein: the phenolic residue is an isoflavone.

6. The compound of claim 1, wherein the phenolic residue is selected from: resorcinol, catechol, unsubstituted hydroquinone, tri-hydroxy-phenyl, and dihydroxy-benzoic acid.

7. The compound of claim 1, wherein the compound is:

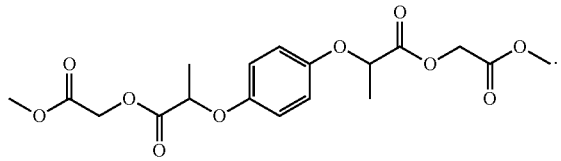

8. The compound of claim 1, wherein the compound is:

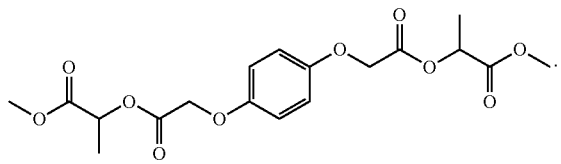

9. The compound of claim 1, wherein the compound is:

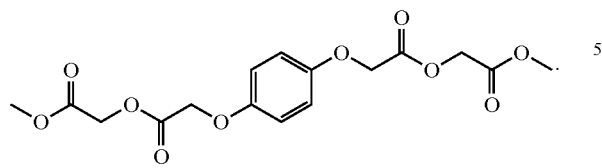

10. The compound of claim 1, wherein the phenolic residue and is an isoflavone that is selected from: glycitein, daidzein, prunetin, biochanin A, orobol, santal, pratensein, and genistein.

11. The compound of claim 1, wherein the compound is

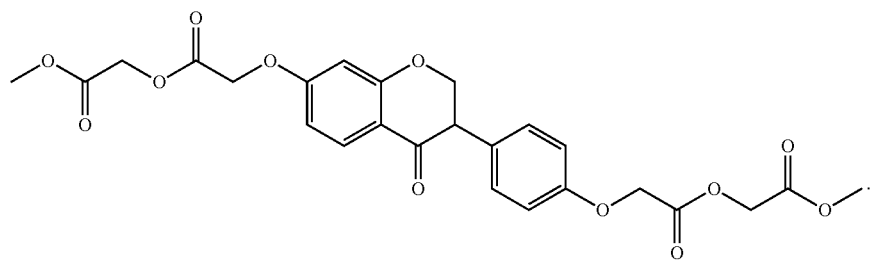

12. The compound of claim 1, wherein the phenolic residue is selected from: resorcinol, catechol, unsubstituted hydroquinone, and tri-hydroxy-phenyl.

13. The compound of claim 1, wherein the phenolic residue is selected from: dihydroxy-naphthyl, tri-hydroxy-naphthyl, and tetra-hydroxy-napthyl.

* * * * *